(12) United States Patent
Creasey et al.

(10) Patent No.: US 10,307,591 B2
(45) Date of Patent: Jun. 4, 2019

(54) TOPICAL NEUROLOGICAL STIMULATION

(71) Applicants: Graham H. Creasey, Menlo Park, CA (US); Hoo-Min Toong, Los Altos Hills, CA (US)

(72) Inventors: Graham H. Creasey, Menlo Park, CA (US); Hoo-Min Toong, Los Altos Hills, CA (US)

(73) Assignee: NEUROSTIM SOLUTIONS, LLC, Waltham, MA (US)

(*) Notice: Subject to any disclaimer, the term of this patent is extended or adjusted under 35 U.S.C. 154(b) by 0 days.

(21) Appl. No.: 15/650,228

(22) Filed: Jul. 14, 2017

(65) Prior Publication Data
US 2017/0312512 A1 Nov. 2, 2017

Related U.S. Application Data

(62) Division of application No. 14/893,946, filed as application No. PCT/US2014/040240 on May 30, 2014, now Pat. No. 10,016,600.
(Continued)

(51) Int. Cl.
A61N 1/36 (2006.01)
A61N 1/04 (2006.01)
(Continued)

(52) U.S. Cl.
CPC ....... A61N 1/36014 (2013.01); A61N 1/0452 (2013.01); A61N 1/0456 (2013.01);
(Continued)

(58) Field of Classification Search
CPC ............ A61N 1/0551; A61N 1/3787; A61N 1/36139; A61N 1/37229; A61N 1/36125; A61N 1/0456; A61N 1/37211; A61N 1/3756; A61N 1/36014; A61N 1/37235; A61N 1/36003; A61N 1/36135; A61N 1/36146; A61N 1/0492; A61N 1/375; A61N 1/36; A61N 1/36132; A61N 1/0484; A61N 1/0452; A61N 1/08; A61N 1/04; A61N 1/0404; A61N 1/0472; A61B 5/4836;
(Continued)

(56) References Cited

U.S. PATENT DOCUMENTS 4,277,980 A 7/1981 Coats et al.
4,532,930 A 8/1985 Crosby et al.
(Continued)

FOREIGN PATENT DOCUMENTS

CN 101868279 A 10/2010
CN 107362447 A 11/2017
(Continued)

OTHER PUBLICATIONS

US 8,398,630 B2, 03/2013, Demarais et al. (withdrawn)
(Continued)

Primary Examiner — Nadia A Mahmood
(74) Attorney, Agent, or Firm — Potomac Patent Law, PLLC

(57) ABSTRACT

A topical nerve stimulator patch and system are provided comprising a dermal patch; an electrical signal generator associated with the patch; a signal receiver to activate the electrical signal generator; a power source for the electrical signal generator associated with the patch; an electrical signal activation device; and a nerve feedback sensor.

25 Claims, 12 Drawing Sheets

Related U.S. Application Data

(60) Provisional application No. 61/828,981, filed on May 30, 2013.

(51) Int. Cl.
*A61B 5/00* (2006.01)
*A61B 5/04* (2006.01)

(52) U.S. Cl.
CPC .......... *A61N 1/0476* (2013.01); *A61N 1/0492* (2013.01); *A61N 1/36003* (2013.01); *A61N 1/36007* (2013.01); *A61B 5/04001* (2013.01); *A61B 5/4836* (2013.01); *A61N 1/36021* (2013.01)

(58) Field of Classification Search
CPC ... A61B 2562/164; A61B 5/11; A61B 5/4519; A61B 5/6833; A61B 5/00; A61B 5/0484; A61B 5/4041; A61B 5/04; A61B 5/6877
See application file for complete search history.

(56) References Cited

U.S. PATENT DOCUMENTS

| | | |
|---|---|---|
| 4,542,753 A | 9/1985 | Brenman et al. |
| 4,549,556 A | 10/1985 | Tarjan et al. |
| 4,553,549 A | 11/1985 | Pope et al. |
| 4,590,949 A | 5/1986 | Pohndorf |
| 4,614,395 A | 9/1986 | Peers-Trevarton |
| 4,658,835 A | 4/1987 | Pohndorf |
| 4,677,989 A | 7/1987 | Robblee |
| 4,690,144 A | 9/1987 | Rise et al. |
| 4,702,254 A | 10/1987 | Zabara |
| 4,706,682 A | 11/1987 | Stypulkowski et al. |
| 4,717,581 A | 1/1988 | Robblee |
| 4,759,228 A | 7/1988 | Butler et al. |
| 4,800,898 A | 1/1989 | Hess et al. |
| 4,817,628 A | 4/1989 | Zealear et al. |
| 4,881,526 A | 11/1989 | Johnson et al. |
| 4,883,666 A | 11/1989 | Sabel et al. |
| 4,919,148 A | 4/1990 | Muccio |
| 4,940,453 A | 7/1990 | Cadwell |
| 4,959,532 A | 9/1990 | Owechko |
| 5,031,621 A | 7/1991 | Grandjean et al. |
| 5,035,242 A | 7/1991 | Franklin et al. |
| 5,047,005 A | 9/1991 | Cadwell |
| 5,092,332 A | 3/1992 | Lee et al. |
| 5,092,835 A | 3/1992 | Schurig et al. |
| 5,095,905 A | 3/1992 | Klepinski |
| 5,211,657 A | 5/1993 | Yamada et al. |
| 5,265,608 A | 11/1993 | Lee et al. |
| 5,381,801 A | 1/1995 | McShane et al. |
| 5,476,494 A | 12/1995 | Edell et al. |
| 5,501,703 A | 3/1996 | Holsheimer et al. |
| 5,569,307 A | 10/1996 | Schulman et al. |
| 5,575,813 A | 11/1996 | Edell et al. |
| 5,584,869 A | 12/1996 | Heck et al. |
| 5,597,381 A | 1/1997 | Rizzo, III |
| 5,603,726 A | 2/1997 | Schulman et al. |
| 5,609,616 A | 3/1997 | Schulman et al. |
| 5,628,769 A | 5/1997 | Saringer |
| 5,643,330 A | 7/1997 | Holsheimer et al. |
| 5,679,340 A | 10/1997 | Chappel |
| 5,713,922 A | 2/1998 | King |
| 5,738,625 A | 4/1998 | Gluck |
| 5,741,314 A | 4/1998 | Daly et al. |
| 5,795,790 A | 8/1998 | Schinstine et al. |
| 5,824,022 A | 10/1998 | Zilberman et al. |
| 5,830,651 A | 11/1998 | Cauley et al. |
| 5,837,236 A | 11/1998 | Dinsmore |
| 5,853,370 A | 12/1998 | Chance et al. |
| 5,871,534 A | 2/1999 | Messick et al. |
| 5,876,425 A | 3/1999 | Gord et al. |
| 5,891,437 A | 4/1999 | Pietropaolo et al. |
| 5,916,870 A | 6/1999 | Lee et al. |
| 5,921,245 A | 7/1999 | O'Donnell, Jr. |
| 5,922,012 A | 7/1999 | Sakano |
| 5,937,318 A | 8/1999 | Warner, Jr. et al. |
| 5,938,691 A | 8/1999 | Schulman et al. |
| 5,948,428 A | 9/1999 | Lee et al. |
| 5,987,361 A | 11/1999 | Mortimer |
| 5,989,445 A | 11/1999 | Wise et al. |
| 5,992,769 A | 11/1999 | Wise et al. |
| 6,002,960 A | 12/1999 | Sternberger et al. |
| 6,011,018 A | 1/2000 | Crabtree et al. |
| 6,016,449 A | 1/2000 | Fischell et al. |
| 6,058,331 A | 5/2000 | King |
| 6,060,048 A | 5/2000 | Cherksey |
| 6,060,054 A | 5/2000 | Staerz |
| 6,066,084 A | 5/2000 | Edrich et al. |
| 6,067,474 A | 5/2000 | Schulman et al. |
| 6,085,115 A | 7/2000 | Weaver et al. |
| 6,096,537 A | 8/2000 | Chappel |
| 6,119,071 A | 9/2000 | Gorenflo et al. |
| 6,120,538 A | 9/2000 | Rizzo, III et al. |
| 6,140,116 A | 10/2000 | Dinsmore |
| 6,178,349 B1 | 1/2001 | Kieval |
| 6,203,792 B1 | 3/2001 | Filbin |
| 6,204,053 B1 | 3/2001 | Dinsmore |
| 6,258,353 B1 | 7/2001 | Isacson et al. |
| 6,264,950 B1 | 7/2001 | Staerz |
| 6,265,175 B1 | 7/2001 | Gage et al. |
| 6,270,831 B2 | 8/2001 | Kumar et al. |
| 6,277,372 B1 | 8/2001 | Fraser et al. |
| 6,284,245 B1 | 9/2001 | Edge |
| 6,288,527 B1 | 9/2001 | Sugihara et al. |
| 6,294,383 B1 | 9/2001 | Isacson et al. |
| 6,304,784 B1 | 10/2001 | Allee et al. |
| 6,304,787 B1 | 10/2001 | Kuzma et al. |
| 6,359,550 B1 | 3/2002 | Brisebois et al. |
| 6,374,140 B1 | 4/2002 | Rise |
| 6,379,393 B1 | 4/2002 | Mavroidis et al. |
| 6,392,118 B1 | 5/2002 | Hammang et al. |
| 6,392,550 B1 | 5/2002 | Najor |
| 6,393,327 B1 | 5/2002 | Scribner |
| 6,415,186 B1 | 7/2002 | Chim et al. |
| 6,421,232 B2 | 7/2002 | Sallam |
| 6,427,083 B1 | 7/2002 | Owen et al. |
| 6,444,205 B2 | 9/2002 | Dinsmore et al. |
| 6,472,181 B1 | 10/2002 | Mineau-Hanschke |
| 6,510,347 B2 | 1/2003 | Borkan |
| 6,517,833 B2 | 2/2003 | Edge |
| 6,533,732 B1 | 3/2003 | Urmey |
| 6,537,200 B2 | 3/2003 | Leysieffer et al. |
| 6,546,291 B2 | 4/2003 | Merfeld et al. |
| 6,561,975 B1 | 5/2003 | Pool et al. |
| 6,565,503 B2 | 5/2003 | Leysieffer et al. |
| 6,575,894 B2 | 6/2003 | Leysieffer et al. |
| 6,599,695 B2 | 7/2003 | Gage et al. |
| 6,640,118 B2 | 10/2003 | Van Heerden et al. |
| 6,640,121 B1 | 10/2003 | Telischi et al. |
| RE38,323 E | 11/2003 | Sugihara et al. |
| 6,647,297 B2 | 11/2003 | Scribner |
| 6,690,974 B2 | 2/2004 | Archer et al. |
| 6,697,674 B2 | 2/2004 | Leysieffer |
| 6,727,696 B2 | 4/2004 | Kruspe et al. |
| 6,744,367 B1 | 6/2004 | Forster |
| 6,788,976 B2 | 9/2004 | Gesotti |
| 6,795,737 B2 | 9/2004 | Gielen et al. |
| 6,807,445 B2 | 10/2004 | Baumann et al. |
| 6,839,596 B2 | 1/2005 | Nelson et al. |
| 6,850,802 B2 | 2/2005 | Holsheimer |
| 6,879,855 B2 | 4/2005 | Schulman et al. |
| 6,884,122 B2 | 4/2005 | Robinson et al. |
| 6,892,097 B2 | 5/2005 | Holsheimer |
| 6,893,812 B2 | 5/2005 | Woltering et al. |
| 6,894,616 B1 | 5/2005 | Forster |
| 6,902,547 B2 | 6/2005 | Aves et al. |
| 6,931,273 B2 | 8/2005 | Groenewegen et al. |
| 6,949,251 B2 | 9/2005 | Dalal et al. |
| 6,970,745 B2 | 11/2005 | Scribner |
| 6,976,998 B2 | 12/2005 | Rizzo et al. |
| 7,001,608 B2 | 2/2006 | Fishman et al. |
| 7,003,335 B2 | 2/2006 | Briancon |

(56) References Cited

U.S. PATENT DOCUMENTS

| | | |
|---|---|---|
| 7,010,351 B2 | 3/2006 | Firlik et al. |
| 7,027,873 B2 | 4/2006 | Pajunk et al. |
| 7,030,411 B2 | 4/2006 | Krulevitch et al. |
| 7,037,603 B2 | 5/2006 | Lasater |
| 7,047,080 B2 | 5/2006 | Palanker et al. |
| 7,058,455 B2 | 6/2006 | Huie, Jr. et al. |
| 7,079,882 B1 | 7/2006 | Schmidt |
| 7,101,542 B1 | 9/2006 | Vallera et al. |
| 7,106,190 B1 | 9/2006 | Owens |
| 7,107,104 B2 | 9/2006 | Keravel et al. |
| 7,115,071 B1 | 10/2006 | Sunbeck |
| 7,117,034 B2 | 10/2006 | Kronberg |
| 7,120,499 B2 | 10/2006 | Thrope et al. |
| 7,127,301 B1 | 10/2006 | Okandan et al. |
| 7,155,278 B2 | 12/2006 | King et al. |
| 7,167,750 B2 | 1/2007 | Knudson et al. |
| 7,174,223 B2 | 2/2007 | Dalton et al. |
| 7,181,288 B1 | 2/2007 | Rezai et al. |
| 7,191,018 B2 | 3/2007 | Gielen et al. |
| 7,193,414 B2 | 3/2007 | Kruspe et al. |
| 7,206,632 B2 | 4/2007 | King |
| 7,209,787 B2 | 4/2007 | DiLorenzo |
| 7,218,216 B1 | 5/2007 | Uehran |
| 7,218,964 B2 | 5/2007 | Hill et al. |
| 7,228,178 B2 | 6/2007 | Carroll et al. |
| 7,228,727 B2 | 6/2007 | Discenzo |
| 7,239,918 B2 | 7/2007 | Strother et al. |
| 7,249,998 B2 | 7/2007 | van Esbroeck et al. |
| 7,283,867 B2 | 10/2007 | Strother et al. |
| 7,297,420 B2 | 11/2007 | Jiang |
| 7,299,034 B2 | 11/2007 | Kates |
| 7,308,303 B2 | 12/2007 | Whitehurst et al. |
| 7,308,317 B1 | 12/2007 | Okandan et al. |
| 7,333,851 B2 | 2/2008 | Echauz et al. |
| 7,337,004 B2 | 2/2008 | Classen et al. |
| 7,349,169 B2 | 3/2008 | Lee et al. |
| RE40,209 E | 4/2008 | Sugihara et al. |
| 7,376,467 B2 | 5/2008 | Thrope et al. |
| 7,384,145 B2 | 6/2008 | Hetling et al. |
| 7,392,093 B2 | 6/2008 | Khan |
| 7,398,255 B2 | 7/2008 | Lauer et al. |
| 7,415,309 B2 | 8/2008 | McIntyre |
| 7,420,760 B2 | 9/2008 | Zhang et al. |
| 7,422,564 B2 | 9/2008 | Parsons et al. |
| 7,435,443 B2 | 10/2008 | Jiang |
| 7,435,585 B2 | 10/2008 | Tykocinski et al. |
| 7,437,193 B2 | 10/2008 | Parramon et al. |
| 7,437,196 B2 | 10/2008 | Wyler et al. |
| 7,483,747 B2 | 1/2009 | Gliner et al. |
| 7,499,745 B2 | 3/2009 | Littrup et al. |
| 7,499,748 B2 | 3/2009 | Moffitt et al. |
| 7,502,652 B2 | 3/2009 | Gaunt et al. |
| 7,519,419 B2 | 4/2009 | Jiang et al. |
| 7,529,582 B1 | 5/2009 | DiLorenzo |
| 7,553,307 B2 | 6/2009 | Bleich et al. |
| 7,555,343 B2 | 6/2009 | Bleich |
| 7,561,919 B2 | 7/2009 | Shalev et al. |
| 7,565,199 B2 | 7/2009 | Sheffield et al. |
| 7,565,200 B2 | 7/2009 | Wyler et al. |
| 7,571,002 B2 | 8/2009 | Thrope et al. |
| 7,571,006 B2 | 8/2009 | Gordon et al. |
| 7,578,819 B2 | 8/2009 | Bleich et al. |
| 7,584,004 B2 | 9/2009 | Caparso et al. |
| 7,587,238 B2 | 9/2009 | Moffitt et al. |
| 7,598,031 B2 | 10/2009 | Liew |
| 7,599,737 B2 | 10/2009 | Yomtov et al. |
| 7,620,456 B2 | 11/2009 | Gliner et al. |
| 7,622,303 B2 | 11/2009 | Soykan et al. |
| 7,636,597 B2 | 12/2009 | Gross et al. |
| 7,657,308 B2 | 2/2010 | Miles et al. |
| 7,658,707 B2 | 2/2010 | Topolev |
| 7,662,558 B2 | 2/2010 | Liew |
| 7,676,274 B2 | 3/2010 | Hung et al. |
| 7,680,526 B2 | 3/2010 | McIntyre et al. |
| 7,684,866 B2 | 3/2010 | Fowler et al. |
| D613,868 S | 4/2010 | Lhuillery et al. |
| 7,699,768 B2 | 4/2010 | Kishawi et al. |
| 7,704,740 B2 | 4/2010 | Schindler et al. |
| 7,706,888 B2 | 4/2010 | Jolly |
| 7,706,893 B2 | 4/2010 | Hung et al. |
| 7,711,416 B1 | 5/2010 | Akkin et al. |
| 7,715,919 B2 | 5/2010 | Osorio et al. |
| 7,715,924 B2 | 5/2010 | Rezai et al. |
| 7,725,196 B2 | 5/2010 | Machado et al. |
| 7,732,407 B2 | 6/2010 | Hunter |
| 7,738,968 B2 | 6/2010 | Bleich |
| 7,738,969 B2 | 6/2010 | Bleich |
| 7,740,631 B2 | 6/2010 | Bleich et al. |
| 7,747,318 B2 | 6/2010 | John et al. |
| 7,756,583 B2 | 7/2010 | Demarais et al. |
| 7,756,584 B2 | 7/2010 | Sheffield et al. |
| 7,769,462 B2 | 8/2010 | Meadows et al. |
| 7,769,470 B1 | 8/2010 | Rezai et al. |
| 7,798,982 B2 | 9/2010 | Zets et al. |
| 7,799,021 B2 | 9/2010 | Leung et al. |
| 7,801,603 B2 | 9/2010 | Westlund et al. |
| 7,813,809 B2 | 10/2010 | Strother et al. |
| 7,819,801 B2 | 10/2010 | Miles et al. |
| 7,819,869 B2 | 10/2010 | Godara et al. |
| 7,831,305 B2 | 11/2010 | Gliner |
| 7,844,340 B2 | 11/2010 | Pawlowicz, III |
| 7,877,136 B1 | 1/2011 | Moffitt et al. |
| 7,892,180 B2 | 2/2011 | Epley |
| 7,894,911 B2 | 2/2011 | Greenberg et al. |
| 7,894,914 B2 | 2/2011 | Stahmann et al. |
| 7,899,542 B2 | 3/2011 | Cowan et al. |
| 7,914,842 B1 | 3/2011 | Greenberg et al. |
| 7,917,231 B2 | 3/2011 | Farah et al. |
| 7,918,802 B2 | 4/2011 | Urmey |
| 7,943,632 B2 | 5/2011 | Katzman et al. |
| 7,945,330 B2 | 5/2011 | Gliner et al. |
| 7,947,448 B2 | 5/2011 | Couillard-Despres et al. |
| RE42,449 E | 6/2011 | Forster |
| 7,959,577 B2 | 6/2011 | Schmitz et al. |
| 7,963,915 B2 | 6/2011 | Bleich |
| 7,967,751 B2 | 6/2011 | Goscha et al. |
| 7,974,689 B2 | 7/2011 | Volpe et al. |
| 7,981,144 B2 | 7/2011 | Geist et al. |
| 7,988,688 B2 | 8/2011 | Webb et al. |
| 7,991,475 B1 | 8/2011 | Tang et al. |
| 7,991,480 B2 | 8/2011 | Stahmann et al. |
| 7,992,521 B2 | 8/2011 | Bocquier |
| 8,000,782 B2 | 8/2011 | Gharib et al. |
| 8,000,796 B2 | 8/2011 | Tass et al. |
| 8,000,804 B1 | 8/2011 | Wessendorf et al. |
| 8,010,202 B2 | 8/2011 | Shah et al. |
| 8,014,868 B2 | 9/2011 | Greenberg et al. |
| 8,014,878 B2 | 9/2011 | Greenberg et al. |
| 8,025,632 B2 | 9/2011 | Einarsson |
| 8,027,716 B2 | 9/2011 | Gharib et al. |
| 8,033,996 B2 | 10/2011 | Behar |
| 8,060,210 B1 | 11/2011 | Carroll |
| 8,065,012 B2 | 11/2011 | Firlik et al. |
| 8,067,173 B2 | 11/2011 | Liew |
| 8,073,526 B2 | 12/2011 | Graham et al. |
| 8,073,546 B2 | 12/2011 | Sheffield et al. |
| 8,075,556 B2 | 12/2011 | Betts |
| 8,078,252 B2 | 12/2011 | Kipke et al. |
| 8,090,446 B2 | 1/2012 | Fowler et al. |
| 8,092,398 B2 | 1/2012 | Weinberg et al. |
| 8,095,209 B2 | 1/2012 | Flaherty |
| 8,101,358 B2 | 1/2012 | Liew |
| 8,110,358 B2 | 2/2012 | Liew |
| 8,114,019 B2 | 2/2012 | Miles et al. |
| 8,114,597 B2 | 2/2012 | Liew |
| 8,116,875 B2 | 2/2012 | Osypka et al. |
| 8,126,562 B2 | 2/2012 | Fowler et al. |
| 8,131,376 B1 | 3/2012 | Faraji et al. |
| 8,133,674 B2 | 3/2012 | Liew |
| 8,133,675 B2 | 3/2012 | Liew |
| 8,135,472 B2 | 3/2012 | Fowler et al. |
| 8,137,258 B1 | 3/2012 | Dennis et al. |
| 8,137,284 B2 | 3/2012 | Miles et al. |
| 8,140,152 B2 | 3/2012 | John et al. |

(56) References Cited

U.S. PATENT DOCUMENTS

| | | |
|---|---|---|
| 8,140,162 B1 | 3/2012 | Jiang et al. |
| 8,140,170 B2 | 3/2012 | Rezai et al. |
| 8,148,072 B2 | 4/2012 | Liew |
| 8,155,757 B1 | 4/2012 | Neisz et al. |
| 8,160,713 B2 | 4/2012 | Greenberg et al. |
| 8,162,846 B2 | 4/2012 | Epley |
| 8,165,685 B1 | 4/2012 | Knutson et al. |
| 8,170,676 B2 | 5/2012 | Greenberg et al. |
| 8,174,371 B2 | 5/2012 | Schwieger |
| 8,180,453 B2 | 5/2012 | Greenberg et al. |
| 8,180,460 B2 | 5/2012 | Nevsmith et al. |
| 8,192,357 B2 | 6/2012 | Miles et al. |
| 8,195,300 B2 | 6/2012 | Gliner et al. |
| 8,195,307 B2 | 6/2012 | Vilims |
| 8,200,338 B2 | 6/2012 | Grennberg et al. |
| 8,215,773 B2 | 7/2012 | Gibson-Horn et al. |
| 8,216,135 B2 | 7/2012 | Goscha et al. |
| 8,226,661 B2 | 7/2012 | Balling et al. |
| 8,228,202 B2 | 7/2012 | Buchner et al. |
| 8,239,036 B2 | 8/2012 | Shah et al. |
| 8,255,044 B2 | 8/2012 | Miles et al. |
| 8,257,922 B2 | 9/2012 | Liew |
| 8,260,428 B2 | 9/2012 | Fink et al. |
| 8,260,439 B2 | 9/2012 | DiUbaldi et al. |
| 8,280,516 B2 | 10/2012 | Graupe |
| 8,301,266 B1 | 10/2012 | Zilberman et al. |
| 8,303,516 B2 | 11/2012 | Schmitz et al. |
| 8,308,665 B2 | 11/2012 | Harry et al. |
| 8,313,443 B2 | 11/2012 | Tom |
| 8,323,320 B2 | 12/2012 | Lowry et al. |
| 8,328,354 B2 | 12/2012 | Li et al. |
| 8,332,037 B2 | 12/2012 | Imran |
| 8,332,044 B2 | 12/2012 | McIntyre |
| 8,346,367 B2 | 1/2013 | Carroll |
| 8,352,022 B2 | 1/2013 | Akkin et al. |
| 8,359,083 B2 | 1/2013 | Clark et al. |
| 8,364,257 B2 | 1/2013 | Van Den Eerenbeemd et al. |
| 8,364,258 B2 | 1/2013 | Della Rocca et al. |
| 8,374,698 B2 | 2/2013 | Ok et al. |
| 8,374,701 B2 | 2/2013 | Hyde et al. |
| 8,382,656 B1 | 2/2013 | Brown |
| 8,386,032 B2 | 2/2013 | Bachinski et al. |
| 8,386,053 B2 | 2/2013 | Kornet |
| 8,388,678 B2 | 3/2013 | Singhal et al. |
| 8,391,970 B2 | 3/2013 | Tracey et al. |
| 8,391,986 B2 | 3/2013 | Graupe et al. |
| 8,391,987 B2 | 3/2013 | Faraji et al. |
| 8,396,556 B2 | 3/2013 | Libbus et al. |
| 8,403,841 B2 | 3/2013 | Miles et al. |
| 8,406,886 B2 | 3/2013 | Gaunt et al. |
| 8,412,328 B2 | 4/2013 | Whelan et al. |
| 8,412,335 B2 | 4/2013 | Gliner et al. |
| 8,417,345 B2 | 4/2013 | Machado et al. |
| 8,419,653 B2 | 4/2013 | Bleich et al. |
| 8,428,732 B2 | 4/2013 | Nishida et al. |
| 8,428,738 B2 | 4/2013 | Valencia |
| 8,428,739 B2 | 4/2013 | Ahuja et al. |
| 8,430,882 B2 | 4/2013 | Lowry et al. |
| 8,444,640 B2 | 5/2013 | Demarais et al. |
| 8,457,764 B2 | 6/2013 | Ramachandran et al. |
| 8,460,167 B2 | 6/2013 | Chornenky et al. |
| 8,463,383 B2 | 6/2013 | Sakai et al. |
| 8,473,048 B2 | 6/2013 | Greenberg et al. |
| 8,494,640 B2 | 7/2013 | Peterson et al. |
| 8,494,642 B2 | 7/2013 | Cowan et al. |
| 8,498,717 B2 | 7/2013 | Lee et al. |
| 8,498,720 B2 | 7/2013 | Pellinen et al. |
| 8,506,613 B2 | 8/2013 | Webb et al. |
| 8,509,903 B2 | 8/2013 | York et al. |
| 8,512,235 B2 | 8/2013 | Miles et al. |
| 8,515,533 B2 | 8/2013 | Rofougaran et al. |
| 8,515,543 B2 | 8/2013 | Greenberg et al. |
| 8,517,961 B2 | 8/2013 | Imran et al. |
| 8,524,311 B1 | 9/2013 | Greenberg et al. |
| 8,532,776 B2 | 9/2013 | Greenberg et al. |
| 8,538,537 B2 | 9/2013 | Hulvershorn et al. |
| 8,543,210 B2 | 9/2013 | Sharma |
| 8,548,600 B2 | 10/2013 | Deem et al. |
| 8,554,328 B2 | 10/2013 | Faraji et al. |
| 8,554,337 B2 | 10/2013 | Barolat |
| 8,556,838 B2 | 10/2013 | Moutray |
| 8,560,041 B2 | 10/2013 | Flaherty et al. |
| 8,562,521 B2 | 10/2013 | Miles et al. |
| 8,565,894 B2 | 10/2013 | Vetter et al. |
| 8,568,331 B2 | 10/2013 | Bertagnoli et al. |
| 8,571,665 B2 | 10/2013 | Moffitt et al. |
| 8,579,837 B1 | 11/2013 | Makower et al. |
| 8,583,238 B1 | 11/2013 | Heldman et al. |
| 8,588,918 B2 | 11/2013 | Bighetti |
| 8,594,798 B2 | 11/2013 | Osorio et al. |
| 8,600,514 B1 | 12/2013 | Carroll |
| 8,608,664 B2 | 12/2013 | Kunitake et al. |
| 8,612,002 B2 | 12/2013 | Faltys et al. |
| 8,615,308 B2 | 12/2013 | Hung et al. |
| 8,617,808 B2 | 12/2013 | Braesch-Andersen et al. |
| 8,626,265 B2 | 1/2014 | Hempel et al. |
| 8,626,305 B2 | 1/2014 | Nielsen et al. |
| 8,628,469 B2 | 1/2014 | Miles et al. |
| 8,634,930 B2 | 1/2014 | Dalal et al. |
| 8,634,932 B1 | 1/2014 | Ye et al. |
| 8,639,344 B2 | 1/2014 | Greenberg et al. |
| 8,644,900 B2 | 2/2014 | Balberg et al. |
| 8,644,937 B2 | 2/2014 | Greenberg et al. |
| 8,644,938 B2 | 2/2014 | Craggs |
| 8,647,346 B2 | 2/2014 | Bleich et al. |
| 8,649,845 B2 | 2/2014 | McIntyre et al. |
| 8,649,868 B2 | 2/2014 | Greenberg et al. |
| 8,652,129 B2 | 2/2014 | Wu et al. |
| 8,652,187 B2 | 2/2014 | Wells et al. |
| 8,655,455 B2 | 2/2014 | Mann et al. |
| 8,660,655 B2 | 2/2014 | Peterson et al. |
| 8,666,500 B2 | 3/2014 | Greenberg et al. |
| 8,667,971 B2 | 3/2014 | Makkar et al. |
| 8,667,972 B2 | 3/2014 | Makkar et al. |
| 8,669,058 B2 | 3/2014 | Liew |
| 8,670,837 B2 | 3/2014 | Daneshvar et al. |
| 8,674,838 B2 | 3/2014 | Konishi et al. |
| 8,676,274 B2 | 3/2014 | Li |
| 8,682,443 B2 | 3/2014 | Faraji et al. |
| 8,698,637 B2 | 4/2014 | Raichman |
| 8,702,685 B2 | 4/2014 | Schwartz et al. |
| 8,706,241 B2 | 4/2014 | Firlik et al. |
| 8,708,899 B2 | 4/2014 | Miles et al. |
| 8,712,517 B2 | 4/2014 | Jolly |
| 8,712,538 B2 | 4/2014 | Greenberg et al. |
| 8,712,549 B2 | 4/2014 | Zdeblick et al. |
| 8,721,637 B2 | 5/2014 | Zarins et al. |
| 8,725,251 B2 | 5/2014 | Della Rocca et al. |
| 8,734,339 B2 | 5/2014 | Rao et al. |
| 8,740,783 B2 | 6/2014 | Gharib et al. |
| 8,740,896 B2 | 6/2014 | Zarins et al. |
| 8,744,570 B2 | 6/2014 | Lee et al. |
| 8,750,957 B2 | 6/2014 | Tang et al. |
| 8,753,271 B1 | 6/2014 | Miles et al. |
| 8,755,896 B2 | 6/2014 | Humayun et al. |
| 8,761,889 B2 | 6/2014 | Wingeier et al. |
| 8,774,922 B2 | 7/2014 | Zarins et al. |
| 8,774,937 B2 | 7/2014 | Mercanzini et al. |
| 8,777,942 B2 | 7/2014 | Wu et al. |
| 8,781,603 B2 | 7/2014 | Ye et al. |
| 8,784,461 B2 | 7/2014 | Webb et al. |
| 8,788,064 B2 | 7/2014 | Mercanzini et al. |
| 8,788,065 B2 | 7/2014 | Rezai et al. |
| 8,790,338 B2 | 7/2014 | Asirvatham et al. |
| 8,798,756 B2 | 8/2014 | McClure et al. |
| 8,801,589 B2 | 8/2014 | Peterchev et al. |
| 8,805,467 B2 | 8/2014 | Yobas et al. |
| 8,805,517 B2 | 8/2014 | Radivojevic et al. |
| 8,805,521 B2 | 8/2014 | Carroll |
| 8,821,396 B1 | 9/2014 | Miles et al. |
| 8,831,750 B2 | 9/2014 | Ramachandran et al. |
| 8,834,545 B2 | 9/2014 | Stafford et al. |
| 8,835,163 B2 | 9/2014 | Zhao et al. |
| 8,843,201 B1 | 9/2014 | Heldman et al. |

(56) References Cited

U.S. PATENT DOCUMENTS

| | | |
|---|---|---|
| 8,843,204 B2 | 9/2014 | Garnham et al. |
| 8,843,210 B2 | 9/2014 | Simon et al. |
| 8,849,412 B2 | 9/2014 | Perryman et al. |
| 8,855,767 B2 | 10/2014 | Faltys et al. |
| 8,862,236 B2 | 10/2014 | Wolpaw et al. |
| 8,864,665 B2 | 10/2014 | Rotondo et al. |
| 8,864,759 B2 | 10/2014 | Godara et al. |
| 8,866,621 B2 | 10/2014 | Wolfe et al. |
| 8,868,164 B2 | 10/2014 | Kabakov et al. |
| 8,868,172 B2 | 10/2014 | Leyde et al. |
| 8,868,216 B2 | 10/2014 | Dunagan |
| 8,870,857 B2 | 10/2014 | Seymour et al. |
| 8,874,216 B2 | 10/2014 | Kim et al. |
| 8,874,239 B2 | 10/2014 | Greenberg et al. |
| 8,880,189 B2 | 11/2014 | Lipani |
| 8,886,324 B2 | 11/2014 | Beuter et al. |
| 8,888,773 B2 | 11/2014 | Chang et al. |
| 8,892,215 B2 | 11/2014 | Lipani |
| 8,903,494 B2 | 12/2014 | Goldwasser et al. |
| 8,903,501 B2 | 12/2014 | Perryman |
| 8,909,343 B2 | 12/2014 | Towe |
| 8,909,344 B2 | 12/2014 | Arle et al. |
| 8,909,345 B1 | 12/2014 | Danilov et al. |
| 8,912,149 B1 | 12/2014 | Rawat et al. |
| 8,915,846 B2 | 12/2014 | Miles et al. |
| 8,915,867 B2 | 12/2014 | Imran et al. |
| 8,918,178 B2 | 12/2014 | Simon et al. |
| 8,921,473 B1 | 12/2014 | Hyman |
| 8,926,959 B2 | 1/2015 | Deisseroth et al. |
| 8,929,990 B2 | 1/2015 | Moffitt et al. |
| 8,932,196 B2 | 1/2015 | Chornenky et al. |
| 8,942,797 B2 | 1/2015 | Bartol et al. |
| 8,942,812 B2 | 1/2015 | MacHado et al. |
| 8,942,821 B2 | 1/2015 | Barolat |
| 8,945,004 B2 | 2/2015 | Miles et al. |
| 8,945,216 B2 | 2/2015 | Parker et al. |
| 8,948,884 B2 | 2/2015 | Ramachandran et al. |
| 8,951,193 B2 | 2/2015 | Ong et al. |
| 8,954,144 B2 | 2/2015 | Anderson et al. |
| 8,954,150 B2 | 2/2015 | Swanson et al. |
| 8,954,157 B2 | 2/2015 | Faraji et al. |
| 8,954,167 B2 | 2/2015 | Zarembo et al. |
| 8,956,387 B2 | 2/2015 | Naghavi et al. |
| 8,958,862 B2 | 2/2015 | Hetke et al. |
| 8,958,883 B2 | 2/2015 | Mueller et al. |
| 8,958,890 B2 | 2/2015 | Kipke et al. |
| 8,965,513 B2 | 2/2015 | Wingeier et al. |
| 8,969,532 B2 | 3/2015 | DeFrees et al. |
| 8,972,026 B2 | 3/2015 | Kipke et al. |
| 8,974,402 B2 | 3/2015 | Oddsson et al. |
| 8,983,593 B2 | 3/2015 | Bartol et al. |
| 8,983,601 B2 | 3/2015 | Fukamachi et al. |
| 8,983,628 B2 | 3/2015 | Simon et al. |
| 8,983,629 B2 | 3/2015 | Simon et al. |
| 8,985,057 B2 | 3/2015 | Woodward |
| 8,986,294 B2 | 3/2015 | Demarais et al. |
| 8,992,522 B2 | 3/2015 | Pellegrino et al. |
| 8,996,131 B1 | 3/2015 | Owen et al. |
| 8,998,894 B2 | 4/2015 | Mauch et al. |
| 9,002,458 B2 | 4/2015 | Pal et al. |
| 9,002,477 B2 | 4/2015 | Burnett |
| 9,005,191 B2 | 4/2015 | Azamian et al. |
| 9,008,784 B2 | 4/2015 | Chan et al. |
| 9,014,810 B2 | 4/2015 | Sauter-Starace et al. |
| 9,014,811 B2 | 4/2015 | Pal et al. |
| 9,014,823 B2 | 4/2015 | Simon et al. |
| 9,019,106 B2 | 4/2015 | Alameh et al. |
| 9,020,598 B2 | 4/2015 | Simon et al. |
| 9,020,612 B1 | 4/2015 | Danilov et al. |
| 9,023,037 B2 | 5/2015 | Zarins et al. |
| 9,034,640 B2 | 5/2015 | Matos et al. |
| 9,037,268 B2 | 5/2015 | Knight |
| 9,042,958 B2 | 5/2015 | Karmarkar et al. |
| 9,043,001 B2 | 5/2015 | Simon et al. |
| 9,044,596 B2 | 6/2015 | Mahadevan-Jansen et al. |
| 9,044,611 B2 | 6/2015 | Zhao et al. |
| 9,056,197 B2 | 6/2015 | Kishawi et al. |
| 9,061,097 B2 | 6/2015 | Holt et al. |
| 9,061,134 B2 | 6/2015 | Askin, III et al. |
| 9,061,135 B1 | 6/2015 | Keller et al. |
| 9,072,886 B2 | 7/2015 | Gaunt et al. |
| 9,072,889 B2 | 7/2015 | Guarraia et al. |
| 9,072,891 B1 | 7/2015 | Rao |
| 9,084,550 B1 | 7/2015 | Bartol et al. |
| 9,084,610 B2 | 7/2015 | Goshgarian et al. |
| 9,084,895 B2 | 7/2015 | Greenberg et al. |
| 9,084,900 B2 | 7/2015 | Hershey et al. |
| 9,089,341 B2 | 7/2015 | Chomas et al. |
| 9,089,687 B2 | 7/2015 | Lee, II et al. |
| 9,089,691 B2 | 7/2015 | Libbus et al. |
| 9,095,267 B2 | 8/2015 | Halpern et al. |
| 9,095,320 B2 | 8/2015 | Littrup et al. |
| 9,095,538 B2 | 8/2015 | Yu et al. |
| 9,101,279 B2 | 8/2015 | Ritchey et al. |
| 9,113,912 B1 | 8/2015 | Mehta et al. |
| 9,114,261 B2 | 8/2015 | Yonce |
| 9,119,628 B1 | 9/2015 | Mehta et al. |
| 9,119,964 B2 | 9/2015 | Marnfeldt |
| 9,126,197 B2 | 9/2015 | Orwar et al. |
| 9,132,058 B2 | 9/2015 | Imboden et al. |
| 9,138,579 B2 | 9/2015 | Wolpaw et al. |
| 9,144,677 B2 | 9/2015 | Garnham et al. |
| 9,155,887 B2 | 10/2015 | Miller, III et al. |
| 9,158,890 B2 | 10/2015 | Meredith et al. |
| 9,162,010 B2 | 10/2015 | Lenarz et al. |
| 9,162,064 B2 | 10/2015 | Faltys et al. |
| 9,173,585 B2 | 11/2015 | Tsampazis et al. |
| 9,179,850 B2 | 11/2015 | Wingeier et al. |
| 9,179,875 B2 | 11/2015 | Hua |
| 9,189,613 B1 | 11/2015 | Tuthill et al. |
| 9,192,757 B2 | 11/2015 | Seymour |
| 9,192,767 B2 | 11/2015 | Mercanzini et al. |
| 9,199,089 B2 | 12/2015 | Perryman et al. |
| 9,205,275 B2 | 12/2015 | Pan et al. |
| 9,220,897 B2 | 12/2015 | Perryman et al. |
| 9,220,899 B2 | 12/2015 | Cattaneo et al. |
| 9,220,900 B2 | 12/2015 | Libbus et al. |
| 9,221,177 B2 | 12/2015 | Herr et al. |
| 9,227,051 B1 | 1/2016 | Fisk et al. |
| 9,227,056 B1 | 1/2016 | Heldman et al. |
| 9,254,382 B2 | 2/2016 | Ahmad et al. |
| 9,895,546 B2 | 2/2018 | Jiang et al. |
| 2001/0034477 A1 | 10/2001 | Mansfield et al. |
| 2001/0055776 A1 | 12/2001 | Greenwalt |
| 2002/0009461 A1 | 1/2002 | Isacson et al. |
| 2002/0031497 A1 | 3/2002 | Fraser et al. |
| 2002/0034819 A1 | 3/2002 | Smith et al. |
| 2002/0055779 A1 | 5/2002 | Andrews |
| 2002/0090722 A1 | 7/2002 | Dominko et al. |
| 2002/0136705 A1 | 9/2002 | Dinsmore |
| 2002/0176849 A1 | 11/2002 | Slepian |
| 2003/0002297 A1 | 1/2003 | Nemtsev |
| 2003/0004547 A1 | 1/2003 | Owen et al. |
| 2003/0049328 A1 | 3/2003 | Dalal et al. |
| 2003/0088274 A1 | 5/2003 | Gliner et al. |
| 2003/0097161 A1 | 5/2003 | Firlik et al. |
| 2003/0100367 A1 | 5/2003 | Cooke |
| 2003/0104993 A1 | 6/2003 | Rueger et al. |
| 2003/0109901 A1 | 6/2003 | Greatbatch |
| 2003/0125786 A1 | 7/2003 | Gliner et al. |
| 2003/0149450 A1 | 8/2003 | Mayberg |
| 2003/0157712 A1 | 8/2003 | Daniel et al. |
| 2003/0195441 A1 | 10/2003 | Firouzgar |
| 2003/0198664 A1 | 10/2003 | Sullivan et al. |
| 2003/0232055 A1 | 12/2003 | Medzhitov |
| 2004/0005291 A1 | 1/2004 | Rogers et al. |
| 2004/0014662 A1 | 1/2004 | Lindquist et al. |
| 2004/0028613 A1 | 2/2004 | Quay |
| 2004/0030365 A1 | 2/2004 | Rubin |
| 2004/0038888 A1 | 2/2004 | Mercer et al. |
| 2004/0048279 A1 | 3/2004 | Olek et al. |
| 2004/0048373 A1 | 3/2004 | Gage et al. |
| 2004/0049134 A1 | 3/2004 | Tosaya et al. |
| 2004/0054300 A1 | 3/2004 | Hung et al. |

(56) References Cited

U.S. PATENT DOCUMENTS

| | | |
|---|---|---|
| 2004/0062755 A1 | 4/2004 | Smith et al. |
| 2004/0064052 A1 | 4/2004 | Chance et al. |
| 2004/0081652 A1 | 4/2004 | Zack et al. |
| 2004/0093093 A1 | 5/2004 | Andrews |
| 2004/0097401 A1 | 5/2004 | Datta |
| 2004/0097839 A1 | 5/2004 | Epley |
| 2004/0102525 A1 | 5/2004 | Kozachuk |
| 2004/0106966 A1 | 6/2004 | Scribner et al. |
| 2004/0121464 A1 | 6/2004 | Rathjen et al. |
| 2004/0143170 A1 | 7/2004 | DuRousseau |
| 2004/0147975 A1 | 7/2004 | Popovic et al. |
| 2004/0156826 A1 | 8/2004 | Dangond et al. |
| 2004/0162583 A1 | 8/2004 | Bingham et al. |
| 2004/0172100 A1 | 9/2004 | Humayun et al. |
| 2004/0172102 A1 | 9/2004 | Leysieffer |
| 2004/0185557 A1 | 9/2004 | Smith et al. |
| 2004/0199235 A1 | 10/2004 | Younis |
| 2004/0212504 A1 | 10/2004 | Forcier et al. |
| 2004/0219184 A1 | 11/2004 | Brown et al. |
| 2004/0228831 A1 | 11/2004 | Belinka et al. |
| 2004/0229702 A1 | 11/2004 | Cooke |
| 2004/0230226 A1 | 11/2004 | Bingham et al. |
| 2004/0243021 A1 | 12/2004 | Murphy et al. |
| 2005/0003998 A1 | 1/2005 | Bertilsson et al. |
| 2005/0015133 A1 | 1/2005 | Ibrahim et al. |
| 2005/0020519 A1 | 1/2005 | Albiston et al. |
| 2005/0020945 A1 | 1/2005 | Tosaya et al. |
| 2005/0038473 A1 | 2/2005 | Tamarkin et al. |
| 2005/0054096 A1 | 3/2005 | Piniella |
| 2005/0054907 A1 | 3/2005 | Page et al. |
| 2005/0070819 A1 | 3/2005 | Poux et al. |
| 2005/0073649 A1 | 4/2005 | Spector |
| 2005/0107859 A1 | 5/2005 | Daglow et al. |
| 2005/0125044 A1 | 6/2005 | Tracey |
| 2005/0165323 A1 | 7/2005 | Montgomery et al. |
| 2005/0203366 A1 | 9/2005 | Donoghue et al. |
| 2005/0203601 A1 | 9/2005 | Palanker et al. |
| 2005/0222631 A1 | 10/2005 | Dalal et al. |
| 2005/0226852 A1 | 10/2005 | Toda et al. |
| 2005/0234370 A1 | 10/2005 | Beal et al. |
| 2005/0267552 A1 | 12/2005 | Conquergood et al. |
| 2005/0272097 A1 | 12/2005 | Calenoff |
| 2005/0273890 A1 | 12/2005 | Flaherty et al. |
| 2005/0277918 A1 | 12/2005 | Shah et al. |
| 2006/0034767 A1 | 2/2006 | Lum et al. |
| 2006/0047326 A1 | 3/2006 | Wheeler |
| 2006/0049950 A1 | 3/2006 | Lockhart |
| 2006/0049957 A1 | 3/2006 | Surgenor et al. |
| 2006/0058627 A1 | 3/2006 | Flaherty et al. |
| 2006/0118035 A1 | 6/2006 | Lasater |
| 2006/0122458 A1 | 6/2006 | Bleich |
| 2006/0122529 A1 | 6/2006 | Tsau |
| 2006/0122864 A1 | 6/2006 | Gottesman et al. |
| 2006/0140930 A1 | 6/2006 | Rodriguez et al. |
| 2006/0149345 A1 | 7/2006 | Boggs et al. |
| 2006/0161225 A1 | 7/2006 | Sormann et al. |
| 2006/0167498 A1 | 7/2006 | DiLorenzo |
| 2006/0167564 A1 | 7/2006 | Flaherty et al. |
| 2006/0171933 A1 | 8/2006 | Short |
| 2006/0184219 A1 | 8/2006 | Pajunk et al. |
| 2006/0190056 A1 | 8/2006 | Fowler et al. |
| 2006/0195146 A1 | 8/2006 | Tracey et al. |
| 2006/0195153 A1 | 8/2006 | Diubaldi et al. |
| 2006/0206167 A1 | 9/2006 | Flaherty et al. |
| 2006/0206178 A1 | 9/2006 | Kim |
| 2006/0234376 A1 | 10/2006 | Mistry et al. |
| 2006/0263336 A1 | 11/2006 | Caplan |
| 2006/0265037 A1 | 11/2006 | Kuzma |
| 2006/0281130 A1 | 12/2006 | Bock et al. |
| 2007/0005106 A1 | 1/2007 | Adducci |
| 2007/0021803 A1 | 1/2007 | Deem et al. |
| 2007/0043591 A1 | 2/2007 | Meretei et al. |
| 2007/0049814 A1 | 3/2007 | Muccio |
| 2007/0049842 A1 | 3/2007 | Hill et al. |
| 2007/0067004 A1 | 3/2007 | Boveja et al. |
| 2007/0073361 A1 | 3/2007 | Goren et al. |
| 2007/0088335 A1 | 4/2007 | Jolly |
| 2007/0100393 A1 | 5/2007 | Whitehurst et al. |
| 2007/0102009 A1 | 5/2007 | Wong et al. |
| 2007/0107071 A1 | 5/2007 | Couillard-Despres |
| 2007/0123778 A1 | 5/2007 | Kantorovich |
| 2007/0129769 A1 | 6/2007 | Bourget et al. |
| 2007/0134657 A1 | 6/2007 | Poznansky et al. |
| 2007/0135846 A1 | 6/2007 | Knudson et al. |
| 2007/0165322 A1 | 7/2007 | Strom et al. |
| 2007/0173893 A1 | 7/2007 | Pitts |
| 2007/0173903 A1 | 7/2007 | Goren et al. |
| 2007/0179558 A1 | 8/2007 | Gliner et al. |
| 2007/0180542 A1 | 8/2007 | Brinster et al. |
| 2007/0192881 A1 | 8/2007 | Brinster et al. |
| 2007/0203533 A1 | 8/2007 | Goren et al. |
| 2007/0208385 A1 | 9/2007 | Carroll et al. |
| 2007/0219074 A1 | 9/2007 | Pride |
| 2007/0239211 A1 | 10/2007 | Lorincz et al. |
| 2007/0249952 A1 | 10/2007 | Rubin et al. |
| 2007/0276449 A1 | 11/2007 | Gunter et al. |
| 2007/0282396 A1 | 12/2007 | Overstreet et al. |
| 2007/0287613 A1 | 12/2007 | Adducci |
| 2007/0293893 A1 | 12/2007 | Stolen et al. |
| 2007/0299483 A1 | 12/2007 | Strother et al. |
| 2008/0002276 A1 | 1/2008 | Strom et al. |
| 2008/0033520 A1 | 2/2008 | Jolly |
| 2008/0040951 A1 | 2/2008 | Kates |
| 2008/0057028 A1 | 3/2008 | Alitalo et al. |
| 2008/0064946 A1 | 3/2008 | Greenberg et al. |
| 2008/0071321 A1 | 3/2008 | Boggs et al. |
| 2008/0074794 A1 | 3/2008 | Lee et al. |
| 2008/0077192 A1 | 3/2008 | Harry et al. |
| 2008/0095747 A1 | 4/2008 | Rutishauser et al. |
| 2008/0097530 A1 | 4/2008 | Muccio et al. |
| 2008/0120029 A1 | 5/2008 | Zelek et al. |
| 2008/0125870 A1 | 5/2008 | Carmichael et al. |
| 2008/0133016 A1 | 6/2008 | Heinz |
| 2008/0139907 A1 | 6/2008 | Rao et al. |
| 2008/0154335 A1 | 6/2008 | Thrope et al. |
| 2008/0161879 A1 | 7/2008 | Firlik et al. |
| 2008/0161882 A1 | 7/2008 | Firlik et al. |
| 2008/0161887 A1 | 7/2008 | Hagen |
| 2008/0170234 A1 | 7/2008 | Kim |
| 2008/0170316 A1 | 7/2008 | Kim |
| 2008/0195163 A1 | 8/2008 | Scharmer |
| 2008/0200967 A1 | 8/2008 | Ponomarev et al. |
| 2008/0208280 A1 | 8/2008 | Lindenthaler et al. |
| 2008/0215112 A1 | 9/2008 | Firlik et al. |
| 2008/0221653 A1 | 9/2008 | Agrawal et al. |
| 2008/0241208 A1 | 10/2008 | Shanley et al. |
| 2008/0242607 A1 | 10/2008 | DeFrees |
| 2008/0243218 A1 | 10/2008 | Bottomley et al. |
| 2008/0248959 A1 | 10/2008 | DeFrees |
| 2008/0249439 A1 | 10/2008 | Tracey et al. |
| 2008/0253992 A1 | 10/2008 | DeFrees et al. |
| 2008/0255582 A1 | 10/2008 | Harris |
| 2008/0262557 A1 | 10/2008 | Brown |
| 2008/0262584 A1 | 10/2008 | Bottomley et al. |
| 2008/0274958 A1 | 11/2008 | DeFrees |
| 2008/0275546 A1 | 11/2008 | Storey et al. |
| 2008/0280818 A1 | 11/2008 | DeFrees |
| 2008/0312538 A1 | 12/2008 | Shahar et al. |
| 2008/0318314 A1 | 12/2008 | Fulga et al. |
| 2009/0012586 A1 | 1/2009 | Kepecs |
| 2009/0012590 A1 | 1/2009 | Inman et al. |
| 2009/0029912 A1 | 1/2009 | Gronthos et al. |
| 2009/0036938 A1 | 2/2009 | Shipley et al. |
| 2009/0054800 A1 | 2/2009 | Martinerie et al. |
| 2009/0054950 A1 | 2/2009 | Stephens |
| 2009/0076421 A1 | 3/2009 | Grant |
| 2009/0076444 A1 | 3/2009 | Machado et al. |
| 2009/0086015 A1 | 4/2009 | Larsen et al. |
| 2009/0105149 A1 | 4/2009 | Albrechtsen et al. |
| 2009/0112278 A1 | 4/2009 | Wingeier et al. |
| 2009/0112279 A1 | 4/2009 | Wingeier et al. |
| 2009/0118788 A1 | 5/2009 | Firlik et al. |
| 2009/0124965 A1 | 5/2009 | Greenberg et al. |
| 2009/0131995 A1 | 5/2009 | Sloan et al. |

(56) References Cited

U.S. PATENT DOCUMENTS

| | | |
|---|---|---|
| 2009/0132018 A1 | 5/2009 | DiUbaldi et al. |
| 2009/0149782 A1 | 6/2009 | Cohen |
| 2009/0149900 A1 | 6/2009 | Moffitt et al. |
| 2009/0157091 A1 | 6/2009 | Buysman |
| 2009/0171381 A1 | 7/2009 | Schmitz et al. |
| 2009/0182393 A1 | 7/2009 | Bachinski |
| 2009/0201671 A1 | 8/2009 | Huntley |
| 2009/0214474 A1 | 8/2009 | Jennings |
| 2009/0215896 A1 | 8/2009 | Morseman et al. |
| 2009/0220466 A1 | 9/2009 | Ratajczak et al. |
| 2009/0226598 A1 | 9/2009 | Feng et al. |
| 2009/0227025 A1 | 9/2009 | Nichols et al. |
| 2009/0227965 A1 | 9/2009 | Wijesiriwardana |
| 2009/0234265 A1 | 9/2009 | Reid et al. |
| 2009/0258048 A1 | 10/2009 | Ward et al. |
| 2009/0270958 A1 | 10/2009 | Greenberg et al. |
| 2009/0292338 A1 | 11/2009 | Gordon et al. |
| 2009/0299439 A1 | 12/2009 | Mire et al. |
| 2009/0306728 A1 | 12/2009 | Wright et al. |
| 2009/0306745 A1 | 12/2009 | Parker et al. |
| 2009/0326612 A1 | 12/2009 | Distler |
| 2010/0004654 A1 | 1/2010 | Schmitz et al. |
| 2010/0010550 A1 | 1/2010 | Ponomarev et al. |
| 2010/0016732 A1 | 1/2010 | Wells et al. |
| 2010/0035299 A1 | 2/2010 | DeFrees et al. |
| 2010/0037755 A1 | 2/2010 | McMillen et al. |
| 2010/0042180 A1 | 2/2010 | Mueller et al. |
| 2010/0042185 A1 | 2/2010 | Curtis |
| 2010/0045595 A1 | 2/2010 | Bakke |
| 2010/0047915 A1 | 2/2010 | Soykan et al. |
| 2010/0092983 A1 | 4/2010 | Liew |
| 2010/0092984 A1 | 4/2010 | Liew |
| 2010/0094311 A1 | 4/2010 | Jolly et al. |
| 2010/0099786 A1 | 4/2010 | Dias et al. |
| 2010/0112026 A1 | 5/2010 | Karp et al. |
| 2010/0114195 A1 | 5/2010 | Burnes et al. |
| 2010/0124745 A1 | 5/2010 | Liew |
| 2010/0124746 A1 | 5/2010 | Liew |
| 2010/0145427 A1 | 6/2010 | Gliner et al. |
| 2010/0168739 A1 | 7/2010 | Wu et al. |
| 2010/0179284 A1 | 7/2010 | Ward et al. |
| 2010/0185042 A1 | 7/2010 | Schneider et al. |
| 2010/0189712 A1 | 7/2010 | Heureux et al. |
| 2010/0203520 A1 | 8/2010 | Liew |
| 2010/0204538 A1 | 8/2010 | Burnett et al. |
| 2010/0204777 A1 | 8/2010 | Storey et al. |
| 2010/0211172 A1 | 8/2010 | Bellamkonda et al. |
| 2010/0222630 A1 | 9/2010 | Mangrum et al. |
| 2010/0222844 A1 | 9/2010 | Troosters et al. |
| 2010/0241195 A1 | 9/2010 | Meadows et al. |
| 2010/0268055 A1 | 10/2010 | Jung et al. |
| 2010/0268125 A9 | 10/2010 | Epley |
| 2010/0280570 A1 | 11/2010 | Sturm et al. |
| 2010/0280571 A1 | 11/2010 | Sloan |
| 2010/0286067 A1 | 11/2010 | DeFrees |
| 2010/0292759 A1 | 11/2010 | Hahn et al. |
| 2010/0298916 A1 | 11/2010 | Rabischong et al. |
| 2010/0304864 A1 | 12/2010 | Johnson et al. |
| 2010/0305674 A1 | 12/2010 | Zarembo et al. |
| 2010/0310529 A1 | 12/2010 | Aizman |
| 2010/0324355 A1 | 12/2010 | Spitaels et al. |
| 2010/0324626 A1 | 12/2010 | Lefkovitz |
| 2011/0009959 A1 | 1/2011 | Tiedtke |
| 2011/0014189 A1 | 1/2011 | Soula et al. |
| 2011/0022105 A9 | 1/2011 | Owen et al. |
| 2011/0022131 A1 | 1/2011 | Giuliano |
| 2011/0028345 A1 | 2/2011 | Fang et al. |
| 2011/0040204 A1 | 2/2011 | Ivorra et al. |
| 2011/0040349 A1 | 2/2011 | Graupe |
| 2011/0059447 A1 | 3/2011 | Liew |
| 2011/0060266 A1 | 3/2011 | Streeter et al. |
| 2011/0082531 A1 | 4/2011 | Swanson et al. |
| 2011/0092863 A1 | 4/2011 | Kim et al. |
| 2011/0098777 A1 | 4/2011 | Silverstone |
| 2011/0106207 A1 | 5/2011 | Cauller et al. |
| 2011/0106219 A1 | 5/2011 | Cauller et al. |
| 2011/0112352 A1 | 5/2011 | Pilla et al. |
| 2011/0118556 A1 | 5/2011 | Siegel et al. |
| 2011/0124959 A1 | 5/2011 | Murison |
| 2011/0137189 A1 | 6/2011 | Kuo et al. |
| 2011/0158444 A1 | 6/2011 | Waldmann |
| 2011/0177029 A1 | 7/2011 | DeFrees |
| 2011/0184269 A1 | 7/2011 | Sauter-Starace et al. |
| 2011/0190882 A1 | 8/2011 | Parker et al. |
| 2011/0195106 A1 | 8/2011 | McMurtrey |
| 2011/0196454 A1 | 8/2011 | Strand et al. |
| 2011/0202120 A1 | 8/2011 | Ball et al. |
| 2011/0208226 A1 | 8/2011 | Fatone et al. |
| 2011/0218593 A1 | 9/2011 | Rubinstein et al. |
| 2011/0224565 A1 | 9/2011 | Ong et al. |
| 2011/0224754 A1 | 9/2011 | Wei |
| 2011/0257501 A1 | 10/2011 | Huys et al. |
| 2011/0257504 A1 | 10/2011 | Hendricks et al. |
| 2011/0262501 A1 | 10/2011 | Webster et al. |
| 2011/0264178 A1 | 10/2011 | Mehregany et al. |
| 2011/0268776 A1 | 11/2011 | Schapira et al. |
| 2011/0270345 A1 | 11/2011 | Johnston et al. |
| 2011/0270361 A1 | 11/2011 | Borsody |
| 2011/0295156 A1 | 12/2011 | Arturi |
| 2011/0301662 A1 | 12/2011 | Bar-Yoseph et al. |
| 2011/0313270 A1 | 12/2011 | Neves et al. |
| 2011/0319703 A1 | 12/2011 | Wiskerke et al. |
| 2012/0016431 A1 | 1/2012 | Paul et al. |
| 2012/0016440 A1 | 1/2012 | Muccio |
| 2012/0022616 A1 | 1/2012 | Garnham et al. |
| 2012/0035684 A1 | 2/2012 | Thompson et al. |
| 2012/0045487 A1 | 2/2012 | Lahann et al. |
| 2012/0046702 A1 | 2/2012 | Gibson |
| 2012/0059389 A1 | 3/2012 | Larson et al. |
| 2012/0064628 A1 | 3/2012 | Blick et al. |
| 2012/0076830 A1 | 3/2012 | Sitharaman et al. |
| 2012/0078327 A1 | 3/2012 | Sloan et al. |
| 2012/0089047 A1 | 4/2012 | Ryba et al. |
| 2012/0095166 A1 | 4/2012 | Ward et al. |
| 2012/0095524 A1 | 4/2012 | Nelson et al. |
| 2012/0101326 A1 | 4/2012 | Simon et al. |
| 2012/0101413 A1 | 4/2012 | Beetel et al. |
| 2012/0109233 A1 | 5/2012 | Lee et al. |
| 2012/0123508 A1 | 5/2012 | Wentz et al. |
| 2012/0124470 A1 | 5/2012 | West et al. |
| 2012/0130360 A1 | 5/2012 | Buckley et al. |
| 2012/0134965 A1 | 5/2012 | Kim et al. |
| 2012/0136232 A1 | 5/2012 | Jeong et al. |
| 2012/0143293 A1 | 6/2012 | Mauch et al. |
| 2012/0158095 A1 | 6/2012 | Jolly |
| 2012/0158104 A1 | 6/2012 | Huynh et al. |
| 2012/0158113 A1 | 6/2012 | Jolly et al. |
| 2012/0158114 A1 | 6/2012 | Debruyne et al. |
| 2012/0179076 A1 | 7/2012 | Bavelier et al. |
| 2012/0185173 A1 | 7/2012 | Yamamoto et al. |
| 2012/0191052 A1 | 7/2012 | Rao |
| 2012/0191086 A1 | 7/2012 | Moll et al. |
| 2012/0197092 A1 | 8/2012 | Luo et al. |
| 2012/0197252 A1 | 8/2012 | Deem et al. |
| 2012/0197374 A1 | 8/2012 | Vogt et al. |
| 2012/0214737 A1 | 8/2012 | Marchionni |
| 2012/0221072 A1 | 8/2012 | Fukamachi et al. |
| 2012/0226331 A1 | 9/2012 | Banna et al. |
| 2012/0237557 A1 | 9/2012 | Lewitus et al. |
| 2012/0238924 A1 | 9/2012 | Avni |
| 2012/0239363 A1 | 9/2012 | Durrani et al. |
| 2012/0244503 A1 | 9/2012 | Neveldine |
| 2012/0245534 A1 | 9/2012 | Jolly |
| 2012/0253236 A1 | 10/2012 | Snow et al. |
| 2012/0259255 A1 | 10/2012 | Tomlinson et al. |
| 2012/0259390 A1 | 10/2012 | Canion |
| 2012/0277825 A1 | 11/2012 | Mawson et al. |
| 2012/0277842 A1 | 11/2012 | Kunis |
| 2012/0282228 A1 | 11/2012 | Bhasin |
| 2012/0283800 A1 | 11/2012 | Perryman et al. |
| 2012/0296191 A1 | 11/2012 | McGrath et al. |
| 2012/0296230 A1 | 11/2012 | Davis et al. |
| 2012/0296444 A1 | 11/2012 | Greenberg et al. |
| 2012/0302856 A1 | 11/2012 | Chang et al. |

(56) References Cited

U.S. PATENT DOCUMENTS

| | | |
|---|---|---|
| 2012/0310140 A1 | 12/2012 | Kramer et al. |
| 2012/0323288 A1 | 12/2012 | Anderson et al. |
| 2013/0012831 A1 | 1/2013 | Schmitz et al. |
| 2013/0018240 A1 | 1/2013 | McCoy |
| 2013/0018444 A1 | 1/2013 | Glenn et al. |
| 2013/0035745 A1 | 2/2013 | Ahmed et al. |
| 2013/0041432 A1 | 2/2013 | Tucker et al. |
| 2013/0052712 A1 | 2/2013 | Cha et al. |
| 2013/0053853 A1 | 2/2013 | Schmitz et al. |
| 2013/0053934 A1 | 2/2013 | Gluckman et al. |
| 2013/0066147 A1 | 3/2013 | Brown |
| 2013/0066216 A1 | 3/2013 | Park |
| 2013/0066391 A1 | 3/2013 | Hulvershorn et al. |
| 2013/0066392 A1 | 3/2013 | Simon et al. |
| 2013/0066395 A1 | 3/2013 | Simon et al. |
| 2013/0072808 A1 | 3/2013 | Neves et al. |
| 2013/0072835 A1 | 3/2013 | Harry et al. |
| 2013/0090542 A1 | 4/2013 | Kipke et al. |
| 2013/0090711 A1 | 4/2013 | Ramachandran et al. |
| 2013/0101635 A1 | 4/2013 | Park et al. |
| 2013/0116685 A1 | 5/2013 | Deem et al. |
| 2013/0116744 A1 | 5/2013 | Blum et al. |
| 2013/0122528 A1 | 5/2013 | Tyrell et al. |
| 2013/0123568 A1 | 5/2013 | Hamilton et al. |
| 2013/0123570 A1 | 5/2013 | Ly et al. |
| 2013/0131743 A1 | 5/2013 | Yamasaki et al. |
| 2013/0131753 A1 | 5/2013 | Simon et al. |
| 2013/0137955 A1 | 5/2013 | Kong et al. |
| 2013/0144143 A1 | 6/2013 | Kim et al. |
| 2013/0144369 A1 | 6/2013 | Elias et al. |
| 2013/0144370 A1 | 6/2013 | Debruyne et al. |
| 2013/0150653 A1 | 6/2013 | Borsody |
| 2013/0154838 A1 | 6/2013 | Alameh et al. |
| 2013/0157229 A1 | 6/2013 | Lauritzen et al. |
| 2013/0178765 A1 | 7/2013 | Mishelevich |
| 2013/0184792 A1 | 7/2013 | Simon et al. |
| 2013/0184795 A1 | 7/2013 | Kipke et al. |
| 2013/0184799 A1 | 7/2013 | Kipke et al. |
| 2013/0204122 A1 | 8/2013 | Hendler et al. |
| 2013/0204317 A1 | 8/2013 | Sauter-Starace et al. |
| 2013/0210041 A1 | 8/2013 | Anderberg et al. |
| 2013/0218456 A1 | 8/2013 | Zelek et al. |
| 2013/0231725 A1 | 9/2013 | Williams et al. |
| 2013/0238066 A1 | 9/2013 | Joseph et al. |
| 2013/0238074 A1 | 9/2013 | Zimmerling |
| 2013/0245480 A1 | 9/2013 | Crockford |
| 2013/0245486 A1 | 9/2013 | Simon et al. |
| 2013/0245711 A1 | 9/2013 | Simon et al. |
| 2013/0245712 A1 | 9/2013 | Simon et al. |
| 2013/0245717 A1 | 9/2013 | Stohl et al. |
| 2013/0245765 A1 | 9/2013 | Lowry et al. |
| 2013/0248226 A1 | 9/2013 | Sime et al. |
| 2013/0253299 A1 | 9/2013 | Weber et al. |
| 2013/0274540 A1 | 10/2013 | Pilla et al. |
| 2013/0274658 A1 | 10/2013 | Steinke et al. |
| 2013/0274842 A1 | 10/2013 | Gaunt et al. |
| 2013/0280233 A1 | 10/2013 | Kahn et al. |
| 2013/0282001 A1 | 10/2013 | Hezi-Yamit et al. |
| 2013/0282090 A1 | 10/2013 | Decré et al. |
| 2013/0288233 A1 | 10/2013 | Murray |
| 2013/0289678 A1 | 10/2013 | Clark et al. |
| 2013/0289686 A1 | 10/2013 | Masson et al. |
| 2013/0296767 A1 | 11/2013 | Zarins et al. |
| 2013/0309278 A1 | 11/2013 | Peyman |
| 2013/0310909 A1 | 11/2013 | Simon et al. |
| 2013/0317400 A1 | 11/2013 | Ferezy |
| 2013/0317580 A1 | 11/2013 | Simon et al. |
| 2013/0324994 A1 | 12/2013 | Pellegrino et al. |
| 2013/0331869 A1 | 12/2013 | Runge et al. |
| 2013/0338729 A1 | 12/2013 | Spector |
| 2013/0341185 A1 | 12/2013 | Collaert et al. |
| 2014/0003696 A1 | 1/2014 | Taghva |
| 2014/0018792 A1 | 1/2014 | Gang et al. |
| 2014/0022162 A1 | 1/2014 | Yu et al. |
| 2014/0023999 A1 | 1/2014 | Greder |
| 2014/0024981 A1 | 1/2014 | Chun et al. |
| 2014/0025301 A1 | 1/2014 | Storm et al. |
| 2014/0030735 A1 | 1/2014 | Merali et al. |
| 2014/0046423 A1 | 2/2014 | Rajguru et al. |
| 2014/0051938 A1 | 2/2014 | Goldstein et al. |
| 2014/0058481 A1 | 2/2014 | Perryman et al. |
| 2014/0058483 A1 | 2/2014 | Zao et al. |
| 2014/0066924 A1 | 3/2014 | Azamian et al. |
| 2014/0073883 A1 | 3/2014 | Rao et al. |
| 2014/0074186 A1 | 3/2014 | Faltys et al. |
| 2014/0081682 A1 | 3/2014 | Perlmuter |
| 2014/0094674 A1 | 4/2014 | Nurmikko et al. |
| 2014/0099352 A1 | 4/2014 | Matheny |
| 2014/0107397 A1 | 4/2014 | Simon et al. |
| 2014/0107398 A1 | 4/2014 | Simon et al. |
| 2014/0114168 A1 | 4/2014 | Block et al. |
| 2014/0127171 A1 | 5/2014 | Nocera et al. |
| 2014/0128939 A1 | 5/2014 | Embrey et al. |
| 2014/0135607 A1 | 5/2014 | Lee et al. |
| 2014/0135680 A1 | 5/2014 | Peyman |
| 2014/0142374 A1 | 5/2014 | Makower et al. |
| 2014/0148649 A1 | 5/2014 | Miles et al. |
| 2014/0148871 A1 | 5/2014 | Southwell et al. |
| 2014/0148872 A1 | 5/2014 | Goldwasser et al. |
| 2014/0155811 A1 | 6/2014 | Gibson |
| 2014/0155973 A1 | 6/2014 | Grigsby et al. |
| 2014/0163580 A1 | 6/2014 | Tischendorf et al. |
| 2014/0163641 A1 | 6/2014 | Yao et al. |
| 2014/0163658 A1 | 6/2014 | Faraji et al. |
| 2014/0171807 A1 | 6/2014 | Akkin et al. |
| 2014/0180036 A1 | 6/2014 | Bukkapatnam et al. |
| 2014/0180196 A1 | 6/2014 | Stone et al. |
| 2014/0180365 A1 | 6/2014 | Perryman et al. |
| 2014/0187872 A1 | 7/2014 | Stivoric et al. |
| 2014/0197937 A1 | 7/2014 | Huang et al. |
| 2014/0200432 A1 | 7/2014 | Banerji et al. |
| 2014/0200466 A1 | 7/2014 | Sereno et al. |
| 2014/0200496 A1 | 7/2014 | Hyde et al. |
| 2014/0200681 A1 | 7/2014 | Kennedy et al. |
| 2014/0206947 A1 | 7/2014 | Isserow et al. |
| 2014/0207292 A1 | 7/2014 | Ramagem et al. |
| 2014/0213842 A1 | 7/2014 | Simon et al. |
| 2014/0213971 A1 | 7/2014 | Dolan et al. |
| 2014/0220555 A1 | 8/2014 | Chen et al. |
| 2014/0222125 A1 | 8/2014 | Glenn et al. |
| 2014/0225763 A1 | 8/2014 | Kavaler et al. |
| 2014/0228901 A1 | 8/2014 | Vogt |
| 2014/0228926 A1 | 8/2014 | Santina et al. |
| 2014/0235950 A1 | 8/2014 | Miles et al. |
| 2014/0236249 A1 | 8/2014 | Rao et al. |
| 2014/0236847 A1 | 8/2014 | Hamilton |
| 2014/0243616 A1 | 8/2014 | Johnson |
| 2014/0243932 A1 | 8/2014 | Libbus et al. |
| 2014/0249395 A1 | 9/2014 | Zhou et al. |
| 2014/0255461 A9 | 9/2014 | McMurtrey |
| 2014/0257063 A1 | 9/2014 | Ong et al. |
| 2014/0257437 A1 | 9/2014 | Simon et al. |
| 2014/0267123 A1 | 9/2014 | Ludwig |
| 2014/0275737 A1 | 9/2014 | Shore et al. |
| 2014/0276718 A1 | 9/2014 | Turovskiy et al. |
| 2014/0276760 A1 | 9/2014 | Bonyak et al. |
| 2014/0277031 A1 | 9/2014 | Ballakur et al. |
| 2014/0277033 A1 | 9/2014 | Taylor et al. |
| 2014/0277220 A1 | 9/2014 | Brennan et al. |
| 2014/0277237 A1 | 9/2014 | Maskara et al. |
| 2014/0277271 A1 | 9/2014 | Chan et al. |
| 2014/0277310 A1 | 9/2014 | Beetel et al. |
| 2014/0277582 A1 | 9/2014 | Leuthardt et al. |
| 2014/0288379 A1 | 9/2014 | Miles et al. |
| 2014/0296646 A1 | 10/2014 | Wingeier et al. |
| 2014/0300490 A1 | 10/2014 | Kotz et al. |
| 2014/0303525 A1 | 10/2014 | Sitharaman |
| 2014/0303548 A1 | 10/2014 | Jolly et al. |
| 2014/0304773 A1 | 10/2014 | Woods et al. |
| 2014/0309548 A1 | 10/2014 | Merz et al. |
| 2014/0316398 A1 | 10/2014 | Kelly et al. |
| 2014/0320289 A1 | 10/2014 | Raichman |
| 2014/0330337 A1 | 11/2014 | Linke et al. |
| 2014/0336631 A1 | 11/2014 | Wu et al. |

(56) References Cited

U.S. PATENT DOCUMENTS

| | | |
|---|---|---|
| 2014/0336722 A1 | 11/2014 | Lima et al. |
| 2014/0350041 A1 | 11/2014 | Yun et al. |
| 2014/0350633 A1 | 11/2014 | Gustafson et al. |
| 2014/0357453 A1 | 12/2014 | Tamanaha |
| 2014/0357933 A1 | 12/2014 | Lee et al. |
| 2014/0360511 A1 | 12/2014 | Mohler |
| 2014/0371547 A1 | 12/2014 | Gartenberg et al. |
| 2014/0371564 A1 | 12/2014 | Anikeeva et al. |
| 2014/0371622 A1 | 12/2014 | Hausman et al. |
| 2014/0375457 A1 | 12/2014 | Diaz |
| 2014/0378779 A1 | 12/2014 | Freeman et al. |
| 2014/0378789 A1 | 12/2014 | McKinley et al. |
| 2014/0378946 A1 | 12/2014 | Thompson et al. |
| 2014/0379045 A1 | 12/2014 | Rahimi et al. |
| 2014/0379049 A1 | 12/2014 | Mashiach et al. |
| 2015/0005607 A1 | 1/2015 | Cui et al. |
| 2015/0005680 A1 | 1/2015 | Lipani |
| 2015/0005840 A1 | 1/2015 | Pal et al. |
| 2015/0005841 A1 | 1/2015 | Pal et al. |
| 2015/0005851 A1 | 1/2015 | Bradley |
| 2015/0010607 A1 | 1/2015 | Francis et al. |
| 2015/0012079 A1 | 1/2015 | Goroszeniuk et al. |
| 2015/0016647 A1 | 1/2015 | Martinez et al. |
| 2015/0017140 A1 | 1/2015 | Bhatia et al. |
| 2015/0018659 A1 | 1/2015 | Ware et al. |
| 2015/0032044 A9 | 1/2015 | Peyman |
| 2015/0032178 A1 | 1/2015 | Simon et al. |
| 2015/0032184 A1 | 1/2015 | Muccio |
| 2015/0038886 A1 | 2/2015 | Snow |
| 2015/0039055 A1 | 2/2015 | Wagner et al. |
| 2015/0049325 A1 | 2/2015 | Curtis |
| 2015/0051439 A1 | 2/2015 | Hillbratt et al. |
| 2015/0051684 A1 | 2/2015 | Greenberg et al. |
| 2015/0057736 A1 | 2/2015 | Zachar |
| 2015/0059390 A1 | 3/2015 | Hayes |
| 2015/0062018 A1 | 3/2015 | Naidu et al. |
| 2015/0066126 A1 | 3/2015 | Marx et al. |
| 2015/0067422 A1 | 3/2015 | Hamilton |
| 2015/0073232 A1 | 3/2015 | Ahmad et al. |
| 2015/0073520 A1 | 3/2015 | Strahl et al. |
| 2015/0080709 A1 | 3/2015 | Chaturvedi |
| 2015/0080926 A1 | 3/2015 | Emery |
| 2015/0088030 A1 | 3/2015 | Taylor |
| 2015/0088223 A1 | 3/2015 | Blum et al. |
| 2015/0088224 A1 | 3/2015 | Goldwasser et al. |
| 2015/0088225 A1 | 3/2015 | Noble et al. |
| 2015/0102925 A1 | 4/2015 | Foldyna et al. |
| 2015/0105794 A1 | 4/2015 | Dhanasingh et al. |
| 2015/0105795 A1 | 4/2015 | Lenarz et al. |
| 2015/0112234 A1 | 4/2015 | McCaffrey et al. |
| 2015/0112321 A1 | 4/2015 | Cadouri |
| 2015/0112359 A1 | 4/2015 | Gillbe |
| 2015/0112360 A1 | 4/2015 | Pellinen et al. |
| 2015/0112404 A1 | 4/2015 | Holding et al. |
| 2015/0112405 A1 | 4/2015 | Brown et al. |
| 2015/0112408 A1 | 4/2015 | Kals |
| 2015/0119673 A1 | 4/2015 | Pellinen et al. |
| 2015/0119790 A1 | 4/2015 | Moffitt et al. |
| 2015/0119954 A2 | 4/2015 | Bhadra et al. |
| 2015/0119989 A1 | 4/2015 | Pimenta et al. |
| 2015/0126997 A1 | 5/2015 | Beetel et al. |
| 2015/0133761 A1 | 5/2015 | Vetter et al. |
| 2015/0133956 A1 | 5/2015 | Dayan et al. |
| 2015/0135840 A1 | 5/2015 | Sato et al. |
| 2015/0148643 A1 | 5/2015 | Small et al. |
| 2015/0148644 A1 | 5/2015 | Vaidyanathan et al. |
| 2015/0148736 A1 | 5/2015 | Jolly et al. |
| 2015/0148869 A1 | 5/2015 | Alan et al. |
| 2015/0148878 A1 | 5/2015 | Yoo et al. |
| 2015/0150508 A1 | 6/2015 | Glenn et al. |
| 2015/0157398 A1 | 6/2015 | Zarins et al. |
| 2015/0157851 A1 | 6/2015 | Sefkow et al. |
| 2015/0157854 A1 | 6/2015 | Hetke et al. |
| 2015/0157862 A1 | 6/2015 | Greenberg et al. |
| 2015/0164360 A1 | 6/2015 | Kipke et al. |
| 2015/0164401 A1 | 6/2015 | Toth et al. |
| 2015/0173673 A1 | 6/2015 | Toth et al. |
| 2015/0173918 A1 | 6/2015 | Herr et al. |
| 2015/0174403 A1 | 6/2015 | Pal et al. |
| 2015/0174418 A1 | 6/2015 | Tyler et al. |
| 2015/0182753 A1 | 7/2015 | Harris et al. |
| 2015/0190635 A1 | 7/2015 | Neuvonen et al. |
| 2015/0190636 A1 | 7/2015 | Simon et al. |
| 2015/0190637 A1 | 7/2015 | Simon et al. |
| 2015/0196767 A1 | 7/2015 | Ahmed |
| 2015/0201855 A1 | 7/2015 | Pellinen et al. |
| 2015/0202331 A1 | 7/2015 | Blumenfeld et al. |
| 2015/0202437 A1 | 7/2015 | Franke et al. |
| 2015/0209104 A1 | 7/2015 | Tran et al. |
| 2015/0209577 A1 | 7/2015 | Golestanirad et al. |
| 2015/0209586 A1 | 7/2015 | Silva et al. |
| 2015/0217125 A1 | 8/2015 | Chornenky et al. |
| 2015/0223731 A1 | 8/2015 | Sahin |
| 2015/0224300 A1 | 8/2015 | Hagr et al. |
| 2015/0224330 A1 | 8/2015 | Kaib et al. |
| 2015/0230749 A1 | 8/2015 | Gharib et al. |
| 2015/0231396 A1 | 8/2015 | Burdick et al. |
| 2015/0235529 A1 | 8/2015 | Deschamps |
| 2015/0238104 A1 | 8/2015 | Tass |
| 2015/0238253 A1 | 8/2015 | Wu et al. |
| 2015/0238764 A1 | 8/2015 | Franke |
| 2015/0246072 A1 | 9/2015 | Bhatia et al. |
| 2015/0248470 A1 | 9/2015 | Coleman et al. |
| 2015/0251004 A1 | 9/2015 | Imran et al. |
| 2015/0254992 A1 | 9/2015 | Sethi |
| 2015/0257824 A1 | 9/2015 | Mauch |
| 2015/0272805 A1 | 10/2015 | Burnett et al. |
| 2015/0273206 A1 | 10/2015 | Monteiro |
| 2015/0283365 A1 | 10/2015 | Dacey et al. |
| 2015/0284416 A1 | 10/2015 | Zhao |
| 2015/0290439 A1 | 10/2015 | Eldredge et al. |
| 2015/0290450 A1 | 10/2015 | Kolb et al. |
| 2015/0290464 A1 | 10/2015 | Monteiro |
| 2015/0290472 A1 | 10/2015 | Maguire et al. |
| 2015/0297104 A1 | 10/2015 | Chen et al. |
| 2015/0297444 A1 | 10/2015 | Tass |
| 2015/0297914 A1 | 10/2015 | Hamid et al. |
| 2015/0305667 A1 | 10/2015 | Durand |
| 2015/0305686 A1 | 10/2015 | Coleman et al. |
| 2015/0310762 A1 | 10/2015 | Seim et al. |
| 2015/0313498 A1 | 11/2015 | Coleman et al. |
| 2015/0313512 A1 | 11/2015 | Hausman et al. |
| 2015/0314017 A1 | 11/2015 | Zhao |
| 2015/0320560 A1 | 11/2015 | Mulliken et al. |
| 2015/0320588 A1 | 11/2015 | Connor |
| 2015/0321000 A1 | 11/2015 | Rosenbluth et al. |
| 2015/0321010 A1 | 11/2015 | Marnfeldt |
| 2015/0321017 A1 | 11/2015 | Perryman et al. |
| 2015/0322155 A1 | 11/2015 | Zhao |
| 2015/0328454 A1 | 11/2015 | Lambert |
| 2015/0328455 A1 | 11/2015 | Meadows et al. |
| 2015/0335288 A1 | 11/2015 | Toth et al. |
| 2015/0335876 A1 | 11/2015 | Jeffery et al. |
| 2015/0335877 A1 | 11/2015 | Jeffery et al. |
| 2015/0335883 A1 | 11/2015 | Halpern et al. |
| 2015/0343196 A1 | 12/2015 | Vasapollo |
| 2015/0343215 A1 | 12/2015 | Ridder |
| 2015/0343242 A1 | 12/2015 | Tyler et al. |
| 2015/0354922 A1 | 12/2015 | Carriere |
| 2015/0359704 A1 | 12/2015 | Imboden et al. |
| 2015/0364018 A1 | 12/2015 | Mirov et al. |
| 2015/0374515 A1 | 12/2015 | Meijer et al. |
| 2015/0379880 A1 | 12/2015 | Sethi |
| 2017/0080216 A1 | 3/2017 | Pham |
| 2017/0209693 A1 | 7/2017 | An et al. |

FOREIGN PATENT DOCUMENTS

| | | |
|---|---|---|
| FR | 2646779 B1 | 7/1993 |
| JP | 2011502707 A | 1/2011 |
| JP | 2013500080 A | 1/2013 |
| WO | 2011011748 A1 | 1/2011 |

(56) References Cited

FOREIGN PATENT DOCUMENTS

| WO | 2011053607 A1 | 5/2011 |
|---|---|---|
| WO | 2012129574 A2 | 9/2012 |

OTHER PUBLICATIONS

US 8,613,701 B2, 12/2013, Rao et al. (withdrawn)
US 8,652,133 B2, 02/2014, Zarins et al. (withdrawn)
Nijman, RJ; Role of antimuscarinics in the treatment of non-neurogenic daytime urinary incontinence in children; Urology; 2004; 45-50; 63.
Nilsson, KF, et al.; Estimation of endogenous adenosine activity at adenosine receptors in guinea-pig ileum using a new pharmacolofical method; Acta Physiol (Oxf); 2010; 231-241; 199.
Nitti, VW; Urodynamics, Incontinence, and Neurourology: Highlights from the Society for Urodynamics and Female Urology Annual Winter Meeting, Feb. 28-Mar. 2, 2008, Miami, FL; Rev Urol; 2008; 229-231; 10.
Noblett, K. et al.; Results of a prospective, multicenter study evaluating quality of life, safety, and efficacy of sacral neuromodulation at twelve months in subjects with symptoms of overactive bladder; Neurourol Urodyn; 2016; 246-251; 35.
Noblett, KL., et al.; Sacral nerve stimulation for the treatment of refractory voiding and bowel dysfunction: Am J Obstet Gynecol; 2014, 99-106; 210.
Nordling, J: Surgical treatment of painful bladder syndrome/interstitial cystitis: Womens Health (Lond Engl): 2006: 233-238: 2.
Nyarangi-Dix, JN, et al.; [Overactive bladder syndrome. Are there indications for surgical therapy?]: Urologe A; 2006; 1289-1290, 1292: 45.
Occhino, JA, et al.; Sacral nerve modulation in overactive bladder; Curr Urol Rep: 2010: 348-352: 11.
Oerlemans, DJ, et al.: Is on-demand sacral neuromodulation in patients with OAB syndrome a feasible therapy regime?: Neurourol Urodyn: 2011: 1493-1496; 30.
Oerlemans, DJ. et al.: Sacral nerve stimulation for neuromodulation of the lower urinary tract: Neurourol Urodyn: 2008; 28-33; 27.
Offiah, I, et al.; Interstitial cystitis/bladder pain syndrome: diagnosis and management: Int Urogynecol J; 2013: 1243-1256: 24.
Oliver. S, et al.: Measuring the sensations of urge and bladder filling during cystometry in urge incontinence and the effects of neuromodulation; Neurourol Urodyn: 2003; 42567: 22.
Olivera, CK, et al.; Non-antimuscarinic treatment for overactive bladder: a systemactic review; Am J Obstet Gynecol: 2016:Abstract.
Olujide. LO, et al.: Female voiding dysfunction; Best Pract Res Clin Obstet Gynaecol: 2005; 807-828: 19.
Oom, DM. et al.; Anterior sphincteroplasty for fecal incontinence: a single center experience in the era of sacral neuomodulation; Dis Colon Rectum: 2009; 1681-1687: 52.
Oom, DM, et al; Is sacral neuromodulation for fecal incontinence worthwhile in patients with associated pelvic floor injury?; Dis Colon Rectum: 2010; 422-427: 53.
Ordia, JI, et al.; Continuous intrathecal baclofen infusion delivered by a programmable pump for the treatment of severe spasticity following traumatic brain injury: Neuromodulation; 2002: 103-107; 5.
O'Reilly, BA, et al.; A prospective randomised double-blind controlled trial evaluating the effect of trans-sacral magnetic stimulation in women with overactive bladder: Int Urogynecol J Pelvic Floor Dysfunct; 2008; 497-502; 19.
Osman, NI, et al.: Fowler's syndrome—a cause of unexplained orinary retention in young women?; Nat Rev Urol; 2014; 87-98: 11;Abstract.
Osman, NI, et al.: Overactive bladder syndrome: Current pathophysiological concepts and therapeutic approaches; Arab J Urol; 2013; 313-318; 11.
Otto, W, et al.; [Sacral neuromodulation as second-line treatment strategy for lower urinary tract symptoms of various aetiologies: experience of a German high-volume clinic]: Aktuelle Urol: 2012; 162-166; 43;Abstract.

Ozyalcin, NS, et al.; [Sacral nerve stimulation in fecal incontinence: efficacy and safety]; Agri: 2004; 35-44; 16;Abstract.
Panicker, JN, et al.; Lower urinary tract dysfuntion in the neurological patient; clinical assessment and management; Lancet Neurol; 2015: 720-732; 14.
Pannek, J, et al.; [Initial results of Stoller peripheral neuromodulation in disorders of bladder function]; Urologe A; 2003; 1470-1476; 42.
Parija, SC, et al.; Adenosine- and alpha,beta-methylene ATP-induced differential inhibition of cholinergic and non-cholinergic neurogenic responses in a rat urinary bladder; Br J Pharmacol; 1991; 396-400; 102.
Park, SH, et al.; Overactive bladder; treatment options for the aging woman; Int J Fertil Womens Med; 2005; 37-44; 50;Abstract.
Parnell, BA, et al.; The effect of sacral neuromodulation on pudendal nerve function and female sexual function; Neurourol Urodyn; 2015; 456-460; 34.
Pascual, I, et al.; Sacral nerve stimulation for fecal incontinence; Rev Esp Enferm Dig; 2011; 355-359; 103.
Patidar, N. et al.; Transcutaneous posterior tibial nerve stimulation in pediatric overactive bladder; A preliminary report; J Pediatr Urol; 2015; 351.e351-356; 11.
Pauls, RN, et al.; Effects of sacral neuromodulation on female sexual function; Int Urogynecol J Pelvic Floor Dysfunct; 2007; 391-395; 18.
Peeters, K, et al.; Long-term follow-up of sacral neuromodulation for lower urinary tract dysfunction; BJU Int; 2014; 789-794; 113.
Peirce, C, et al.; Central representation of the inferior rectal nerve of the rat; Dis Colon Rectum; 2010; 315-320; 53.
Pelaez, E. et al.; [Epidural spinal cord stimulation for interstitial cystitis]; Rev Esp Anestesiol Reanim; 2004; 549-552; 51;Abstract.
Pelliccioni, G, et al.; External and sphincter responses after S3 spinal root electrical stimulation; Neurourol Urodyn; 2006; 788-791; 25.
Pena, G, et al.; Cholinergic regulatory lymphocyles re-establish neuromodulation of innate immune responses in sepsis; J Immunol. 2011; 718-725; 187.
Peng, CW, et al.; Pudendal neuromodulation with a closed-loop control strategy to improve bladder functions in the animal study; Conf Proc IEEE Eng Med Biol Soc; 2013; 3626-3629; 2013.
Penson, DF; Re: Cost-effectiveness analysis of sacral neuromodulation and botulinum toxin a treatment for patients with idiopathis overactive bladder; J Urol; 2012; 2157-2158; 187.
Penson, DF; Re: Physician Use of Sacral Neuromodulation among Medicare Beneficiaries with Overactive Bladder and Urinary Retention; J Urol; 2016; 689; 195.
Perissinotto et al.; Transcutaneous Tibial Nerve Stimulation in the Treatment of Lower UrinaryTract Symptoms and its Impact on Health-Related Quality of Life in Patients With ParkinsonDisease; J Wound, Ostomy and Continence Nurses Society; 2015; 94-89: 42.
Perrigot, M. et al.; [Perineal electrical stimulation and rehabilitation in urinary incontinence and other symptoms of non-neurologic origin]; Ann Readapt Med Phys; 2008: 479-480; 51;Abstract.
Pescatori, LC, et al.; Sphincteroplasty for anal incontinence; Gastroenterol Rep (Oxf); 2014; 92-97; 2.
Peters, KM, et al.; Characterization of a clinical cohort of 87 women with interstitial cystitis/painful bladder syndrome; Urology: 2008; 634-640; 71.
Peters, KM, et al.; Chronic pudendal neuromodulation: expanding available treatment options for refractory urologic symptons; Neurourol Urodyn; 2010; 1267-1271; 29.
Peters, KM, et al.; Clinical outcomes of sacral neuromodulation in patients with neurologic conditions; Urology, 2013; 738-743; 81.
Peters, KM, et al.; Does patient age impact outcomes of neuromodulation?; Neurourol Urodyn; 2013; 30-36; 32.
Peters, KM, et al.; Effect of Sacral neuromodulation on Outcome Measures and Urine Chemokines in Interstitial Cystitis/Painful Bladder Syndrome Patients: Low Urin Tract Symptoms; 2015: 77-83: 7.
Peters, KM, et al.; Effect of Sacral Neuromodulation Rate on Overactive Bladder Symptoms; A Randomized Crossover Feasibility Study; Low Urin Tract Symptoms; 2013; 129-133; 5.

(56) References Cited

OTHER PUBLICATIONS

Peters, KM, et al.; Is sensory testing during lead placement crucial for achieving positive outcomes after sacral neuromodulation?; Neurourol Urodyn; 2011; 1489-1492; 30.
Peters, KM, et at.; Percutaneous tibial nerve stimulation for the long-term treatment of overactive bladder; 3-year results of the STEP study; J Urol; 2013; 2194-2201; 189.
Peters, KM, et al.; Predictors of reoperation after sacral neuromodulation: A single institution evaluation of over 400 patients; Neurourol Urodyn; 2015;Abstract.
Van Wunnik, BP, et al.; Patient experience and satisfaction with sacral neuromodulation; results of a single-center sample survey; Dis Colon Rectum; 2011; 95-100; 54.
Van Wunnik, BP, et al.; Sacral neuromodulation therapy; a promising treatment for adolescents with refractory functional constipation; Dis Colon Rectum; 2012; 278-285; 5.
Vasavada, SP, et al.; Neuromodulation techniques; a comparison of available and new therapies; Curr Urol Rep; 2007; 455-460; 8.
Vasdev, N, et al.; The surgical management of the refractory overactive bladder; Indian J Urol; 2010; 263-269; 26.
Veeratterapillay, R, et al.; Augmentation cystoplasty; Contemporary indications, techniques and complications; Indian J Urol; 2013; 322-327; 29.
Veit-Rubin, N, et al.; [Overactive bladder syndrome—a public health challenge]; Rev Med Suisse; 2015; 2016-2021; 11;Abstract.
Vigil, HR, et al.; Urinary tract infection in the neurogenic bladder; Transl Androl Urol; 2016; 72-87; 5.
Vignes, JR, et al.; Animal models of sacral neuromodulcation for detrusor overactivity; Neurourol Urodyn; 2009; 42594; 28.
Vignes, JR, et al.; Sacral neuromodulation as a functional treatment of bladder overactivity; Acta Neurochir Suppl; 2007; 315-322; 97;Abstract.
Vignes, JR, et al.; Sacral neuromodulation in lower urinary tract dysfunction; Adv Tech Stand Neurosurg; 2005; 177-224; 30;Abstract.
Wallace, JL, et al.; Lack of beneficial effect of a tachykinin receptor antagonist in experimental colitis; Regul Pept; 1998; 95-101; 73.
Walsh, IK, et al.; Non-invasive antidromic neurostimulation; a simple effective method for improving bladder storage; Neurourol Urodyn; 2001; 73-84; 20.
Walter, S; [Duloxetine. A new preparation for patients with urinary incontinence]; Ugeskr Laeger; 2005; 4553-4555; 167;Abstract.
Wang, Y, et al.; Neuromodulation reduces c-fos gene expression in spinalized rats; a double-blind randomized study; J Urol; 2000; 1966-1970; 163.
Wang, Y, et al.; Neuromodulation reduces uriniary frequency in rats with hydrochloric acid-induced cystitis; BJU Int; 2000; 726-730; 86.
Wark, HA, et al.; Restoration from acute urinary dysfunction using Utah electrode arrays implanted into the feline pudendal nerve: Neuromodulation; 2015: 317-323; 18.
Watanabe, JH, et al.; Cost analysis of interventions for antimuscarinic refractory patients with overactive bladder; Urology; 2010; 835-840; 76.
Wehbe, SA, et al.; Minimally invasive therapies for chronic pelvic pain syndrome; Curr Urol Rep; 2010; 276-265; 11.
Wehbe, SA, et al.; Sacral neuromodulations for female lower urinary tract, pelvic floor, and bowel disorders; Curr Opin Obstet Gynecol; 2010; 414-419; 22.
Weil, EH, et al.; Sacral root neuromodulation in the treatment of refractory urinary urge incontinence; a prospective randomized clinical trial; Eur Urol; 2000; 161-171; 37;Abstract.
Wein, AJ, et al.; Overactive bladder; a better understanding of pathophysiology, diagnosis and management; J Urol; 2006; S5-10; 175.
Wein, AJ; Diagnosis and treatment of the overactive bladder; Urology; 2003; 20-27; 62.
Wein, AJ; Re; inhibition of bladder overactivity by a combination of tibial neuromodulation and tramadol treatment in cats; J Urol; 2014; 868-869; 191.

Wein, AJ; Re; is on-demand sacral neuromodulation in patients with OAB syndrome a feasible therapy regime?; J Urol; 2013; 610-611; 189.
Wein, AJ; Re; Results of a Prospective, Randomized, Multicenter Study Evaluating Sacral Neuromodulation with InterStim Therapy Compared to Standard Medical Therapy at 6-Months in Subjects with Mild Symptoms of Overactive Bladder; J Urol; 2015; 1051-1052; 194.
Wenzler, DL, et al.; Proof of concept trial on changes in current perception threshold after sacral neuromodulation; Neuromodulation; 2015; 228-231; discussion 232; 18.
Wexner, SD. et al.; Current surgical strategies to treat fecal incontinence; Expert Rev Gastroenterol Hepatol; 2015; 1577-1589; 9;Abstract.
White, N, et al.; Overactive Bladder; Obstet Gynecol Clin North Am; 2016; 59-68; 43.
Whitmore, KE; Complementary and alternative therapies as treatment approaches for interstitial cystitis; Rev Urol; 2002; S28-35; 4 Suppl 1.
Wiklund CU, et al.; Modulation of cholinergic and substance P-like neurotransmission by nitric oxide in the guinea-pig ileum; Br J Pharmacol; 1993: 833-839: 110.
Wiklund, NP, et al.; Cholinergic neuromodulation by endothelin in guinea pig ileum; Neurosci Lett; 1989; 342-346; 101.
Wiklund, NP, et al.; Neuromodulation by adenine nucleotides, as indicated by experiments with inhibitors of nucleotide inactivation; Acta Physiol Scand; 1988; 217-223; 126:Abstract.
Williams, MJ, et al.; Self-Reported Medication Costs in Patients Receiving Sacral Neuromodulation for Overactive Bladder; Value Health; 2015; A352; 18.
Withington, J, et al.; The changing face of urinary continence surgery in England: a perspective from the Hospital Episode Statistics database; BJU Int; 2014; 268-277; 114.
Wolff, K, et al.; Function outcome and quality of life after stapled transanal rectal resection for obstructed defecation syndrome: Dis Colon Rectum; 2010; 881-888; 53.
Wood, LN, et al.; Urinary incontinence in women; Brnj; 2014; g4531; 349.
Wooldridge, LS; Percutaneous tibial nerve stimulation for the treatment of urinary frequency, urinary urgency, and urge incontinence; results from a community-based clinic; Urol Nurs; 2009; 177-185; 29.
Worsoe, J, et al., Turning off sacral nerve stimulation does not affect gastric and small intestinal motility in patients treated for faecal incontinence; Colorectal Dis; 2012; e713-720; 14.
Wosnitzer, MS, et al.; The use of sacral neuromodulation for the treatment of non-obstructive urinary retention secondary to Guillain-Barre syndrome; Int Urogynecol J Pelvic Floor Dysfunct; 2009; 1145-1147; 20.
Wu, JM, et al.; Patient preferences for different severities of and treatments for overactive bladder; Female Pelvic Med Reconstr Surg; 2011; 184-189; 17;Abstract.
Wyndaele, JJ, et al,; Conservative treatment of the neuropathic bladder in spinal cord injured patients; Spinal Cord; 2001; 294-300; 39.
Wyndaele, JJ, et al.; Influence of sacral neuromodulation on electrosensation of the lower urinary tract; J Urol; 2000; 221-224; 163.
Wyndaele, JJ; Clinical outcome of sacral neuromodulation in incomplete spinal cord injured patients suffering from neurogenic lower urinary tract symptoms; Spinal Cord; 2009; 427; 47.
Xiao, Z. et al.; Role of spinal GABAA receptors in pudendal inhibition of nociceptive and nonnociceptive bladder reflexes in cats; Am J Physiol Renal Physiol; 2014; F781-789, 306.
Xiao, Z, et al.; Somatic modulation of spinal reflex bladder activity mediated by nociceptive bladder afferent nerve fibers in cats; Am J Physiol Renal Physiol; 2014; F673-679; 307.
Yamanishi, T, et al.; Neuromodulation for the Treatment of Lower Urinary Tract Symptoms; Low Urin Tract Symptoms; 2015; 121-132; 7.
Yamanouchi, M. et el.; Integrative control of rectoanal reflex in guinea pigs through lumbar colonic nerves; Am J Physiol Gastrointest Liver Physiol; 2002; G148-156; 283.

(56) References Cited

OTHER PUBLICATIONS

Yang, G, et al.; Pudendal nerve stimulation and block by a wireless-controlled implantable stimulator in cats; Neuromodulation; 2014; 490-496; discussion 496; 17.
Yazdany, T, et al., Determing outcomes, adverse events, and predictors of success after sacral neuromodulation for lower urinary disorders in women; Int Urogynecol J; 2011; 1549-1554; 22.
Yih, JM, et al.; Changes in sexual functioning in women after neuromodulation for voiding dysfunction; J Sex Med; 2013; 2477-2483; 10.
Yoong, W, et al.; Neuromodulative treatment with percutaneous tibial nerve stimulation for intractable detrusor instability; outcomes following a shortened 6-week protocol; BJU Int; 2010; 1673-1676; 106.
Yun, AJ, et al.; Opening the floodgates: benign prostatic hyperplasia may represent another disease in the compendium of ailments caused by the global sympathetic bias that emerges with aging; Med Hypotheses; 2006; 392-394; 67.
Zabihi, N, el al.; Short-term results of bilateral S2-S4 sacral neuromodulation for the treatment of refractory interstitial cystitis, painful bladder syndrome, and chronic pelvic pain; Int Urogynecol J Pelvic Floor Dysfunct; 2008; 553-557; 19.
Zariffa, J, et al.; A Phase-Based Electrical Plethysmography Approach to Bladder Volume Measurement; Ann Biomed Eng; 2015.
Zecca, C, et al., Motor and sesensory responses after percutaneous tibial nerve stimulation in multiple sclerosis patients with lower urinary tract symptoms treated in daily practice: Eur J Neurol; 2014; 506-511; 21.
Zecca, C, et al.; Posterior tibial nerve stimulation in the management of lower urinary tract symptoms in patients with multiple sclerosis; Int Urogynecol J; 2015.
Zempleni, MZ, et al.; Cortical substrate of bladder control in SCI and the effect of peripheral pudendal stimulation; Neuroimage; 2010; 2983-2994; 49.
Zhang, F, et al.; Inhibition of bladder overactivity by a combination of tibial neuromodulation and tramadol treatment in cats; Am J Physiol Renal Physiol; 2012; F1576-1582; 302.
Zhang, F, et al,; Neural pathways involved in sacral neuromodulation of reflex bladder activity in cats; Am J Physiol Renal Physiol; 2013; F710-717; 304.
Zhang, N, et al,; Transcutaneous Neuromodulation at Posterior Tibial Nerve and ST36 for Chronic Constipation; Evid Based Complement Alternat Med; 2014; 560802; 2014.
Zhao, X. et al.; Diffused and sustained inhibitory effects of intestinal electrical stimulation on intestinal motility mediated via sympathetic pathway: Neuromodulation; 2014; 373-379; discussion 380; 17.
Zheng, J, et al.; [Sacral neuromodulation in the treatment of intractable constipation]; Zhonghua Wei Chang Wai Ke Za Zhi; 2014; 1175-1178; 17;Abstract.
Zhou, Y, et al.; Change of vanilloid receptor 1 following neuromodulation in rats with spinal cord injury; J Surg Res; 2002; 140-144; 107.
Zullo, MA, et al.; Sacral neuromodulation after stabilization of L2-S1 vertebrae with metallic fixation devices; is it feasible?; Int Urogynecol J; 2011; 373-375; 22.
Zvara, P, et al.; An animal model for the neuromodulation of neurogenic bladder dysfunction; Br J Urol. 1998; 267-271; 82.
Jezernik, S. et al.; Electrical stimulation for the treatment of bladder dysfunction: current status and future possibilities; Neurol Res; 2002; 413-430; 24;Abstract.
Jiang, CH; Modulation of the micturition reflex pathway by intravesical electrical stimulation: an experimental study in the rat; Neurourol Urodyn; 1998; 543-553; 17.
Jimenez-Toscano, M, et al.; Efficacy and quality of life after transcutaneous posterior tibial neuromodulation for faecal incontinence; Colorectal Dis; 2015; 718-723; 17.
Jin, H. et al.; Electrical neuromodulation at acupoint ST36 normalizes impaired colonic motility induced by rectal distenseion in dogs; Am J Physiol Gastrointest Liver Physiol; 2015; G368-376; 309.

Johnsen, NV, et al.; The role of electrical stimulation techniques in the management of the male patient with urgency incontinence; Curr Opin Urol; 2014; 560-565; 24.
Johnston, TE, et al.; Implantable FES system for upright mobility and bladder and bowel function for individuals with spinal cord injury; Spinal Cord; 2005; 713-723; 43.
Joussain, C, et al.; Electrical management of neurogenic lower urinary tract disorders; Ann Phys Rehabil Med; 2015; 245-250; 58.
Julius. F. et al.; Catheter tip granuloma associate with sacral region intrathecal drug administration; Neuromodulation; 2003; 225-228; 6.
Kachur, JF, et al.; Neuromodulation of guinea pig intestinal electrolyte transport by cholecystokinin octapeptide; Gastroenterology; 1991; 344-349; 100;Abstract.
Kacker, R, et al.; Electrical and mechanical office-based neuromodulation; Urol Clin North Am; 2013; 581-589; 40.
Kacker, R, et al.; Selection of ideal candidates for neuromodulation in refractory overactive bladder; Curr Urol Rep; 2010; 372-378; 11.
Kantartzis, K, et al.; Sacral neuromodulation and intravesical botulinum toxin for refractory overactive bladder; Curr Opin Obstet Gynecol; 2012; 331-336; 24.
Kantartzis, KL, et al.; Cost-effectiveness of test phase implantation strategies for InterSlim(R) sacral neuromodulation; Female Pelvice Med Reconstr Surg; 2013; 322-327; 19;Abstract.
Kapoor, DS, et al.; Combined urinary and faecal incontinence; Int Urogynecol J Pelvic Floor Dysfunct; 2005; 321-328; 16.
Karademir, K, et al.; A peripheral neuromodulation technique for curing detrusor overactivity; Stoller afferent neurostimulation; Scand J Urol Nephrol; 2005; 230-233; 39.
Karam, R, et al.; Real-Time Classification of Bladder Events for Effective Diagnosis and Treatment of Urinary Incontinence; IEEE Trans Biomed Eng; 2015.
Karmarkar, R, et al.; Emerging drugs for overactive bladder; Expert Opin Emerg Drugs; 2015; 613-624; 20;Abstract.
Karram, MM; Sacral neuromodulation: emerging technology with expanding indications; Int Urogynecol J; 2010; 1443;21.
Karsenty, G, et al.; Botulinum toxin type a injections into the trigone to treat idiopathic overactive bladder do not induce vesicoureteral reflux; J Urol; 2007; 1011-1014; 177.
Karsenty, G, et al.; Understanding detrusor sphincter dyssynergia—significance of chronology; Urology; 2005; 763-768; 66.
Katsuragi, T, et al.; Cholinergic neuromodulation by ATP, adenosine and its N6-substituted analogues in guinea-pig ileum; Clin Exp Pharmacol Physiol; 1985; 73-78; 12;Abstract.
Katsuragi, T. et al.; Involvement of dihydropyridine-sensitive Ca2+ channels in adenosine-evoked inhibition of acetylcholine release from guinea pig ileal preparation; J Neurochem; 1990; 363-369; 55.
Katsuragi, T, et al.; Possible transsynaptic cholinergic neuromodulation by ATP released from ileal longitudinal muscles of guinea pigs; Life Sci; 1993; 911-918; 53.
Kaufmann, S. et al.; Unilateral vs bilateral sacral neuromodulation in pigs with formalin-induced detrusor hyperactivity; BJU Int; 2009; 260-263; 103.
Kavia, R, et al.; A functional magnetic resonance imaging study of the effect of sacral neuromodulation on brain responses in women with Fowler's syndrome; BJU Int; 2010; 366-372; 105.
Kavia, R, et al.; Overactive bladder; J R Soc Promot Health; 2005; 176-179; 125;Abstract.
Kenefick, NJ; Sacral nerve neuromodulation for the treatment of lower bowel motility disorders; Ann R Coll Surg Engl; 2006; 617-623; 86.
Keppene, V, et al.; [Neuromodulation in the management of neurogenic lower urinary tract dysfunction]; Prog Urol; 2007; 609-615; 17;Abstract.
Kessler, TM, et al.; [Sacral neuromodulation for neurogenic bladder dysfunction]; Urologe A; 2012; 179-183; 51.
Kessler, TM, et al.; [Urodynamic phenomena in the aging bladder]; Urologe A; 2004; 542-546; 43.
Kessler, TM, et al.; Prolonged sacral neuromodulation testing using permanent leads: a more reliable patient selection methods?; Eur Urol; 2005; 660-665; 47.
Kessler, TM, et al.; Sacral neuromodulation for refractory lower urinary tract dysfunction: results of a nationwide registry in Switzerland; Eur Urol; 2007; 1357-1363; 51.

(56) References Cited

OTHER PUBLICATIONS

Kessler. TM, et al.; Urologists' referral attitude for sacral neuromodulation for treating refractory idiopathic overactive bladder syndrome: discrete choice experiment; Neurourol Urodyn; 2014; 1240-1246; 33.
Killinger, KA, et al.; Secondary changes in bowel function after successful treatment of voiding symptoms with neuromodulation; Neurourol Urodyn; 2011; 133-137; 30.
Kim, JH, et al.; Sacral nerve stimulation for treatment of intractable pain associated with cauda equina syndrome; J Korean Neurosurg Soc; 2010; 473-476; 47.
Kinder, MV, et al.; Neuronal circuitry of the lower urinary tract; central and peripheral neuronal control of the micturition cycle; Anat Embryol (Berl); 1995; 195-209; 192.
Kirkham, AP, et al.; Neuromodulation through sacral nerve roots 2 to 4 with a Finetech-Brindley sacral posterior and anterior root stimulator; Spinal Cord; 2002; 272-281; 40.
Kirkham, AP, et al.; The acute effects of continuous and conditional neuromodulation on the bladder in spinal cord injury; Spinal Cord; 2001; 420-428; 39.
Klingler, HC, et al.; Use of peripheral neuromodulation of the S3 region for treatment of detrusor overactivity: a urodynamic-based study; Urology; 2000; 766-771; 56.
Knowles; CH, et al.; Percutaneous tibial nerve stimulation versus sham electrical stimulation for the treatment of faecal incontinence in adults (CONFIDeNT): a double-blind, multicentre, pragmatic, parallel-group, randomised controlled trial, Lancet: 2015; 1640-1648; 386.
Knupfer, S, et al.; [Therapy-refractory overactive bladder: alternative treatment approaches]; Urologe A; 2011; 806-809; 50.
Knupfer, SC, et al.; Protocol for a randomized, placebo-controlled, double-blind clinical trial investigating sacral neuromodulation for neurogenic lower urinary tract dysfunction; BMC Urol; 2014; 65; 14.
Kocjancic, E, et al.; Sacral neuromodulation for urinary retention in a kidney-transplant patient; Urol Int; 2005; 187-188; 75.
Kohli, N, et al.; InterStim Therapy: A Contemporary Approach to Overactive Bladder; Rev Obstet Gynecol. 2009; 18-27; 2.
Kohli, N, et al.; Neuromodulation techniques for the treatment of the overactive bladder; Clin Obstet Gynecol; 2002; 218-232; 45.
Koldewijn, EL; [What to do if pills do not work fo urge incontinence—still many questions and ambiguities]; Ned Tijdschr Geneeskd; 2012; A5099; 156;Abstract.
Kosan, M, et al.; Alteration in contractile responses in human detrusor smooth muscle from obstructed bladders with overactivity; Urol Int: 2008; 193-200; 80.
Kovacevic, M, et al.; Reflex neuromodulation of bladder function elicited by posterior tibial nerve stimulation in anesthetized rats; Am J Physiol Renal Physiol; 2015; F320-329; 308.
Krames, E, et al.; Spinal cord stimulation reverses pain and diarrheal episodes of irritable bowel syndrome: a case report; Neuromodulation; 2004; 82-88; 7.
Krivoborodov, GG, et al.; [Afferent stimulation of the tibial nerve in patients with hyperactive bladder]; Urologiia; 2002; 36-39; ;Abstract.
Peters, KM, et al.; Randomized trial of percutaneous tibial nerve stimulation versus Sham efficacy in the treatment of overactive bladder syndrome: results from the SUmiT trial; J Urol; 2010; 1438-1443; 183.
Peters, KM; Alternative approaches to sacral nerve stimulation; Int Urogynecol J; 2010; 1559-1563; 21.
Peters, KM; Sacral neuromodulation is an effective treatment for interstitial cystitis/bladder pain syndrome: pro; J Urol; 2012; 2043-2044; 188.
Pettit, PD, et al.; Sacral neuromodulation: new applications in the treatment of female pelvic floor dysfunction; Curr Opin Obstet Gynecol; 2002; 521-525; 14.
Peyronnet, B, et al.; [Management of overactive bladder in women]; Prog Urol; 2015; 877-883; 25;Abstract.
Phe, V, et al.; How to define a refractory idiopathic overactive bladder?; Neurourol Urodyn; 2015; 42411; 34.

Possover, M, et al.; Neuromodulation of the Superior hypogastric plexus: a new option to treat bladder atonia secondary to radical pelvic surgery?; Surg Neurol; 2009; 573-576; 72.
Possover, M, et al.; Risks. symptoms, and management of pelvic nerve damage secondary to surgery for pelvic organ prolapse: a report of 95 cases; Int Urogynecol J; 2011; 1485-1490; 22.
Possover, M; A novel implantation technique for pudendal nerve stimulation for treatment of overactive bladder and urgency incontinence; J Minim Invasive Gynecol; 2014; 888-892; 21.
Possover M; Laparoscopic management of endopelvic etiologies of pudendal pain in 134 consecutive patients; J Urol; 2009; 1732-1736; 181.
Possover, M; The laparoscopic implantation of neuroprothesis to the sacral plexus for therapy of neurogenic bladder dysfunctions after failure of percutaneous sacral nerve stimulation; Neuromodulation; 2010; 141-144; 13.
Possover, M; The sacral LION procedure for recovery of bladder/rectum/sexual functions in paraplegic patients after explantation of a previous Finetech-Brindley controller; J Minim Invasive Gynecol; 2009; 98-101; 16.
Powell, CR, et al.; Long-term outcomes of urgency-frequency syndrome due to painful bladder syndrome treated with sacral neuromodulation and analysis of failures; J Urol; 2010; 173-176; 183.
Pucciani, F; A review on functional results of sphincter-saving surgery for rectal cancer: the anterior resection syndrome; Updates Surg; 2013; 257-263; 65.
Puccini, F, et al.; Sacral neuromodulation: an effective treatment for lower urinary tract symptoms in multiple sclerosis, Int Urogynecol J; 2016; 347-354; 27.
Qin, C, et al.; Is constant current or constant voltage spinal cord stimulation superior for the suppression of nociceptive visceral and somatic stimuli? A rat model; Neuromodulation; 2012: 132-142; discussion 143; 15.
Rahnama'i, MS, et al.; Evidence for prostaglandin E2 receptor expression in the intramural ganglia of the guinea pig urinary bladder; J Chem Neuroanat; 2015; 43-47; 64-65.
Rai, BP, et al.; Anticholinergic drugs versus non-drug active therapies for non-neurogenic overactive bladder syndrome in adults: Cochrane Database Syst Rev; 2012; Cd003193; 12;Abstract.
Ramage, L, et al.; A systematic review of sacral nerve stimulation for low anterior resection syndrome; Colorectal Dis; 2015; 762-771: 17.
Ramundo, JM, et al.; State of the science: pathology and management of the patient with overactive bladder; Ostomy Wound Manage; 2002; 22-27; 48.
Rana, MV, et al.; Tripolar spinal cord stimulation for the treatment of abdominal pain associated with irritable bowel syndrome; Neuromodulation; 2013; 73-77; discussion 77; 16.
Rashid, TG, et al.; Male incontinence: onabotulinum toxin A and sacral nerve stimulation; Curr Opin Urol; 2013; 545-551; 23.
Rasmussen, NT, et al.; Successful use of sacral neuromodulation after failed bladder augmentation: Can Urol Assoc J: 2009; E49-50; 3.
Ratto, C, et al.; Minimally invasive sacral neuromodulation implant technique: modifications to the conventional procedure; Dis Colon Rectum; 2003; 414-417; 46.
Ratto, C, et al.; Sacral neuromodulation in the treatment of defecation disorders; Acta Neurochir Suppl; 2007; 341-350; 97;Abstract.
Rawashdeh, YF, et al.; International Children's Continence Society's recommendations for therapeutic intervention in congenital neuropathic bladder and bowel dysfunction in children; Neurourol Urodyn; 2012; 615-620; 31.
Reese, JN, et al.; Role of spinal metabotropic glutamate receptor 5 in pudendal inhibition of the nociceptive bladder reflex in cats; Am J Physiol Renal Physiol; 2015; F832-838; 308.
Reitz, A, et al.; Topographic anatomy of a new posterior approach to the pudendal nerve for stimulation; Eur Urol; 2007; 1350-1355; discussion 1355-1356; 51.
Reyblat, P. et al.; Augmentation enterocystoplasty in overactive bladder; is there still a role?; Curr Urol Rep; 2010; 432-439; 11.

(56) References Cited

OTHER PUBLICATIONS

Riazimand, SH, et al.; A rat model for studying effects of sacral neuromodulation on the contractile activity of a chronically inflamed bladder; BJU Int; 2004; 158-163; 94.
Riazimand, SH, et al.; Interaction between neurotransmitter antagonists and effects of sacral neuromodulation in rats with chronically hyperactive bladder; BJU Int; 2005; 900-908; 96.
Richter, EO, et al.; Percutaneous cephalocaudal implantation of epidural stimulation electrodes over sacral nerve roots—a technical note on the importance of the lateral approach; Neuromodulation; 2011; 62-67; discussion 67; 14.
Ridout, AE, et al.; Tibial nerve stimulation for overactive bladder syndrome unresponsive to medical therapy; J Obstet Gynaecol; 2010; 111-114; 30.
Rigaud, J, et al.; [Specific treatments for painful bladder syndrome]; Prog Urol; 2010; 1044-1053; 20;Abstract.
Rimmer, CJ, et al.; Short-term Outcomes of a Randomized Pilot Trial of 2 Treatment Regimens of Transcutaneous Tibial Nerve Stimulation for Fecal Incontinence; Dis Colon Rectum; 2015; 974-985; 58.
Ripetti, V, et al.; Sacral nerve neuromodulation improves physical, psychological and social quality of life in patients with fecal incontinence; Tech Coloproctol; 2002; 147-152; 6.
Rittenmeyer. H; Sacral nerve neuromodulation (InterStim). Part 1. Review of the InterStim system; Urol Nurs; 2008; 15-20; 28.
Robaina Padron, FJ; [Surgical neuromodulation; new frontiers in neurosurgery]; Neurocirugia (Astur); 2008; 143-155; 19;Abstract.
Robinson, D, et al.; Overactive bladder: diagnosis and management; Maturitas; 2012; 188-193; 71.
Robinson, D, et al.; The management of overactive bladder refractory to medical therapy; Maturitas; 2013; 101-104; 75.
Robinson, D, et al.; The medical management of refractory overactive bladder; Maturitas; 2013; 386-390; 74.
Rogers, MJ, et al.; Propranolol, but not naloxone, enhances spinal reflex bladder activity and reduces pudendal inhibition in cats; Am J Physiol Regul Integr Comp Physiol; 2015; R42-49; 308.
Rogers, MJ, et al.; Role of glycine in nociceptive and non-nociceptive bladder reflexes and pudendal afferent inhibition of these reflexes in cats; Neurourol Urodyn; 2015;Abstract.
Romero Maroto, J, et al.; [Techniques and current practice of urodynamics, Problems and traps]; Acias Urol Esp; 2003; 75-91; 27;Abstract.
Roth, TM; Blunt trauma leafding to delayed extrusion of sacral nerve implant; Int Urogynecol J Pelvic Floor Dysfunct; 2009; 735-737; 20.
Roth, TM; Sacral neuromodulation and cardiac pacemakers; Int Urogynecol J; 2010; 1035-1037; 21.
Roth, TM; Safe Simultaneous Use of Sacral Neuromodulation and Vagal Nerve Stimulation; Female Pelvic Med Reconstr Surg; 2016; e1-2; 22;Abstract.
Roth, TM; Subcapsular relocation for sacral neuromodulation pulse generator implant revision; Neuromodulation; 2010; 145-146; 13.
Roupret, M, et al.; Sacral neuromodulation for refractory detrusor overactivity in women with an artificial urinary sphincter; J Urol; 2004; 236-239; 172.
Rovner, ES; Treatment of urinary incontinence; Curr Urol Rep; 2000; 235-244; 1.
Ruffion, A, et al.; [Sacral root neuromodulation for the treatment of urinary incontinence reported to detrusor hyperactivity]; Neurochirurgie; 2003; 377-382; 49;Abstract.
Ruffion, A. et al., [Two indications for bilateral neuromodulation]; Prog Urol; 2003; 1394-1396; 13;Abstract.
Saber-Khalaf, M, et al.; Sacral neuromodulation outcomes in male patients with chronic urinary retention; Neuromodulation; 2015; 329-334; discussion 334; 18.
Sadiq, A, et al.; Management of neurogenic lower urinary tract dysfuntion in multiple sclerosis patients; Curr Urol Rep; 2015; 44; 16.

Sahai, A, et al.; Neurogenic detrusor overactivity in patients with spinal cord injury; evaluation and management; Curr Urol Rep; 2011; 404-412; 12.
Sajadi, KP, et al.; Bladder augmentation and urinary diversion for neurogenic LUTS: current indications; Curr Urol Rep; 2012; 389-393; 13.
Sajadi, KP, et al.; Overactive bladder after sling surgery; Curr Urol Rep; 2010; 366-371; 11.
Sakas, DE, et al., An introduction to operative neuromodulation and functional neuroprosthetics, the new frontiers of clinical neuroscience and biotechnology; Acta Neurochir Suppl; 2007; 42439; 97;Abstract.
Sancaktar, M. et .; The outcome of adding peripheral neuromodulation (Stoller afferent neuro-stimulation) to anti-muscarinic therapy in women with severe overactive bladder; Gynecol Endocrinol; 2010; 729-732; 26.
Sanford, MT, et al.; Neuromodulation in neurogenic bladder; Transl Androl Urol; 2016; 117-126; 5.
Scaglia, M, et al.; Fecal incontinence treated with acupuncture—a pilot study; Auton Neurosci; 2009; 89-92; 145.
Scheepens, WA, et al.; [Neuromodulation and neurostimulation in urology]; Ned Tijdschr Geneeskd; 2001; 1730-1734; 145;Abstract.
Scheepens, WA, et al.; Predictive factors for sacral neuromodulation in chronic lower urinary tract dysfunction; Urology; 2002; 598-602; 60.
Scheepens, WA, et al.; Unilateral versus bilateral sacral neuromodulation in patients with chronic voiding dysfunction; J Urol; 2002; 2046-2050; 168.
Scheepens, WA, et al.; Urodynamic results of sacral neuromodulation correlate with subjective improvement in patients with an overactive bladder; Eur Urol; 2003; 282-287; 43.
Scheiner, DA, et al.; [Interstitial cystitis/bladder pain syndrome (IC/BPS)]; Praxis (Bern 1994); 2015; 909-918; 104.
Schijns, O. et al.; Development and characterization of [123I]iodotiagabine for in-vivo GABA-transporter imaging; Nucl Med Commun; 2013; 175-179; 34;Abstract.
Schmidt, RA, et al.; Neurostimulation and neuromodulation: a guide to selecting the right urologic patient; Eur Urol; 1998; 23-26; 34 Suppl 1;Abstract.
Schneider, MP, et al.; Tibial Nerve Stimulation for Treating Neurogenic Lower Urinary Tract Dysfunction: A Systematic Review: Eur Urol; 2015; 859-887; 68.
Schonberger, B; [Bladder dysfunction and surgery in the small pelvis. Therapeutic possibilities]; Urologe A; 2003; 1569-1575; 42.
Schreiber, KL, et al.; Evidence for neuromodulation of enteropathogen invasion in the intestinal mucosa; J Neuroimmune Pharmacol; 2007; 329-337; 2.
Schultz-Lampel, D, et al.; Experimental results on mechanisms of action of electrical neuromodulation in chronic urinary retention; World J Urol; 1983; 301-304; 16.
Schurch, B, et al.; Dysfunction of lower urinary tract in patients with spinal cord injury; Handb Clin Neurol; 2015; 247-267; 130.
Schurch, B, et al.; Electrophysiological recordings during the peripheral nerve evaluation (PNE) test in complete spinal cord injury patients; World J Urol; 2003; 319-322; 20.
Schwalenberg, T, et al.; [Sacral neuromodulation in urology—development and current status]; Aktuelle Urol; 2012; 39-48; 43;Abstract.
Schwen, Z, et al.; Combination of foot stimulation and tolterodine treatment eliminates bladder overactivity in cats; Neurourol Urodyn; 2014; 1266-1271; 33.
Schwen, Z, et al.; Inhibition of bladder overactivity by duloxetine in combination with foot stimulation of WAY-100635 treatment in cats: Am J Physiol Renal Physiol; 2013; F1663-1668; 305.
Schwen, Z, et al.; Involvement of 5-HT3 receptors in pudendal inhibition of bladder overactivity in cats; Am J Physiol Renal Physiol; 2013; F663-671; 305.
Seif, C, et al.; [Pudendal nerve stimulation therapy of the overactive bladder—an alternative to sacral neuromodulation?]; Aktuelle Urol; 2005; 234-238; 36;Abstract.
Seif, C, et al.; [Use of permanent electrodes in the peripheral nerve evaluation test (PNE-Test) in comparison to conventional wire electrodes]; Aktuelle Urol; 2006; 277-280; 37;Abstract.

(56) References Cited

OTHER PUBLICATIONS

Seif, C, et al.; Findings with Bilateral Sacral Neurostimulation: Sixty-two PNE-Tests in Patients with Neurogenic and Idiopathic Bladder Dysfunctions; Neuromodulation; 2004; 141-145; 7.
Seif, C, et al.; Improved sacral neuromodulation in the treatment of the hyperactive detrusor: signal modification in an animal model; BJU Int; 2003; 711-715; 91.
Seth, A, et al.; What's new in the diagnosis and management of painful bladder syndrome/interstitial cystitis?; Curr Urol Rep; 2008; 349-357; 9.
Sevcencu, C; A review of electrical stimulation to treat motility dysfunctions in the digestive tract: effects and stimulation patterns; Neuromodulation; 2007; 85-99; 10.
Sevcencu, C; Gastrointestinal mechanisms activated by electrical stimulation to treat motility dysfunctions in the digestive tract: a review; Neuromodulation; 2007; 100-112; 10.
Shafik, A, et al.; Percutaneous peripheral neuromodulation in the treatment of fecal incontinence: Eur Surg Res; 2003; 103-107; 35.
Shah, P, et al.; Unique spatiotemporal neuromodulation of the lumbosacral circuitry shapes locomotor success after spinal cord injury; J Neurotrauma; 2016;Abstract.
Shaker, H, et al.; Role of C-afferent fibres in the machanism of action of sacral nerve root neuromodulation in chronic spinal cord injury; BJU Int: 2000; 905-910; 85.
Shaker, H, et ai.; Sacral root neuromodulation in the treatment of various voiding and storage problems; Int Urogynecol J Pelvic Floor Dysfunct; 1999; 336-343; 10;Abstract.
Shaker, HS, et al.; Sacral nerve root neuromodulation: an effective treatment for refractory urge incontinence J Urol; 1998; 1516-1519; 159.
Shaker, HS, et al.; Sacral root neuromodulation in idiopathic nonobstructive chronic urinary retention: J Urol; 1998; 1476-1478; 159.
Shalmon, DF, et al.; Sacral nerve stimulation reduces elevated urinary nerve growth factor levels in women with symptomatic detrusor overactivity; Am J Obstet Gynecol: 20014; 561,e561-565; 211.
Shamliyan, T, et al.; Prevention of urinary and fecal incontinence in adults; Evid Rep Technol Assess (Full Rep); 2007; 1-379; ;Abstract.
Sharma, A, et al.; Review of sacral neuromodulation for management of constipation; Surg Innov; 2013; 614-624; 20.
Sharma, A, et al.; Sacral neuromodulation for the management of severe constipation; development of a constipation treatment protocol; Int J Colorectal Dis; 2011; 1583-1587; 26.
Shen, B, et al.; Neuromodulation of bladder activity by stimulation of feline pudendal nerve using a transdermal amplitude modulated signal (TAMS); Neurourol Urodyn; 2011; 1686-1694; 30.
Shepherd, JP, et al.; InterStim Sacral Neuromodulation and Botox Botulinum-A Toxin Intradetrusor Injections for Refractory Urge Urinary Incontinence: A Decision Analysis Comparing Outcomes Including Efficacy and Complications; Female Pelvic Med Reconstr Surg; 2011; 199-203; 17;Abstract.
Sherif, H, et al.; Posterior tibial nerve stimulation as treatment for the overactive bladder; Arab J Urol; 2013; 131-135; 11.
Sheriff, MK, et al.; Neuromodulation of detrusor hyper-reflexia by functional magnetic stimulation of the sacral roots; Br J Urol; 1996; 39-46; 78;Abstract.
Sherman, ND, et al.; Current and future techniques of neuromodulation by bladder dysfunction; Curr Urol Rep; 2007; 448-454; 8.
Tai, C, et al.; Irritation induced bladder overactivity is suppressed by tibial nerve stimulation in cats; J Urol; 2011; 326-330; 186.
Tai, C, et al.; Prolonged poststimulation inhibition of bladder activity induced by tibial nerve stimulation in cats; Am J Physiol Renal Physiol; 2011; F385-392; 300.
Takahashi, S, et al.; Overactive bladder: magnetic versus electrical stimulation: Curr Opin Obstet Gynecol; 2003; 429-433; 15.
Tanagho, EA; Concepts of neuromodulation: Neurourol Urodyn; 1993; 487-488; 12.
Tanagho, EA; Neuromodulation in the management of voiding dysfunction in children; J Urol; 1992; 655-657; 148;Abstract.

Tang, H, et al.; Combination of sacral neuromodulation and tolterodine for treatment of idiopathic overactive bladder in women; a clinical trial; Urol J; 2014; 1800-1805; 11.
Taweel, WA, et al.; Neurogenic bladder in spinal cord injury patients; Res Rep Urol; 2015; 85-99; 7.
Thin, NN, et al.; Randomized clinical trial of sacral versus percutaneous tibial nerve stimulation in patients with faecal incontinence; Br J Surg; 2015; 349-358; 102.
Thin, NN, et al.; Systematic review of the clinical effectiveness of neuromodulation in the treatment of faecal incontinence; Br J Surg: 2013; 1430-1447; 100.
Thomas, GP, et al.; A pilot study of transcutaneous sacral nerve stimulation for faecal incontinence; Colorectal Dis; 2013; 1406-1409; 15.
Thomas, GP, et al.; Sacral nerve stimulation for faecal incontinence secondary to congenital imperforate anus; Tech Coloproctol; 2013; 227-229; 17.
Thompson, JH, et al.; Sacral neuromodulation: Therapy evolution; Indian J Urol; 2010; 379-384; 26.
Thoua, NM, et al.; Internal anal sphincter atrophy in patients with systemic sclerosis; Rheumatology (Oxford); 2011; 1596-1602; 50.
Tian, Y, et al.; Inhibitory Effect and Possible Mechanism of Intraurethral Stimulation on Overactive Bladder in Female Rats; Int Neurourol J; 2015; 151-157; 19.
Tirlapus, SA, et al.; Nerve stimulation for chronic pelvic pain and bladder pain syndrome: a systematic review; Acta Obstet Gynecol Scand; 2013; 881-887; 92.
Tjandra, JJ, et al.; Sacral nerve stimulation is more effective than optimal medical therapy for severe fecal incontinence: a randomized. controlled study; Dis Colon Retum; 2008; 494-502; 51.
Tomonori Yamanishi et al.; Neuromodulation for the Treatment of Lower Urinary TractSymptoms; Low Urin Tract Symptoms; 2015; 121-132; 7.
Traynor, TR, et al.; Neuromodulation of ion transport in porcine distal colon: NPY reduces secretory actions of leukotrienes; Am J Physiol. 1995; R426-431; 269;Abstract.
Trevizol, AP, et al.; Trigeminal Nerve Stimulation (TNS) for the Treatment of Irritable Bowel Syndrome in an Elderly Patient with Major Depressive Disorder: A Case Study; Brain Stimul; 2015; 1235-1236; 8.
Turner, WH, et al.; Smooth muscle of the bladder in the normal and the diseased state: pathophysiology, diagnosis and treatment; Pharmacol. Ther; 1997; 77-110; 75.
Ullah, S, et al.; Temporary gastric neuromodulation for intractable nausea and vomiting; Ann R Coll Surg Engl; 2011; 624-628; 93.
Uludag, O, et al.; [Sacral neuromodulation is effective in the treatment of fecal incontinence with intact sphincter muscles: a prospective study]; Ned Tijdschr Geneeskd; 2002; 989-993; 146;Abstract.
Uludag, O, et al.; Sacral neuromodulation in patients with fecal incontinence: a single-center study; Dis Colon Rectum; 2004; 1350-1357; 47.
Uludag, O, et al.; Sacral neuromodulation: does it affect the rectoanal angle in patients with fecal incontinence?; World J Surg; 2010; 1109-1114; 34.
Uludag, O, et al.; Sacral neuromodulation: long-term outcome and quality of life in patients with faecal incontinence; Colorectal Dis; 2011; 1162-1166; 13.
Uludag, O, et al.; Sacral neuromodulation; does it affect colonic transit time in patients with faecal incontinence?; Colorectal Dis; 2006; 318-322; 8.
Unger, CA, et al.; Fecal incontinence: the role of the urologist; Curr Urol Rep; 2014; 388; 15.
Unwala, DJ, et al.; Repeated botulinum toxin injection for idiopathic overactive bladder: will chemodenervation become a long-term solution?: Curr Urol Rep; 2007; 419-424; 8.
Uranga, A, et al.; An integrated implantable electrical sacral root stimulator for bladder control; Neuromodulation; 2002; 238-247; 5.
Vaarala, MH, et al.; Sacral neuromodulation in urological indications: the Finnish experience; Scand J Urol Nephrol; 2011; 46-51; 45.

(56) References Cited

OTHER PUBLICATIONS

Vaizey, CJ, et al.; Effects of short term sacral nerve stimulation on anal and rectal function in patients with anal incontinence; Gut; 1999; 407-412; 44.
Vallet, C, et al.; Sacral nerve stimulation for faecal incontinence: response rate, satisfaction and the value of preoperative investigation in patient selection; Colorectal Dis; 2010; 247-253; 12.
Van Balken, MR, et al.; Prognostic factors for successful percutaneous tibial nerve stimulation; Eur Urol; 2006; 360-365; 49.
Van Balken, MR, et al.; Sexual functioning in patients with lower urinary tract dysfunction improves after percutaneous tibial nerve stimulation; Int J Impot Res: 2006; 470-475; discussion 476; 18.
Van Balken, MR, et al.; The use of electrical devices for the treatment of bladder dysfunction: a review of methods; J Urol; 2004; 846-851; 172.
Van Balken, MR; Percutaneous tibial nerve stimulation: the Urgent PC device; Expert Rev Med Devices; 2007; 693-698; 4.
Van Der AA, HE, et al.; Sacral anterior root stimulation for bladder control: clinical results; Arch Physiol Biochem; 1999; 248-256; 107.
Van Der Pal, F, et al.; Current opinion on the working mechanisms of neuromodulation in the treatment of lower urinary tract dysfunction; Curr Opin Urol, 2006; 261-267; 16.
Van Der Pal, F, et al.; Implant-Driven Tibial Nerve Stimulation in the Treatment of Refractory Overactive Bladder Syndrome; 12-Month Follow-up; Neuromodulation; 2006; 163-171; 9.
Van Kerrebroeck, P; Editorial comment re: Killinger et al. "Secondary changes in bowel function after successful treatment of voiding symptoms with neuromodulation"; Neurourol urodyn; 2011; 1403; 30.
Van Kerrebroeck, PE. et al.; Results of sacral neuromodulation therapy for urinary voiding dysfunction: outcomes of a prospective, worldwide clinical study; J Urol; 2007; 2029-2034; 178.
Van Kerrebroeck, PE; Advances in the role of sacral nerve neuromodulation in lower urinary tract symptoms; Int Urogynecol J: 2020; S467-474; 21 Suppl 2.
Van Kerrebroeck, PE; Neuromodulation and other electrostimulatory techniques; Scand J Urol Nephrol Suppl; 2002; 82-86.
Van Kerrebroeck, PE; The role of electrical stimulation in voiding dysfunction; Eur Urol. 1998; 27-30; 34 Suppl 1;Abstract.
Van Koeveringe, GA, et al.; Detrusor underactivity: a plea for new approaches to a common bladder dysfunction; Neurourol Urodyn; 2011; 723-728; 30.
Van Ophoven, A, et al.; [The future of invasive neuromodulation: new techniques and expanded indications]; Urologe A; 2012; 212-216; 51.
Van Voskuilen, AC, et al.; Long term results of neuromodulation by sacral nerve stimulation for lower urinary tract symptoms: a retrospective single center study; Eur Urol; 2006; 366-372; 49.
Van Voskuilen, AC, et al.; Medium-term experience of sacral neuromodulation by tined lead implantation; BJU Int; 2007; 107-110; 99.
Van Wunnik, BP, et al.; Cost-effectiveness analysis of sacral neuromodulation for faecal incontinence in The Netherlands, Colorectal Dis; 2012; e807-814; 14.
Van Wunnik, BP, et al.; Neuromodulation for constipation: sacral and transcutaneous stimulation; Best Pract Res Clin Gastroenterol; 2011; 181-191; 25.
Desrosiers, L, et al.; Urogynecologic conditions: interstitial cystitis/painful bladder syndrome; FP Essent; 2015; 17-22; 430;Abstract.
Devane, LA, et al.; Acute lumbosacral nerve stimulation does not affect anorectal motor function in a rodent model; Neurogastroenterol Motil; 2016; 358-363; 28.
Devroede, G, et al.; Quality of life is markedly improved in patients with fecal incontinence after sacral nerve stimulation; Female Pelvic Med Reconstr Surg; 2012; 103-112; 18;Abstract.
Di Giovangiulio, M, et al.; The Neuromodulation of the Intestinal Immune System and Its Relevance in Inflammatory Bowel Disease; Front Immunol; 2015; 590; 6.

Dijkema, HE, et al.; [Initial experiences with neuromodulation as treatment for incontinence and micturition disorders in The Netherlands]; Ned Tijdschr Geneeskd; 1992; 88-90; 136;Abstract.
Dijkema, HE, et al.; Neuromodulation of sacral nerves for incontinence and voiding dysfunctions. Clinical results and complications; Eur Urol; 1993; 72-76; 24;Abstract.
Dmochowski, R; Neuromodulation and the urinary tract—are we over the rainbow or have we simply stepped through the looking glass?; J Urol; 2007; 1844-1845; 178.
Donon, L, et al.; [Sacral neuromodulation: results of a monocentric study of 93 patients]; Prog Urol; 2014; 1120-1131; 24;Abstract.
Dorflinger, A, et al.; Voiding dysfunction; Curr Opin Obstet Gynecol; 2001; 507-512; 13.
Doumouchtsis, SK, et al.; Female voiding dysfunction; Obstet Gynecol Surv; 2008; 519-526; 63.
Drake, MJ; Management and rehabilitation of neurologic patients with lower urinary tract dysfunction; Handb Clin Neurol; 2015; 451-468; 130.
Drossaerts, J, et al.; Screening for depression and anxiety in patients with storage or voiding dysfunction: A retrospective cohort study predicting outcome of sacral neuromodulation; Neurourol Urodyn; 2015;Abstract.
Drossaerts, J, et al.; The value of urodynamic tools to guide patient selection in sacral neuromodulation; World J Urol; 2015; 1889-1895; 33.
Dudding, TC, et al.; Sacral nerve stimulation for faecal incontinence: optimizing outcome and managing complications; Colorectal Dis; 2011; e196-202; 13.
Dudding, TC, et al.; Sacral nerve stimulation for faecal incontinence: patient selection, service provision and operative technique; Colorectal Dis; 2011; e187-195; 13.
Dudding, TC, et al.; Sacral nerve stimulation: an effective treatment for chronic functional anal pain?; Colorectal Dis; 2013; 1140-1144; 15.
Dudding, TC; Future indications for sacral nerve stimulation; Colorectal Dis; 2011; 23-28; 13 Suppl 2.
Duelund-Jakobsen, J, et al.; Baseline factors predictive of patient satisfaction with sacral neuromodulation for diopathic fecal incontinence; Int J Colorectal Dis; 2014; 793-798; 29.
Duthie, J, et al.; Botulinum toxin injections for adults with overactive bladder syndrome; Cochrane Database Syst Rev; 2007; Cd005493; ;Abstract.
Duthie, JB, et al.; Botulinum toxin injections for adults with overactive bladder syndrome; Cochrane Database Syst Rev; 2011; Cd005493.
Duve H, et al.; Distribution and functional significance of Leucallatostatins in the blowfly Calliphora vomitoria; Cell Tissue Res; 1994; 367-379; 276.
Dwyer, ME, et al.; The dysfunctional elimination syndrome in children—is sacral neuromodulation worth the trouble?; J Urol; 2012; 1076-1077; 188.
Elkelini, MS, et al.; Mechanism of action of sacral nerve stimulation using a transdermal amplitude-modulated signal in a spinal cord injury rodent model; Can Urol Assoc J; 2012; 227-230; 6.
Elkelini, MS, et al.; Safety of MRI at 1.5Tesla in patients with implanted sacral nerve neurostimulator; Eur Urol; 2006; 311-316; 50.
Ellsworth, P, et al.; Neurogenic detrusor overactivity: an update on management options; R I Med J (2013); 2013; 38-40; 96.
Ellsworth, P, et al.; Update on the pharmacologic management of overactive bladder: the present and the future; Urol Nurs; 2010; 29-38, 53; 30.
Elneil, S, et al.; Optimizing the duration of assessment of stage-1 sacral neuromodulation in nonobstructive chronic urinary retention; Neuromodulation; 2014; 66-70; discussion 70-61; 17.
Elneil, S; Urinary retention in women and sacral neuromodulation; Int Urogynecol J; 2010; S475-483; 21 Suppl 2.
Elser, DM; Stress urinary incontinence and overactive bladder syndrome: current options and new targets for management; Postgrad Med; 2012; 42-49; 124;Abstract.
Evans, RJ; Sacral neuromodulation is an effective treatment for interstitial cystitis/bladder pain syndrome: con; J Urol; 2012; 2044-2045; 188.

(56) References Cited

OTHER PUBLICATIONS

Everaert, K, et al.; Sacral nerve stimulation for pelvic floor and bladder dysfunction in adults and children; Neuromodulation; 2005; 186-187; 8.
Everaert, K, et al.; The urodynamic evaluation of neuromodulation in patients with voiding dysfunction; Br J Urol; 1997; 702-707; 79.
Evers, J, et al.; Effects of stimulation frequency and intensity in sacral neuromodulation on anorectal inputs to the somatosensory cortex in an experimental model; Br J Surg; 2014; 1317-1328; 101.
Evers, J, et al.; Reversal of sensory deficit through sacral neuromodulation in an animal model of fecal incontinence; Neurogastroenterol Motil; 2016;Abstract.
Fall, M, et al.; EAU guidelines on chronic pelvic pain; Eur Urol; 2004; 681-689; 46.
Fall, M, et al.; EAU guidelines on chronic pelvic pain; Eur Urol; 2010; 35-48; 57.
Falletto, E, et al.; Is sacral nerve stimulation an effective treatment for chronic idiopathic anal pain?; Dis Colon Rectum; 2009; 456-462; 52.
Falletto, E, et al.; Sacral neuromodulation for bowel dysfunction: a consensus statement from the Italian group; Tech Coloproctol; 2014; 53-64; 18.
Fang, Q, et al.; [Morphological study on the role of ICC-like cells in detrusor neuro-modulation of rat urinary bladder]; Zhonghua Wai Ke Za Zhi; 2008; 1542-1545; 46.
Fariello, JY, et al.; Sacral neuromodulation stimulation for IC/PBS, chronic pelvic pain, and sexual dysfunction; Int Urogynecol J; 2010; 1553-1558; 21.
Faucheron, JL, et al.; Sacral neuromodulation for bowel dysfunction; Tech Coloproctol; 2014; 42433; 18.
Faucheron, JL; [Anal incontinence]; Presse Med; 2008; 1447-1462; 37;Abstract.
Feler, CA, et al.; Sacral neuromodulation for chronic pain conditions; Anesthesiol Clin North America; 2003; 785-795; 21.
Felt-Bersma, RJ, et al.; Temperature-controlled radiofrequency energy (SECCA) to the anal canal for the treatment of faecal incontinence offers moderate improvement; Eur J Gastroenterol Hepatol; 2007; 575-580; 19;Abstract.
Ferhi, K, et al.; [Results of sacral posterior neuromodulation on voiding disorders and impact on sexuality based on a single-center study]; Prog Urol; 2008; 160-166; 18;Abstract.
Ferroni, MC, et al.; Role of the brain stem in tibial inhibition of the micturition reflex in cats; Am J Physiol Renal Physiol; 2015; F242-250; 309.
Ferulano, GP, et al.; [Sacral neuromodulation in fecal continence disorders]; Recenti Prog Med; 2002; 403-409; 93; Abstract.
Finazzi-Agro, E, et al.; Percutaneous tibial nerve stimulation produces effects on brain activity: study on the modifications of the long latency somatosensory evoked potentials; Neurourol Urodyn; 2009; 320-324; 28.
Findlay, JM, et al.; Peripheral neuromodulation via posterior tibial nerve stimulation—a potential treatment for faecal incontinence?; Ann R Coll Surg Engl; 2010; 385-390; 92.
Firoozi, F, et al.; Increasing patient preparedness for sacral neuromodulation improves patient reported outcomes despite leaving objective measures of success unchanged; J Urol; 2013; 594-597; 190.
Fjorback, MV, et al.; A portable device for experimental treatment of neurogenic detrusor overactivity; Neuromodulation; 2003; 158-165; 6.
Foditsch, EE, et al.; Laparoscopic placement of a tined lead electrode on the pudendal nerve with urodynamic monitoring of bladder function during electrical stimulation: an acute experimental study in healthy female pigs; Springerplus; 2014; 309; 3.
Foon, R, et al.; The overactive bladder; Ther Adv Urol; 2010; 147-155; 2.
Ford, AP, et al.; P2X3 receptors and sensitization of autonomic reflexes; Auton Neurosci; 2015; 16-24; 191.
Fowler, CJ; The perspective of a neurologist on treatment-related research in fecal and urinary incontinence; Gastroenterology; 2004; S172-174; 126.
Franzen, K, et al.; Surgery for urinary incontinence in women 65 years and older: a systematic review; Int Urogynecol J; 2015; 1095-1102; 26.
Fraser, MO, et al.; Neural control of the urethra and development of pharmacotherapy for stress urinary incontinence; BJU Int; 2003; 743-748; 91.
Freeman, RM, et al.; Overactive bladder; Best Pract Res Clin Obstet Gynaecol; 2005; 829-841; 19.
French, JS, et al.; What do spinal cord injury consumers want? A review of spinal cord injury consumer priorities and neuroprosthesis from the 2008 neural interfaces conference; Neuromodulation; 2010; 229-231; 13.
Frokjaer, JB, et al.; Modulation of vagal tone enhances gastroduodenal motility and reduces somatic pain sensitivity; Neurogastroenterol Motil; 2016.
Fu, G, et al.; [Neuromodulation for treatment for neurogenic bowel dysfunction]; Zhonghua Wai Ke Za Zhi; 2009; 128-131; 47.
Gaj, F, et al.; [Chronic pelvic pain treatment with posterior tibial nerve stimulation]; Clin Ter; 2011; e111-114; 162; Abstract.
Gajewski, JB, et al.; The long-term efficacy of sacral neuromodulation in the management of intractable cases of bladder pain syndrome: 14 years of experience in one centre; BJU Int; 2011; 1258-1264; 107.
Game, X, et al.; [Alternative treatments for interstitial cystitis]; Prog Urol; 2009; 357-363; 19;Abstract.
Game, X, et al.; Outcome after treatment of detrusor-sphincter dyssynergia by temporary stent; Spinal Cord; 2008; 74-77; 46.
Game, X; [Sacral neuromodulation and sexuality]; Prog Urol; 2008; 167; 18;Abstract.
Ganio, E, et al.; Neuromodulation for fecal incontinence: outcome in 16 patients with definitive implant. The initial Italian Sacral Neurostimulation Group (GINS) experience; Dis Colon Rectum; 2001; 965-970; 44.
George, E, et al.; Use of combined anticholinergic medication and sacral neuromodulation in the treatment of refractory overactive bladder; Female Pelvic Med Reconstr Surg; 2011; 97-99; 17;Abstract.
Ghazwani, YQ, et al.; Efficacy of sacral neuromodulation in treatment of bladder pain syndrome: long-term follow-up; Neurourol Urodyn; 2011; 1271-1275; 30.
Ghiselli, R, et al.; Nitric oxide synthase expression in rat anorectal tissue after sacral neuromodulation; J Surg Res; 2012; 29-33; 176.
Giarenis, I, et al.; Management of refractory overactive bladder; Minerva Ginecol; 2013; 41-52; 65;Abstract.
Giarenis, I, et al.; Managing urinary incontinence: what works?; Climacteric; 2014; 26-33; 17 Suppl 2;Abstract.
Gibbons, SJ, et al.; Review article: carbon monoxide in gastrointestinal physiology and its potential in therapeutics; Aliment Pharmacol Ther; 2013; 689-702; 38.
Gill, BC, et al.; Improved sexual and urinary function in women with sacral nerve stimulation; Neuromodulation; 2011; 436-443; discussion 443; 14.
Gill, BC, et al.; Improvement of bowel dysfunction with sacral neuromodulation for refractory urge urinary incontinence; Int Urogynecol J; 2012; 735-741; 23.
Gleason, JL, et al.; Sacral neuromodulation effects on periurethral sensation and urethral sphincter activity; Neurourol Urodyn; 2013; 476-479; 32.
Glinski, RW, et al.; Refractory overactive bladder: Beyond oral anticholinergic therapy; Indian J Urol; 2007; 166-173; 23.
Gonzalez-Chamorro, F, et al.; [Current status of neurostimulation and neuromodulation for vesicourethral dysfunction]; Arch Esp Urol; 1997; 687-694; 50;Abstract.
Gonzalez-Chamorro, F, et al.; [Neurostimulation and neuromodulation in urinary incontinence]; Rev Med Univ Navarra; 2004; 75-84; 48;Abstract.
Gormley, EA, et al.; Diagnosis and treatment of overactive bladder (non-neurogenic) in adults: AUA/SUFU guideline amendment; J Urol; 2015; 1572-1580; 193.
Gottwald, T, et al.; [Sex differences in neuromodulation of mucosal mast cells in the rat jejunum]; Langenbecks Arch Chir; 1997; 157-163; 382;Abstract.
Govaert, B, et al.; Neuromodulation for functional bowel disorders; Best Pract Res Clin Gastroenterol; 2009; 545-553; 23.

(56) References Cited

OTHER PUBLICATIONS

Govier, FE, et al.; Percutaneous afferent neuromodulation for the refractory overactive bladder: results of a multicenter study; J Urol; 2001; 1193-1198; 165.
Green, BT, et al.; Neuromodulation of enteropathogen internalization in Peyer's patches from porcine jejunum; J Neuroimmunol; 2003; 74-82; 141.
Griffin, KM, et al.; Sacral nerve stimulation increases activation of the primary somatosensory cortex by anal canal stimulation in an experimental model; Br J Surg; 2011; 1160-1169; 98.
Grill, WM; Electrical activation of spinal neural circuits: application to motor-system neural prostheses; Neuromodulation; 2000; 97-106; 3.
Groen, J, et al.; Chronic pudendal nerve neuromodulation in women with idiopathic refractory detrusor overactivity incontinence: results of a pilot study with a novel minimally invasive implantable mini-stimulator; Neurourol Urodyn; 2005; 226-230; 24.
Groen, J, et al.; Computerized assessment of detrusor instability in patients treated with sacral neuromodulation; J Urol; 2001; 169-173; 165.
Groen, J, et al.; Neuromodulation techniques in the treatment of the overactive bladder; BJU Int; 2001; 723-731; 87.
Groen, J, et al.; Sacral neuromodulation in women with idiopathic detrusor overactivity incontinence: decreased overactivity but unchanged bladder contraction strength and urethral resistance during voiding; J Urol; 2006; 1005-1009; discussion 1009; 175.
Groen, LA, et al.; Sacral neuromodulation with an implantable pulse generator in children with lower urinary tract symptoms: 15-year experience; J Urol; 2012; 1313-1317; 188.
Groenendijk, PM, et al.; Five-Year Follow-up After Sacral Neuromodulation: Single Center Experience; Neuromodulation; 2007; 363-368; 10.
Groenendijk, PM, et al.; Urodynamic evaluation of sacral neuromodulation for urge urinary incontinence; BJU Int; 2008; 325-329; 101.
Gross, T, et al.; Transcutaneous Electrical Nerve Stimulation for Treating Neurogenic Lower Urinary Tract Dysfunction: A Systematic Review; Eur Urol; 2016;Abstract.
Grossi, U, et al.; Sacral neuromodulation for anorectal dysfunction secondary to congenital imperforate anus: report of two cases; Int J Colorectal Dis; 2014; 889-890; 29.
Grunewald, V; Neuromodulation/neurostimulation; World J Urol; 1998; 299-300; 16.
Guerci, B, et al.; Gastric electrical stimulation for the treatment of diabetic gastroparesis; Diabetes Metab; 2012; 393-402; 38.
Gulur, DM, et al.; Management of overactive bladder; Nat Rev Urol; 2010; 572-582; 7.
Gupta, P, et al.; Percutaneous tibial nerve stimulation and sacral neuromodulation: an update; Curr Urol Rep; 2015; 4; 16.
Guys, JM, et al.; [Neurogenic bladder in children: basic principles in diagnosis and treatment]; Ann Urol (Paris); 2006; 15-27; 40;Abstract.
Bernstein, AJ, et al.; Expanding indications for neuromodulation; Urol Clin North Am; 2005; 59-63; 32.
Bertapelle, MP, et al.; Sacral neuromodulation and Botulinum toxin A for refractory idiopathic overactive bladder: a cost-utility analysis in the perspective of Italian Healthcare System; World J Urol; 2015; 1109-1117; 33.
Beusterien, K, et al.; Use of best-worst scaling to assess patient perceptions of treatments for refractory overactive bladder; Neurourol Urodyn; 2015;Abstract.
Biemans, JM, et al.; Efficacy and effectiveness of percutaneous tibial nerve stimulation in the treatment of pelvic organ disorders: a systematic review; Neuromodulation; 2013; 25-33; discussion 33; 16.
Bleier, JI, et al.; Surgical management of fecal incontinence; Gastroenterol Clin North Am; 2013; 815-836; 42.
Blok, BF, et al.; Different brain effects during chronic and acute sacral neuromodulation in urge incontinent patients with implanted neurostimulators; BJU Int; 2006; 1238-1243; 98.

Bolton, JF, et al.; Neuromodulation 10 years on: how widely should we use this technique in bladder dysfunction?; Curr Opin Urol; 2009; 375-379; 19.
Bosch, JL, et al.; Neuromodulation: urodynamic effects of sacral (S3) spinal nerve stimulation in patients with detrusor instability or detrusor hyperflexia; Behav Brain Res; 1998; 141-150; 92.
Bosch, JL, et al.; Sacral nerve neuromodulation in the treatment of patients with refractory motor urge incontinence: long-term results of a prospective longitudinal study; J Urol; 2000; 1219-1222; 163.
Bosch, JL, et al.; What treatment should we use if drugs fail for OAB; and, what really works after drugs?; Neurourol Urodyn; 2010; 658-661; 29.
Bosch, JL; An update on sacral neuromodulation: where do we stand with this in the management of lower urinary tract dysfunction in 2010?; BJU Int; 2010; 1432-1442; 106.
Bosch, JL; Sacral neuromodulation in the treatment of the unstable bladder; Curr Opin Urol; 1998; 287-291; 8.
Bosch, JL; Sacral neuromodulation: treatment success is not just a matter of optimal electrode position; BJU Int; 2000; 20-21; discussion 22-23; 85 Suppl 3.
Bouchelouche, K, et al.; Recent developments in the management of interstitial cystitis; Curr Opin Urol; 2003; 309-313; 13.
Bouguen, G, et al.; Effects of transcutaneous tibial nerve stimulation on anorectal physiology in fecal incontinence: a double-blind placebo-controlled cross-over evaluation; Neurogastroenterol Motil; 2014; 247-254; 26.
Bower, WF, et al.; A pilot study of the home application of transcutaneous neuromodulation in children with urgency or urge incontinence; J Urol; 2001; 2420-2422; 166.
Bower, WF, et al.; A review of non-invasive electro neuromodulation as an intervention for non-neurogenic bladder dysfunction in children; Neurourol Urodyn; 2004; 63-67; 23.
Bower, WF, et al.; A urodynamic study of surface neuromodulation versus sham in detrusor instability and sensory urgency; J Urol; 1998; 2133-2136; 160.
Braun, PM, et al.; [Chronic sacral bilateral neuromodulation. Using a minimal invasive implantation technique in patients with disorders of bladder function]; Urologe A; 2002; 44-47; 41.
Braun, PM, et al.; Alterations of cortical electrical activity in patients with sacral neuromodulator; Eur Urol; 2002; 562-566; discussion 566-567; 41.
Braun, PM, et al.; Stimulation signal modification in a porcine model for suppression of unstable detrusor contractions; Urology; 2003; 839-844; 61.
Braun, PM, et al.; Tailored laminectomy: a new technique for neuromodulator implantation; J Urol; 1999; 1607-1609; 162.
Brink, TS, et al.; A Chronic, Conscious Large Animal Platform to Quantify Therapeutic Effects of Sacral Neuromodulation on Bladder Function; J Urol; 2015; 252-258; 194.
Bristow, SE, et al.; TENS: a treatment option for bladder dysfunction; Int Urogynecol J Pelvic Floor Dysfunct; 1996; 185-190; 7.
Brooks, DR, et al.; The Caenorhabditis elegans orthologue of mammalian puromycin-sensitive aminopeptidase has roles in embryogenesis and reproduction; J Biol Chem; 2003; 42795-42801; 278.
Brosa, M, et al.; Cost-effectiveness analysis of sacral neuromodulation (SNM) with Interstim for fecal incontinence patients in Spain; Curr Med Res Opin; 2008; 907-918; 24.
Bross, S, et al.; [Sacral neuromodulation in patients with nonobstructive, chronic urinary retention: relevance of the carbachol test and influence of associated nerve lession]; Aktuelle Urol; 2003; 157-161; 34;Abstract.
Bross, S, et al.; The role of the carbachol test and concomitant diseases in patients with nonobstructive urinary retention undergoing sacral neuromodulation; World J Urol; 2003; 346-349; 20.
Brouwer, R, et al.; Sacral nerve neuromodulation is effective treatment for fecal incontinence in the presence of a sphincter defect, pudendal neuropathy, or previous sphincter repair; Dis Colon Rectum; 2010; 273-278; 53.
Brown, DR, et al.; Delta-opioid receptor mRNA expression and immunohistochemical localization in porcine ileum; Dig Dis Sci; 1998; 1402-1410; 43.

(56) References Cited

OTHER PUBLICATIONS

Brown, ET, et al.; New evidence in the treatment of overactive bladder; Curr Opin Obstet Gynecol; 2015; 366-372; 27.
Brown, SR, et al.; Surgery for faecal incontinence in adults; Cochrane Database Syst Rev; 2013; Cd001757; 7.
Buback, D; The use of neuromodulation for treatment of urinary incontinence; Aorn j; 2001; 176-178, 181-177, 189-190; quiz 191-176; 73;Abstract.
Bugbee, M, et al.; An implant for chronic selective stimulation of nerves; Med Eng Phys; 2001; 29-36; 23.
Buhmann, H, et al.; [Update on fecal incontinence]; Praxis (Bern 1994); 2014; 1313-1321; 103.
Burks, FN, et al.; Neuromodulation and the neurogenic bladder; Urol Clin North Am; 2010; 559-565; 37.
Burks, FN, et al.; Neuromodulation versus medication for overactive bladder: the case for early intervention; Curr Urol Rep; 2009; 342-346; 10.
Burnstock, G, et al.; P2X receptors in health and disease; Adv Pharmacol; 2011; 333-372; 61;Abstract.
Burnstock, G; Innervation of bladder and bowel; Ciba Found Symp; 1990; 2-18; discussion 18-26; 151;Abstract.
Burnstock, G; Introduction and perspective, historical note; Front Cell Neurosci; 2013; 227; 7.
Burnstock, G; Introductory overview of purinergic signalling; Front Biosci (Elite Ed); 2011; 896-900; 3;Abstract.
Burnstock, G; Purinergic cotransmission; F1000 Biol Rep; 2009; 46; 1.
Burnstock, G; Purinergic signalling in the gastrointestinal tract and related organs in health and disease; Purinergic Signal; 2014; 18323; 10.
Burnstock, G; Purinergic signalling: Its unpopular beginning, its acceptance and its exciting future; Bioessays; 2012; 218-225; 34.
Burnstock, G; Purinergic signalling: past, present and future; Braz J Med Biol Res; 2009; 42437; 42.
Burnstock, G; The journey to establish purinergic signalling in the gut; Neurogastroenterol Motil; 2008; 42601; 20 Suppl 1.
Cadish, LA, et al.; Stimulation latency and comparison of cycling regimens in women using sacral neuromodulation; Neurourol Urodyn; 2016;Abstract.
Cameron, AP, et al.; Battery explantation after sacral neuromodulation in the Medicare population; Neurourol Urodyn; 2013; 238-241; 32.
Campbell, JD, et al.; Treatment success for overactive bladder with urinary urge incontinence refractory to oral antimuscarinics: a review of published evidence; BMC Urol; 2009; 18; 9.
Campin, L, et al.; [Urinary functional disorders bound to deep endometriosis and to its treatment: review of the literature]; J Gynecol Obstet Biol Reprod (Paris); 2014; 431-442; 43;Abstract.
Sherman, ND, et al.; Sacrel neuromodulation for the treatment of refractory urinary urge incontinence after stress incontinence surgery; Am J Obstet Gynecol, 2005; 2083-2087,193.
Sherman, ND, et al.; The current use of neuromodulation for bladder dysfuntion: Minerva Ginecol; 2000; 283-293; 58:Abstract.
Shi, P. et al.; Bladder response to acute sacral neuromodulation while treating rats in different phases of complete spinal cord injury: a preliminary study; Int Braz J Urol; 2015; 1194-1201; 41.
Shi, P, et al.: Effects of acute sacral neuromodulation on bladder reflex in complete spinal ori injury rats; Neuromodulation: 2013; 583-589; discussion 589; 16.
Shvarts, PG, et al.; [The modern methods of the electrical stimulation for the management of neurogenic disturbances of urination]; Vopr Kurortol Fizioter Lech Fiz Kult; 2015; 18-21; 92.
Siegel, S, et al.; Results of a prospective, randomized, multicenter study evaluating sacral neuromodulation with InterStim therapy compared to standard medial therapy at 6-months in subjects with mild syptoms of overactive bladder; Neurourol Urodyn: 2015; 224-230; 34.
Sievert, KD, et al.; [Unconventional treatment procedures of the bladder in paraplegia and myelomeningocele]; Urologe A; 2012; 1692-1696; 51.
Sievert, KD, et al.; Early sacral neuromodulation prevents urinary incontinence after complete spinal cord injury; Ann Neurol; 2010; 74-84; 67.
Sievert, KD; Neuromodulation; Neurourol Urodyn; 2005; 310; 24.
Signorello, D, et al.; Impact of sacral neuromodulation on female sexual function and his correlation with clinical outcome and quality of life indexes: a monocentric experience; J Sex Med; 2011; 1147-1155; 8.
Sillen, U, et al.; Effects of transcutaneous neuromodulation (TENS) on overactive bladder symptoms in children: a randomized controlled trial; J Pediatr Urol; 2014; 1100-1105; 10.
Silveri, M, et al.; Voiding dysfunction in x-linked adrenoleukodystrophy: symptom score and urodynamic findings; J Urol; 2004; 2651-2653; 171.
Sivalingam, N, et al.; Concepts in the management of the overactive bladder in women; Med J Malaysia; 2012; 137-141; quiz 142; 67.
Skobejko-Wlodarska, L; [Non-neurogenic lower urinary tract dysfuntion]; Pol Merkur Lekarski; 2008; 131-137; 24 Suppl 4;Abstract.
Smaldone, MC, et al.; Neuromodulation versus neurotoxin for the treatment of refractory detrusor overactivity: for neurotoxin: Nat Clin Pract Urol; 2008; 120-121; 5.
Smith, AL, et al.; Contemporary management of overactive bladder; Postgrad Med; 2012; 104-116; 124;Abstract.
Smits, MA, et al.; [Neuromodulation as a treatment for overactive bladder syndrome]; Ned Tijdschr Geneeskd; 2012; A4135; 156;Abstract.
Smits, MA, et al.; Sacral neuromodulation in patients with idiopathic overactive bladder after intial botulinum toxin therapy: J Urol; 2013; 2148-2158; 190.
Snellings, AE, et al.; Effects of stimulation site and stimulation parameters on bladder inhibition by electrical nerve stimulation; BJU Int; 2012; 136-143; 110.
South, MM, et al.; Detrusor overactivity does not predict outcome of sacral neuromodulation test stimulation; Int Urogynecol J Pelvic Floor Dysfunct: 2007; 1395-1398; 18.
Speer, LM, et al.; Chronic Pelvic Pain in Women; Am Fam Physician, 2016; 380-387; 93.
Spinelli, M, et al.; A new minimally invasive procedure for pudendal nerve stimulation to treat neurogenic bladder: description of the method and preliminary data; Neurourol Urodyn; 2005; 305-309; 24.
Spinelli, M, et al.; Latest technologic and surgical developments in using InterStim Therapy for sacral neuromodulation: impact on treatment success and safety; Eur Urol; 2008; 1287-1296; 54.
Spinelli, M, et al.; New sacral neuromodulation lead for percutaneous implantation using local anesthesia: description and first experience; J Urol; 2003; 1905-1907; 170.
Srivastava, D; Efficacy of sacral neuromodulation in treating chronic pain related to painful bladder syndrome/interstitial cystitis in adults; J Anaesthesiol Clin Pharmacol; 2012; 428-435; 28.
Starkman, JS, et al.; Management of refractory urinary urge incontienence following urogynecological surgery with sacral neuromodulation; Neurourol Urodyn; 2007; 29-35; discussion 36; 26.
Starkman, JS, et al.; Refractory overactive bladder after urethrolysis for bladder outlet obstruction: management with sacral neuromodulation; Int Urogynecol J Pelvic Floor Dysfunct; 2008; 277-282; 19.
Starkman, JS, et al.; Surgical options for drug-refractory overactive bladder patients; Rev Urol: 2010; e97-e110; 12.
Starkman, JS, et al.; The evolution of obstruction induced overactive bladder symptoms following urethrolysis for female bladder outlet obstruction; J Urol; 2008; 1018-1023; 179.
Steanu, ID, et al.; The Place of the Ice Water Test (IWT) in the Evaluation of the Patients with Traumatic Spinal Cord Injury, Maedica (Buchar); 2012; 125-130; 7.
Stephany, HA, et al.; Prospective evaluation of sacral nerve modulation in children with validated questionnaires; J Urol; 2013; 1516-1522; 190.
Stoffel, JT: Contemporary management of the neurogenic bladder for multiple sclerosis patients; Urol Clin North Am; 2010; 547-557; 37.
Su, X, et al.; Comparison of neural targets for neuromodulation of bladder micturition reflex in the rat; Am J Physiol Renal Physiol; 2012; F1196-1206; 303.

(56) References Cited

OTHER PUBLICATIONS

Su, X, et al.; Differentiation and interaction of tibial versus spinal nerve stimulation for micturition control in the rat; Neurourol Urodyn; 2015; 92-97; 34.
Su, X, et al.; Neuromodulation attenuates bladder hyperactivity in a rat cystitis model; BMC Urol; 2013; 70; 13.
Su, X, et al.; Neuromodulation in a rat model of the bladder micturition reflex; Am J Physiol Renal Physiol. 2012; F477-486; 302.
Su, X, et al.; Optimization of Neuromodulation for Bladder Control in a Rat Cystitis Model; Neuromodulation; 2016; 101-107; 19.
Su, X, et at.; Preclinical assessment of potential interactions between botulinum toxin and neuromodulation for bladder micturition reflex; BMC Urol; 2015; 50; 15.
Su, X, et al.; Quantification of effectiveness of bilateral and unilateral neuromodulation in the rat bladder rhythmic contraction model; BMC Urol; 2013; 34; 13.
Su, X, et al.; Role of the endogenous opioid systme in modulation of urinary bladder activity by spinal nerve stimulation; Am J Physiol Renal Physiol; 2013; F52-60; 305.
Sullivan, J. et al.; Overactive detrusor; Curr Opin Urol; 199; 291-296; 9.
Sullivan, J, et al.; The overactive bladder: neuropharmacological basis of clinical management; Curr Opin Obstet Gynecol; 1999; 477-483; 11.
Sun, Y, et al.; Effects of neural blocking agents on motor activity and secretion in the proximal and distal rat colon; evidence of marked segmental differences in nicotinic receptor activity; Scand J Gastroenterol; 2000; 380-388; 35.
Suskind, AM, et al.; Physician Use of Sacral Neuromodulation Among Medicare Beneficiaries With Overactive Bladder and Urinary Retention; Urology; 2015; 30-34; 86.
Suskind, AM, et al.; Understanding the dissemination of sacral neuromodulation; Surg Innov; 2013; 625-630; 20.
Sutherland, RS, et al.; Vesicourethral function in mice with genetic disruption of neuronal nitric oxide synthase; J Urol; 1997; 1109-1116; 157.
Svensson, L, et al.; Neuromodulation of experimental Shigella infection reduces damage to the gut mucosa; Microbes Infect; 2004; 256-264; 6.
Swinn, MJ, et al.; The cause and natural history of isolated urinary retention in young women; J Urol; 2002; 151-156; 167.
Tai, C, et al.; Bladder inhibition by intermittent pudendal nerve stimulation in cat using transdermal amplitude-modulated signal (TAMS); Neurourol Urodyn; 2012; 1181-1184; 31.
Tai, C, et al.; Inhibition of bladder overactivity by stimulation of feline pudendal nerve using transdermal amplitude-modulation signal (TAMS); BJU Int; 2012; 782-787; 109.
Canbaz Kabay, S, et al.; Long term sustained therapeutic effects of percutaneous posterior tibial nerve stimulation treatment of neurogenic overactive bladder in multiple sclerosis patients: 12-months results; Neurourol Urodyn; 2015; Abstract.
Cardarelli, S, et al.; Efficacy of sacral neuromodulation on urological diseases: a multicentric research project; Urologia; 2012; 90-96; 79.
Cardot, V, et al.; [Guidelines for the treatment of urinary incontinence in women with refractory idiopathic vesical hyperactivity using sacral neuromodulation]; Prog Urol; 2010; S161-169; 20 Suppl 2;Abstract.
Carey, HV, et al.; Neuromodulation of intestinal transport in the suckling mouse; Am J Physiol; 1989; R481-486; 256; Abstract.
Carey, M, et al.; Sacral nerve root stimulation for lower urinary tract dysfunction: overcoming the problem of lead migration; BJU Int; 2001; 15-18; 87.
Carlson, JJ, et al.; Estimating the cost-effectiveness of onabotulinumtoxinA for neurogenic detrusor overactivity in the United States; Clin Ther; 2013; 414-424; 35.
Carlucci, L, et al.; Functional variability of sacral roots in bladder control; J Neurosurg Spine; 2014; 961-965; 21.
Carr, MC; Conservative nonsurgical management of spina bifida; Curr Urol Rep; 2010; 109-113; 11.
Carrington, EV, et al.; A systematic review of sacral nerve stimulation mechanisms in the treatment of fecal Incontinence and constipation; Neurogastroenterol Motil; 2014; 1222-1237; 26.
Chaabane, W, et al.; Sacral neuromodulation for treating neurogenic bladder dysfunction: clinical and urodynamic study; Neurourol Urodyn; 2011; 547-550; 30.
Chan, DK, et al.; Effective treatment of dyssynergic defecation using sacral neuromodulation in a patient with cerebral palsy; Female Pelvic Med Reconstr Surg; 2015; e27-29; 21;Abstract.
Chancellor, MB, et al.; Principles of Sacral Nerve Stimulation (SNS) for the Treatment of Bladder and Urethral Sphincter Dysfunctions; Neuromodulation; 2000; 16-26; 3.
Chandra, A, et al.; Neuromodulation of perineally transposed antropylorus with pudendal nerve anastomosis following total anorectal reconstruction in humans; Neurogastroenterol Motil; 2014; 1342-1348; 26.
Chapple, C, et al.; The second-line management of idiopathic overactive bladder: what is the place of sacral neuromodulation and botulinum toxin-A in contemporary practice?; BJU Int; 2009; 1188-1190; 104.
Chapple, CR, et al.; Surgery for detrusor overactivity; World J Urol; 1998; 268-273; 16.
Chartier-Kastler, E, et al.; [Sacral neuromodulation with InterStim system: Results from the French national register]; Prog Urol; 2011; 209-217; 21;Abstract.
Chartier-Kastler, E, et al.; [Update on the second line management of idiopathic overactive bladder]; Prog Urol; 2009; 530-537; 19;Abstract.
Chartier-Kastler, E; Sacral neuromodulation for treating the symptoms of overactive bladder syndrome and non-obstructive urinary retention: >10 years of clinical experience; BJU Int; 2008; 417-423; 101.
Chatoor, D, et al.; Constipation and evacuation disorders; Best Pract Res Clin Gastroenterol; 2009; 517-530; 23.
Chen, G, et al.; Sacral neuromodulation for neurogenic bladder and bowel dysfunction with multiple symptoms secondary to spinal cord disease; Spinal Cord; 2014;Abstract.
Chen, G, et al.; The inhibitory effects of pudendal nerve stimulation on bladder overactivity in spinal cord injury dogs: is early stimulation necessary?; Neuromodulation; 2012; 232-237; discussion 237; 15.
Chen, ML, et al.; Electrical stimulation of somatic afferent nerves in the foot increases bladder capacity in healthy human subjects; J Urol; 2014; 1009-1013; 191.
Chen, SC, et al.; Pudendal neuromodulation improves voiding efficiency in diabetic rats; Neurourol Urodyn; 2013; 293-300; 32.
Chiarioni, G, et al.; Neuromodulation for fecal incontinence: an effective surgical intervention; World J Gastroenterol; 2013; 7048-7054; 19.
Choudhary, M, et al.; Inhibitory effects of tibial nerve stimulation on bladder neurophysiology in rats; Springerplus; 2016; 35; 5.
Colaco, M, et al.; Current guidelines in the management of interstitial cystitis; Transl Androl Urol; 2015; 677-683; 4.
Collins, SM; Is the irritable gut an inflamed gut?; Scand J Gastroenterol Suppl; 1992; 102-105; 192;Abstract.
Comiter, CV; Conscious Neuromodulation of the Bladder before Clinical Use; J Urol; 2015; 16-17; 194.
Comiter, CV; Sacral neuromodulation for the symptomatic treatment of refractory interstitial cystitis: a prospective study; J Urol; 2003; 1369-1373; 169.
Corcos, J, et al.; Canadian Urological Association guidelines on urinary incontinence; Can J Urol; 2006; 3127-3138; 13;Abstract.
Cornu, JN; Actual treatment of overactive bladder and urge urinary incontinence; Minerva Urol Nefrol; 2013; 21-35; 65;Abstract.
Costa, JA, et al.; Spinal cord neuromodulation for voiding dysfunction; Clin Obstet Gynecol; 2000; 676-688; 43.
Craggs, M, et al.; Neuromodulation of the lower urinary tract; Exp Physiol; 1999; 149-160; 84.
Craggs, MD; Objective measurement of bladder sensation: use of a new patient-activated device and response to neuromodulation; BJU Int; 2005; 29-36; 96 Suppl 1.

(56) References Cited

OTHER PUBLICATIONS

Crock, LW, et al.; Central amygdala metabotropic glutamate receptor 5 in the modulation of visceral pain; J Neurosci; 2012; 14217-14226; 32.
Dahms, SE, et al.; Sacral neurostimulation and neuromodulation in urological practice; Curr Opin Urol; 2000; 329-335; 10.
Daneshgari, F, et al.; Future directions in pelvic neuromodulation; Urol Clin North Am; 2005; 113-115, viii; 32.
Daneshgari, F; Applications of neuromodulation of the lower urinary tract in female urology; Int Braz J Urol; 2006; 262-272; 32.
Daniels, DH, et al.; Sacral neuromodulation in diabetic patients: success and complications in the treatment of voiding dysfunction; Neurourol Urodyn; 2010; 578-581; 29.
Dasgupta, R, et al.; Changes in brain activity following sacral neuromodulation for urinary retention; J Urol; 2005; 2268-2272; 174.
Dasgupta, R, et al.; The management of female voiding dysfunction: Fowler's syndrome—a contemporary update; Curr Opin Urol; 2003; 293-299; 13.
Davis, T, et al.; Sacral neuromodulation outcomes for the treatment of refractory idiopathic detrusor overactivity stratified by indication: Lack of anticholinergic efficacy versus intolerability; Can Urol Assoc J; 2013; 176-178; 7.
De Boer, TA, et al.; [Male urinary incontinence]; Ned Tijdschr Geneeskd; 2008; 797-802; 152;Abstract.
De Gennaro, M, et al.; Current state of nerve stimulation technique for lower urinary tract dysfunction in children; J Urol; 2011; 1571-1577; 185.
De Gennaro, M, et al.; Percutaneous tibial nerve neuromodulation is well tolerated in children and effective for treating refractory vesical dysfunction; J Urol; 2004; 1911-1913; 171.
De Groat, WC, et al.; Impact of Bioelectronic Medicine on the Neural Regulation of Pelvic Visceral Function; Bioelectron Med; 2015; 25-36; 2015.
De Seze, M, et al.; [Peripheral electrical stimulation in neurogenic bladder]; Ann Readapt Med Phys; 2008; 473-478; 51;Abstract.
Deffieux, X, et al.; [Voiding dysfunction after surgical resection of deeply infiltrating endometriosis: pathophysiology and management]; Gynecol Obstet Fertil; 2007; S8-13; 35 Suppl 1;Abstract.
Del Popolo, G, et al.; [Standard pharmacological treatment and new therapies for overactive bladder]; Urologia; 2012; 42534; 79.
Denzinger, S, et al.; Does sacral neuromodulation lead to relevant reduction in the need for intermittent catheterization? A single-center experience on patients with chronic urinary retention; Neuromodulation; 2012; 586-591; discussion 591; 15.
Guys. JM, et al.; Sacral neuromodutation for neurogenic bladder dysfunction in children; J Urol; 2004; 1673-1676; 172.
Haddad, M, et al.; Sacral neuromodulation in children with urinary and fecal incontinence: a multicenter, open label, randomized, crossover study, J Urol: 2010; 696-701; 184.
Hamann, MF, et al.; [Urinary incontinence in men and women. Diagnostics and conservative therapy]; Urolege A; 2014; 1073-1084; quiz 1085-1076: 53.
Hartmann, KE, at al.; Treatment of overactive bladder in women; Evid Rep Technol Assess (Full Rep): 2009; 1-120. v:.
Hasan, ST, et al.; Neuromodulation in bladder dysfunction; Curr Opin Obstet Gynecol; 1998: 395-399; 10.
Hasan, ST, et al.; Surface localization of sacral foramina for neuromodulation of bladder function, An anatomical study; Eur Urol: 1996; 90-98; 29;Abstract.
Hasan, ST, et al.; Transcutaneous electrical nerve stimulation and temporary S3 neuromodulation in idiopathic detrusor instability; J Urol; 1996; 2005-2011; 155.
Hashim, H, et al.; Drug treatment of overactive bladder: efficacy, cost and quality-of-life considerations; Drugs; 2004; 1643-1656; 64.
Hashim, H, et al.; Novel uses for antidiuresis; Int J Clin Prat Suppl; 2007; 32-36; ;Abstract.
Hashim. H, et al.; Patient preferences for treating refractory overactive bladder in the UK; Int Urol Nephrol; 2015; 1619-1627: 47.
Hassouna, M, et al,; Dog as an animal model for neurostimulation; Neurourol Urodyn; 1994; 159-167; 13.
Hassouna, M. et al.; Update on sacral neuromodulation; indications and outcomes; Curr Urol Rep; 2003; 391-398; 4.
Hassouna, M; Sacral neuromodulation for overactive bladder: Is it worth It?: Can Urol Assoc J; 2013: E454; 7.
Hassouna, MM, et al.; Economic evaluation of sacral neuromodutation in overactive bladder: A Canadian perspective; Can Urol Assoc J; 2015; 242-247; 9.
Hedlund, H. et al.; Sacral neuromodulation in Norway: clinical experience of the first three years; Scand J Urol Nephrol Suppl; 2002; 87-95; ;Abstract.
Heinze, K, et al.; [Neuromodulation—new techniques]; Urologe A; 2015; 373-377; 54.
Hellstrom, PA, et al.; Sacral nerve stimulation lead implantation using the O-arm; BMC Urol; 2013; 48: 13.
Herbison. GP, et al.; Sacral neuromodulation with implanted devices for urinary storage and voiding dysfunction in adults; Cochrane Database Syst Rev; 2009; Cd004202.
Hersh, L, et al.; Clinical management of urinary incontinence in women: Am Fam Physician; 2013; 634-640, 87.
Hijaz, A, et al.; Complications and troubleshooting of two-stage sacral neuromodulation therapy: a single-institution experience; Urology; 2006; 533-537; 68.
Hill, AJ, et al.; Resolution of Chronic Vulvar Pruritus With Replacement of a Neuromodulation Device; J Minim Invasive Gynecol; 2015: 889-891; 22.
Hindley, RG, et al.; The 2-year symptomatic and urodynamic results of a prospective randomized trial of interstitial radiofrequency therapy vs transurethral resection of the prostate; BJU Int; 2001; 217-220; 88.
Hoag, N, et al.; Underactive Bladder: Clinical Features, Urodynamic Parameters, and Treatment; Int Neurourol J; 2015; 185-189; 19.
Hoch, M, et al.; [Chemical destruction of sacral nerve roots by alcohol injection for the treatment of overactive bladder]; Prog Urol; 2006; 584-587; 16;Abstract.
Hoda, MR, et al.; [Sacral neuromodulation in urology. The emperor's new clothes or effective high-tech medicine?]; Urologe A; 2010; 1254-1259: 49.
Hoebeke, P. et al.; Transcutaneous neuromodulation for the urge syndrome in children: a pilot study; J Urol; 2001; 2416-2419; 166.
Hohenfellner, M, et el.; [Sacral neuromodulation of the urinary bladder]: Urologe A; 2000: 55-63; 39.
Hohenfellner, M, et al.; Bilateral chronic sacral neuromodutation for treatment of low urinary tract dysfunction; J Urol; 1998; 821-824; 160.
Hohenfellner, M, et al.; Chronic sacral neuromodulation for treatment of neurogenic bladder dysfunction: long-term results with unilateral implants; Urology; 2001; 887-892: 58.
Hohenfellner, M. et al.; Sacral neuromodulation for treatment of lower urinary tract dysfunction: BJU Int: 2000; 10-19; discussion 22-13, 85 Suppl 3.
Hoque, T, et al.; Validation of internal controls for gene expression analysis in the intestine of rats infected with Hymenolepis diminuta; Parasitol Int; 2007; 325-329; 56.
Horrocks, EJ, et al.; Double-blind randomised controlled trial of percutaneous tibial nerve stimulation versus sham electrical stimulation in the treatment of faecal incontinence: CONtrol of Faecal Incontinence using Distal NeuromodulaTion (the CONFIDeNT trial); Health Technol Assess; 2015; 1-164; 19.
Hotouras, A. et al.; Prospective clinical audit of two neuromodulatory treatments for fecal incontinence: sacral nerve stimulation (SNS) and percutaneous tibial nerve stimulation (PTNS); Surg Today: 2014: 2124-2130; 44.
Hoyle, CH, et al.; Ethylcholine mustard aziridinium on (AF64A) impairs cholinergic neuromuscular transmission in the guinea-pig ileum and urinary bladder, and cholinergic neuromodulation in the enteric nervous system of the guinea-pig distal colon; Gen Pharmacol; 1986; 543-548; 17.
Hubsher, CP, et al.; Sacral nerve stimulation for neuromodulation of the lower urinary tract; Can J Urol; 2012; 6480-6484; 19.

(56) References Cited

OTHER PUBLICATIONS

Hull, T, et al., Long-term durability of sacral nerve stimulation therapy for chronic fecal incontinence; Dis Colon Rectum; 2013; 234-245; 56.
Hull, TL; Sacral neuromodulation stimulation in fecal incontinence; Int Urogynecol J; 2010: 1565-1568; 21.
Humphreys, MR, et al.; Preliminary results of sacral neuromodulation in 23 children: J Urol; 2006; 2227-2231; 176.
Hyun, SJ, et al.; Comparative analysis between thoracic spinal cord and sacral neuromodulation in a rat spinal cord injury model; a preliminary report of a rat spinal cord stimulation model; Korean J Spine; 2013; 14-18; 10.
Iarumov, N, et al.; [Anal incontinence—new methods of surgical treatment using artificial bowel sphincter and sacral nerve stimulation]; Khirurgiia (Sofiia): 2007; 40-45; ;Abstract.
Indar, A, et al.; A dual benefit of sacral neuromodulation; Surg Innov; 2008; 219-222: 15.
Indinnimeo, M. et al.; Sacral neuromodulation for the treatment of fecal incontinence: analysis of cost-effectiveness; Dis Colon Rectum; 2010; 1661-1669, 53.
Ingber, MS, et al.; Neuromodulation and female sexual function: does treatment for refractory voiding symptoms have an added benefit?; Int Urogynecol J Pelvic Floor Dysfunct; 2009; 1055-1059: 20.
Iqbal, F, et al.; Bilateral transcutaneous tibial nerve stimulation for chronic constipation; Colorectal Dis; 2016; 173-178; 18.
Ishigooka, M, et al.; Sacral nerve stimulation and diurnal urine volume; Eur Urol; 1999; 421-426; 36;Abstract.
Jacobs, SA, et al.; Randomized prospective crossover study of interstim lead wire placement with curved versus straight stylet; Neurourol Urodyn; 2014; 488-492; 33.
Jadav, AM, et al.; Does sacral nerve stimulation improve global pelvic function in women?; Colorectal Dis; 2013; 848-857; 15.
Jarrett, ME; Neuromodulation for constipation and fecal incontinence; Urol Clin North Am; 2005; 79-87; 32.
Jarvis; JC, et al.; Functional electrical stimulation for control of internal organ function; Neuromodulation; 2001; 155-164; 4.
Jesus, LE, et al.; Psychosocial and respiratory disease related to severe bladder dysfunction and non-monosymptomatic enuresis; J Pediatr Urol; 2015;Abstract.
Majerus, SJ, et al.; Wireless, Ultra-Low-Power Implantable Sensor for Chronic Bladder Pressure Monitoring: ACM J Emerg Technol Comput Syst; 2012;8.
Mally, AD, et al.; Role of opioid and metabotropic glutamate 5 receptors in pudendal inhibition of bladder overactivity in cats; J Urol; 2013; 1574-1579; 189.
Malossi, J, et al.; Sacral neuromodulation for the treatment of bladder dysfunction; Curr Urol Rep; 2002; 61-66; 3.
Malouf, AJ, et al.; Short-term effets of sacral nerve stimulation for idiopathic slow transit constipation; World J Surg; 2002; 166-170; 26.
Mamopoulos, A, et al., Active sacral neuromodulator during pregnancy: a unique case report; Am J Obstet Gynecol: 2014; e4-5; 211.
Manriquez, V. et al.; Transcutaneous posterior tibial nerve stimulation versus extended release oxybutynin in overactive bladder patients. A prospective randomized trial; Eur J Obstet Gynecol Reprod Biol; 2016; 42531; 196.
Marcelissen, T, et al.; Is the screening method of sacral neuromodulation a prognostic factor for long-term success?; J Urol; 2011; 583-587; 185.
Marcelissen, T, et al.; Sacral neuromodulation as a treatment for chornic pelvic pain; J Urol; 2011; 387-393; 186.
Marcelissen, TA, et al.; Long-term results of sacral neuromodulation with the tined lead procedure; J Urol; 2010; 1997-2000; 184.
Marcelissen, TA, et al.; Psychological and psychiatric factors as predictors for success in sacral neuromodulation treatment; BJU Int; 2011; 1834-1838; 108.
Marcelissen, TA, et al.; The effect of pulse rate changes on the clinical outcome of sacral neuromodulation; J Urol; 2011; 1781-1785; 185.
Marcelissen, TA, et al.; The use of bilaterai sacral nerve stimulation in patients with loss of unilateral treatment efficacy; J Urol; 2011; 976-980; 185.
Marinkovic, SP, et al.; Neuromodutation for Overactive Bladder Symptoms in Women Utilizing Either Motor or Sensory/Motor Provocation With a Minimum Nine-Year Follow-Up; Neuromodulation; 2015; 517-521; discussion 521; 18.
Martin Braun, P, et al.; [Continuous bilateral sacral neuromodulation as a minimally invasive implantation technique to patients with functional bladder changes]; Arch Esp Urol; 2003; 497-501; 56.
Martinson, M. et al.; Cost of neuromodulation therapies for overactive bladder: percutaneous tibial nerve stimulation versus sacral nerve stimulation; J Urol; 2013; 210-216; 189.
Mason, MD, et al.; Prospective Evaluation of Sacral Neuromodulation in Children: Outcomes and Urodynamic Predictors of Success; J Urol; 2016.
Matsuta Y, et al.; Contribution of opioid and metabotropic glutamate receptor mechanisms to inhibition of bladder overactivity by tibial nerve stimulation; Am J Physiol Regul Integr Comp Physiol; 2013; R126-133; 305.
Matsuta, Y, et al.; Effect of methysergide on pudendal inhibition of micturition reflex in cats; Exp Neurol; 2013; 250-258; 247.
Matsuta, Y, et al.; Poststimulation inhibition of the mictuntion reflex induced by tibial nerve stimulation in rats; Physiol Rep; 2014; e00205; 2.
Mauroy, B, et al.; [Long-term results of interferential current stimulation in the treatment of bladder instability]; Prog Urol; 2001; 34-39; 11; Abstract.
Mayer, R; Neuromodulation—who, what, when, where and why?; J Urol; 2010; 17-18; 183.
Mayr, CA, et al.; Cost-effectiveness of novel therapies for overactive bladder; Expert Rev Pharmacoecon Outcomes Res; 2014; 527-535; 14.
Mazo, EB, et al.; [Temporary sacral and tibial neuromodulation in treating patients with ovractive urinary bladder]; Zh Vopr Neirokhir Im N N.Burdenko; 2002; 17-21; ;Abstract.
Mazo, EB, et al.; [Temporary sacral neuromodulation in patients with urge incontinence]; Urologiia: 2000; 42-46; ;Abstract.
Mazo, EB, et al.; [The role of somatosensory evoked potentials in prognosis of efficacy of tibial neuromodulation in patients with hyperactive urinary bladder]; Urologiia; 2005; 49-52; ;Abstract.
McAchran, SE, et al.; Sacral neuromodulation in the older woman; Clin Obstet Gynecol; 2007; 735-744; 50.
McKertich, K; Urinary incontinence-procedural and surgical treatments for women; Aust Fam Physician, 2008; 122-131; 37.
McNevin, MS, et al.; Outcomes associated with interstim therapy for medically refractory fecal incontinence; Am J Surg; 2014; 735-737; discussion 737-788; 207.
Mehnert, U, et al.; [Neuro-urological dysfunction of the lower urinary tract in CNS diseases: pathophysiology, epidemiology, and treatment options]; Urologe A; 2012; 189-197; 51.
Mehnert, U, et al.; The management of urinary incontinence in the male neurological patient; Curr Opin Urol; 2014; 586-592; 24.
Meissnitzer, T, et al.; CT-Guided Lead Placement for Selective Sacral Neuromodulation to Treat Lower Urinary Tract Dysfunctions; AJR Am J Rosentgenol; 2015; 1139-1142; 205.
Melenhorst, J, et al.; Sacral neuromodulation in patients with faecal incontinence: results of the first 100 permanent implantation; Colorectal Dis; 2007; 725-730; 9.
Meurette, G. et al.; Sacral nerve stimulation enhances epithelial barrier of the rectum: results from a porcine model; Neurogastroenterol Motil; 2012; 267-273, e110; 24.
Michelsen, HB, et al.; Rectal volume tolerability and anal pressures in patients with fecal incontinence treated with sacral nerve stimulation; Dis Colon Rectum; 2006; 1039-1044; 49.
Miller, JJ, et al.; Diagnosis and treatment of overactive bladder; Minerva Ginecol; 2005; 501-520; 57;Abstract.
Milne, JL; Behavioral therapies for overactive bladder: making sense of the evidence: J Wound Ostomy Continence Nurs; 2008; 93-101; quiz 102-103; 35;Abstract.
Minardi, D, et al.; Activity and expression of nitric oxide synthase in rat bladder after saral neuromodulation; Int J Immunopathol Pharmacol; 2008; 129-135; 21;Abstract.

(56) References Cited

OTHER PUBLICATIONS

Minardi, D, et al.; Lower urinary tract and bowel disorders and multiple sclerosis: role of sacral neuromodulation: a preliminary report; Neuromodulation; 2005; 176-181; 8.
Miotla, P, et al.; [Sacral nerve stimulation in the treatment of the lower urinary tract function disorders]; Ginekol Pol; 2011; 851-856; 82.
Mishra, NN; Clinical presentation and treatment of bladder pain syndrome/interstitial cystitis (BPS/IC) in India; Transl Androl Urol; 2015; 512-523; 4.
Moon, KH, et al.; Prospective Trial of Sacral Neuromodulation for Refractory Overactive Bladder Syndrome in Korean Patients; Low Urin Tract Symptoms; 2014; 175-179; 6.
Moutzouris, DA, et al.; Interstitial cystitis: an unsolved enigma: Clin J Am Soc Nephrol; 2009; 1844-1857; 4.
Murphy, AM, et al.; Treatment of overactive bladder: what is on the horizon?; Int Urogynecol J; 2013; 42503; 24.
Musco, S, et al.; Percutaneous Tibial Nerve Stimulation Improves Female Sexual Function in Women with Overactive Bladdere Syndrome: J Sex Med; 2016.
N. Patidar et al.; Transcutaneous posterior tibial nerve stimulation in pediatric overactivebladdeer; A preliminary report; Journal of Pediatric Urology; 2015; 351.e1-351.e6; 11.
Nakib, N, et al.; Neuromodulation versus neurotoxin for the treatment of refractory detrusor overactivity: for neuromodulation; Nat Clin Pract Urol; 2008; 118-119; 5.
Nambiar, A, et al.; Chapter 4: Guidelines for the diagnosis and treatment of overactive bladder (OAB) and neurogenic detrusor overactivity (NDO); Neurourol Urodyn; 2014; S21-25; 33 Suppl 3.
Natalin, R, et al.; Management of OAB in those over age 65; Curr Urol Rep; 2013; 379-385; 14,
Ng, CK, et al.; Refractory overactive bladder in men: update on novel therapies; Curr Urol Rep; 2006; 456-461; 7.
Nijman, RJ; Classification and treatment of functional incontinence in children; BJU Int; 2000; 37-42; discussion 45-36; 85 Suppl 3.
Krivoborodov, GG, et al.; [Tibial neuromodulation in the treatment of neurogenic detrusor hyperactivity in patients with Parkinson's disease]; Urologiia; 2006; 42435; ;Abstract.
Krolczyk, G, et al.; Effects of continuous microchip (MC) vagal neuromodulation on gastrointestinal function in rats; J Physiol Pharmacol; 2001; 705-715; 52.
Kubota, M, et al.; Effects of neuromodulation with sacral magnetic stimulation for intractable bowel or bladder dysfunction in postoperative patients with anorectal malformation: a preliminary report; Pediatr Surg Int; 2011; 599-603; 27.
Kumsar, S, et al.; Effects of sacral neuromodulation on isolated urinary bladder function in a rat model of spinal cord injury; Neuromodulation; 2015; 67-74; discussion 74-65; 18.
Kuo, HC; Recovery of detrusor function after urethral botulinum A toxin injection in patients with idiopathic low detrusor contractility and voiding dysfunction: Urology; 2007; 57-61; discussion 61-52; 69.
Kuo, TL, et al.; Pelvic floor spasm as a cause of voiding dysfunction; Curr Opin Urol; 2015; 311-316; 25.
Kurpad, R, et al.; The evaluation and management of refractory neurogenic overactive bladder: Curr Urol Rep; 2014; 444; 15.
Kutzenberger, J: [Neurogenic urinary incontinence. Value of surgical management]; Urologe A; 2008; 699-706; 47.
La, TH, et al.; Intermittent sacral neuromodulation for idiopathic urgency urinary incontinence in women; Neurourol Urodyn; 2015;Abstract.
Laudano, MA, et al.; Disparities in the Use of Sacral Neuromodulation among Medicare Beneficiaries; J Urol; 2015; 449-453; 194.
Laviana, A, et al.; Sacral neuromodulation for refractory overactive bladder, interstitial cystitis, and painful bladder syndrome; Neurosurg Clin N Am; 2014; 33-46; 25.
Lay, AH, et al.; The role of neuromodulation in patients with neurogenic overactive bladder; Curr Urol Rep; 2012; 343-347; 13.
Lazzeri, M, et al.; The challenge of overactive bladder therapy; alternative to antimuscarinic agents; Int Braz J Urol; 2006; 620-630; 32.
Le, NB, et al.; Expanding the Role of Neuromodulation for Overactive Bladder: New Indications and Alternatives to Delivery; Curr Bladder Dysfunct Rep; 2011; 25-30; 6.
Leclers, F, et al.; [Cystomanometric study of bladder sensation during sacral neuromodulation test]; Prog Urol; 2005; 238-243; 15;Abstract.
Lee, YY; What's New in the Toolbox for Constipation and Fecal Incontinence?; Front Med (Lausanne); 2014; 5; 1.
Leicht, W, et al.; [Botulinum toxin versus sacral neuromodulation for idiopathic detrusor overactivity]; Urologe A; 2012; 348-351; 51.
Leng, WW, et al.; How sacral nerve stimulation neuromodulation works; Urol Clin North Am; 2005; 42692; 32.
Leong, FC, et al.; Neuromodulation for the treatment of urinary incontinence; Mo Med; 2007; 435-439; 104;Abstract.
Leong, RK, et al.; Cost-effectiveness analysis of sacral neuromodulation and botulinum toxin A treatment for patients with idiopathic overactive bladder; BJU Int; 2011; 558-564; 108.
Leong, RK, et al.; Current information on sacral neuromodulation and botulinum toxin treatment for refractory idiopathic overactive bladder syndrome: a review; Urol Int; 2010; 245-253; 84.
Leong, RK, et al.; PNE versus 1st stage tined lead procedure: a direct comparison to select the most sensitive test method to identify patients suitable for sacral neuromodulation therapy; Neurourol Urodyn; 2011; 1249-1252; 30.
Leong, RK, et al.; Satisfaction and patient experience with sacral neuromodulation: results of a single center sample survey; J Urol; 2011; 588-592; 185.
Levin, PJ, et al.; Psychosocial factors related to the use of InterStim(R) for the treatment of refractory overactive bladder; Female Pelvic Med Reconstr Surg; 2014; 272-275; 20;Abstract.
Levin, PJ, et al.; The efficacy of posterior tibial nerve stimulation for the treatment of overactive bladder in women: a systematic review; Int Urogynecol J; 2012; 1591-1597; 23.
Levy, RM; The evolving definitioin of neuromodulation; Neuromodulation; 2014; 207-210; 17.
Lewis, JM, et al.; Non-traditional management of the neurogenic bladder; tissue engineering and neuromodulation; ScientificWorldJournal; 2007; 1230-1241; 7.
Liao, KK, et al.; Effect of sacral neuromodulation on the spinal nociceptive reflex of patients with idiopathic overactive bladder; Neuromodulation; 2008; 50-55; 11.
Liberman, D, et al.; Concerns regarding sacral neuromodulation as a treatment option for medical-refractory overactive bladder; Can Urol Assoc J; 2011; 285-287; 5.
Lin, YT, et al.; Effects of pudendal neuromodulation on bladder function in chronic spinal cord-injured rats; J Formos Med Assoc; 2015.
Linares Quevedo, AI, et al.; [Posterior sacral root neuromodulation in the treatment of chronic urinary dysfunction]; Actas Urol Esp; 2002; 250-260; 26;Abstract.
Lippmann, QK, et al.; Successful use of sacral neuromodulation in a 12-year-old with cerebral palsy and neurogenic bladder; Neuromodulation; 2014; 396-398; 17.
Lombardi, G. et al.; Clinical concomitant benefits on pelvic floor dysfunctions after sacral neuromodulation in patients with incomplete spinal cord injury; Spinal Cord; 2011; 629-636; 49.
Lombardi, G, et al.; Clinical female sexual outcome after sacral neuromodulation implant for lower urinary tract symptom (LUTS); J Sex Med; 2008; 1411-1417; 5.
Lombardi, G, et al.; Clinical outcome of sacral neuromodulation in incomplete spinal cord injured patients suffering from neurogenic lower urinary tract symptoms; Spinal Cord; 2009; 486-491; 47.
Lombardi, G, et al.; Clinical outcome of sacral neuromodulation in incomplete spinal cord-injured patients suffering from neurogenic bowel dysfunctions; Spinal Cord; 2010; 154-159; 48.
Lombardi, G, et al.; Intravesical electrostimulation versus sacral neuromodulation for incomplete spinal cord patients suffering from neurogenic non-obstructive urinary retention; Spinal Cord; 2013; 571-578; 51.

(56) References Cited

OTHER PUBLICATIONS

Lombardi, G, et al.; Sacral neuromodulation and female sexuality; Int Urogynecol J; 2015; 1751-1757; 26.
Lombardi, G, et al.; Sacral neuromodulation for lower urinary tract dysfunction and impact on erectile function; J Sex Med; 2008; 2135-2140; 5.
Lombardi, G, et al.; Sacral neuromodulation for neurogenic non-obstructive urinary retention in incomplete spinal cord patients: a ten-year-follow-up single-centre experience; Spinal Cord; 2014; 241-245; 52.
Lopez-Delgado, A, et al.; Effect on anal pressure of percutaneous posterior tibial nerve stimulation for faecal incontinence; Colorectal Dis; 2014; 533-537; 16.
Lowette, K, et al.; Role of corticosterone in the murine enteric nervous system during fasting: Am J Physiol Gastrointest Liver Physiol; 2014; G905-913; 307.
Lyon, TD, et al.; Pudendal but not tibial nerve stimulation inhibits bladder contractions induced by stimulation of pontine micturition center in cats; Am J Physiol Regul Integr Comp Physiol; 2016; R366-374; 310.
M. Matsushita et al.; Primary somatosensory evoked magnetic fields elicited by sacralsurface electrical stimulation; Neuroscience Letters; 2008; 77?80; 431.
Madersbacher, H, et al.; What are the causes and consequences of bladder overdistension? ICI-RS 2011; Neurourol Urodyn; 2012; 317-321; 31.
Madersbacher, H; Overactive bladder—a practical approach to evaluation and management; J Med Liban; 2004; 220-226; 52;Abstract.
Maeda, Y, et al.; Sacral nerve stimulation for faecal incontinence and constipation: a European consensus statement; Colorectal Dis; 2015; O74-87; 17.
Maher, CF, et al.; Percutaneous sacral nerve root neuromodulation for intractable interstitial cystitis; J Urol; 2001; 884-886; 165.
Maher, RM, et al.; A novel externally applied neuromuscular stimulator for the treatment of stress urinary incontinence in women—a pilot study; Neuromodulation; 2013; 590-594; discussion 594; 16.
Majerus, SJ, et al.; Low-power wireless micromanometer system for acute and chronic bladder-pressure monitoring; IEEE Trans Biomed Eng; 2011; 763-767; 58.
Abdel Raheem, A, et al.; Voiding dysfunction in women: How to manage it correctly; Arab J Urol; 2013; 319-330; 11.
Abraham, N, et al.; Urgency after a sling: review of the management; Curr Urol Rep; 2014; 400; 15.
Abrams, P, et al.; The role of neuromodulation in the management of urinary urge incontinence; BJU Int; 2003; 355-359; 91.
Abrams, P; The role of neuromodulation in the management of urinary urge incontinence; BJU Int; 2004; 1116; 93.
Allahdin, S, et al.; An overview of treatment of overactive bladder syndrome in women; J Obstet Gynaecol; 2012; 217-221; 32.
Alo, KM, et al.; Sacral nerve root stimulation for the treatment of urge incontinence and detrusor dysfunction utilizing a cephalocaudal intraspinal method of lead insertion: a case report; Neuromodulation; 2001; 53-58; 4.
Alo, KM, et al.; Selective Nerve Root Stimulation (SNRS) for the Treatment of Intractable Pelvic Pain and Motor Dysfunction: A Case Report; Neuromodulation; 2001; 19-23; 4.
Al-Shaiji, TF, et al.; Pelvic electrical neuromodulation for the treatment of overactive bladder symptoms; Adv Urol; 2011; 757454; 2011.
Al-Zahrani, AA, et al.; Long-term outcome and surgical interventions after sacral neuromodulation implant for lower urinary tract symptoms: 14-year experience at 1 center; J Urol; 2011; 981-986; 185.
Amarenco, G, et al.; Urodynamic effect of acute transcutaneous posterior tibial nerve stimulation in overactive bladder; J Urol; 2003; 2210-2215; 169.
Amend, B, et al.; [Second-line therapy of idiopathic detrusor overactivity. Sacral neuromodulation and botulinum toxin A]; Urologe A; 2010; 245-252; 49.
Amend, B, et al.; Prolonged percutaneous SNM testing does not cause infection-related explanation; BJU Int; 2013; 185-491; 111.
Amoroso, L, et al.; Sacral-neuromodulation CT-guided; Radiol Med; 2005; 421-429; 109;Abstract.
Amundsen, CL, et al.; Sacral neuromodulation for intractable urge incontinence: are there factors associated with cure?; Urology; 2005; 746-750; 66.
Amundsen, CL, et al.; Sacral neuromodulation in an older, urge-incontinent population; Am J Obstet Gynecol; 2002; 1462-1465; discussion 1465; 187.
Amundsen, Cl, et al.; The Refractory Overactive Bladder: Sacral NEuromodulation vs. BoTulinum Toxin Assessment: ROSETTA trial; Contemp Clin Trials; 2014; 272-283; 37.
Anger, JT, et al.; The effect of sacral neuromodulation on anticholinergic use and expenditures in a privately insured population; Neuromodulation; 2014; 72-74; discussion 74; 17.
Antolak, SJ, Jr., et al.; Therapeutic pudendal nerve blocks using corticosteroids cure pelvic pain after failure of sacral neuromodulation; Pain Med; 2009; 186-189; 10.
Antolak, SJ, Jr.; Re: Sacral neuromodulation for the symptomatic treatment of refractory interstitial cystitis: a prospective study; J Urol; 2003; 1956; author reply 1956; 170.
Anton, PA; Stress and mind-body impact on the course of inflammatory bowel diseases; Semin Gastrointest Dis; 1999; 14-19; 10;Abstract.
Aoun, F, et al.; [Lower urinary tract dysfunction following radical hysterectomy]; Prog Urol; 2015; 1184-1190; 25; Abstract.
Apostolidis, A; Neuromodulation for intractable OAB; Neurourol Urodyn; 2011; 766-770; 30.
Arlandis, S, et al.; Cost-effectiveness of sacral neuromodulation compared to botulinum neurotoxin a or continued medical management in refractory overactive bladder; Value Health; 2011; 219-228; 14.
Arnold, J, et al.; Overactive bladder syndrome—management and treatment options; Aust Fam Physician; 2012; 878-883; 41.
Arrabal-Polo, MA, et al.; Clinical efficacy in the treatment of overactive bladder refractory to anticholinergics by posterior tibial nerve stimulation; Korean J Urol; 2012; 483-486; 53.
Atiemo, HO, et al.; Evaluation and management of refractory overactive bladder; Curr Urol Rep; 2006; 370-375; 7.
Atnip, S, et al.; A unique approach to severe constipation; Urol Nurs; 2011; 348-350; 31.
Badawi, JK, et al.; [Current diagnostics and therapy of the overactive bladder and urge incontinence]; Dtsch Med Wochenschr; 2005; 1503-1506; 130;Abstract.
Badlani, GH; Update on lower urinary tract symptoms; ScientificWorldJournal; 2009; 499-500; 9.
Baeten, CG; Status of sacral neuromodulation for refractory constipation; Colorectal Dis; 2011; 19-22; 13 Suppl 2.
Balchandra, P, et al.; Women's perspective: intra-detrusor botox versus sacral neuromodulation for overactive plodder symptoms after unsuccessful anticholinergic treatment; Int Urogynecol J; 2014; 1059-1064; 25.
Banakhar, M, et al.; Effect of sacral neuromodulation on female sexual function and quality of life: Are they correlated?; Can Urol Assoc J; 2014; E762-767; 8.
Banakhar, M, et al.; Sacral Neuromodulation for Genitourinary Problems; Prog Neurol Surg; 2015; 192-199; 29; Abstract.
Banakhar, MA, et al.; Sacral neuromodulation and refractory overactive bladder: an emerging tool for an old problem; Ther Adv Urol; 2012; 179-185; 4.
Bannowsky, A, et al.; [Sacral neuromodulation in treatment of functional disorders of the lower urinary tract. An overview of basic principles, indications, outcomes]; Urologe A; 2003; 1357-1365; 42.
Bannowsky, A, et al.; Urodynamic changes and response rates in patients treated with permanent electrodes compared to conventional wire electrodes in the peripheral nerve evaluation test; World J Urol; 2008; 623-626; 26.
Banyo, T; [The role of electrical neuromodulation in the therapy of chronic lower urinary tract dysfunction]; Ideggyogy Sz; 2003; 68-71; 56;Abstract.

(56) References Cited

OTHER PUBLICATIONS

Barnett, G, et al.; Re: Cost of neuromodulation therapies for overactive bladder: percutaneous tibial nerve stimulation versus sacral nerve stimulation: M. Martinson, S. MacDiarmid and E. Black J Urol 2013; 189: 210-216; J Urol; 2013; 1444-1445; 190.
Baron, M, et al.; [Does urinary sacral neuromodulation improve bowel symptoms other than fecal incontinence: A systematic review]; Prog Urol; 2016;Abstract.
Barroso U Jr et al.; Electrical nerve stimulation for overactive bladder in children;Nature Reviews Urology; 2011; 402-407; 8.
Barroso, U, Jr., et al.; Posterior tibial nerve stimulation vs parasacral transcutaneous neuromodulation for overactive bladder in children; J Urol; 2013; 673-677; 190.
Bartley, J, et al.; Neuromodulation for overactive bladder; Nat Rev Urol; 2013; 513-521; 10.
Bartley, JM, et al.; Understanding clinic options for overactive bladder; Curr Urol Rep; 2013; 541-548; 14.
Batla, A, et al.; Lower urinary tract dysfunction in patients with functional movement disorders; J Neurol Sci; 2016; 192-194; 361.
Bayrak, O, et al.; Botulinum toxin injections for treating neurogenic detrusor overactivity; Turk J Urol; 2015; 221-227; 11.
Bemelmans, BL, et al.; Neuromodulation by implant for treating lower urinary tract symptoms and dysfunction; Eur Urol; 1999; 81-91; 36;Abstract.
Beneton, C, et al.; [The medical treatment of overactive bladder]; Neurochirurgie; 2003; 369-376; 49;Abstract.
Benson, JT, et al.; Pudendal neuralgia, a severe pain syndrome; Am J Obstet Gynecol; 2005; 1663-1668; 192.
Benson, JT; New therapeutic options for urge incontinence; Curr Womens Health Rep; 2001; 61-66; 1;Abstract.
Benson-Cooper, S, et al.; Introduction of sacral neuromodulation for the treatment of faecal incontinence; N Z Med J; 2013; 47-53; 126.

Action Potential in a Neuron

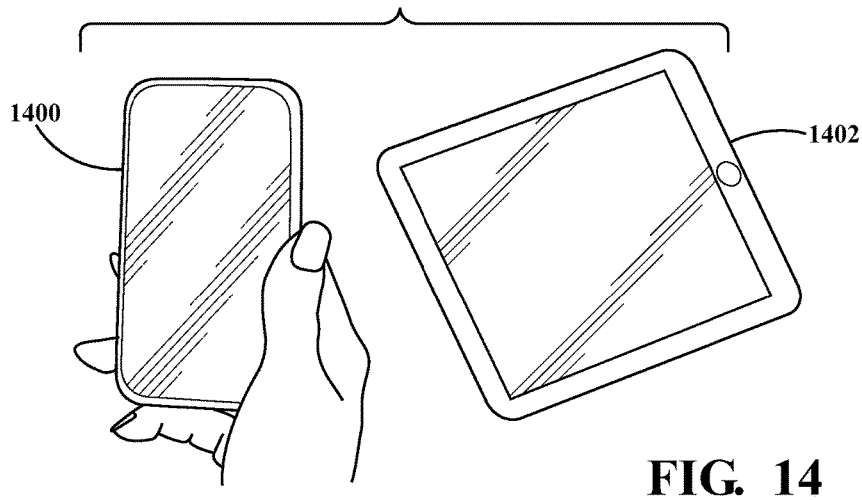
FIG. 14
FIG. 15
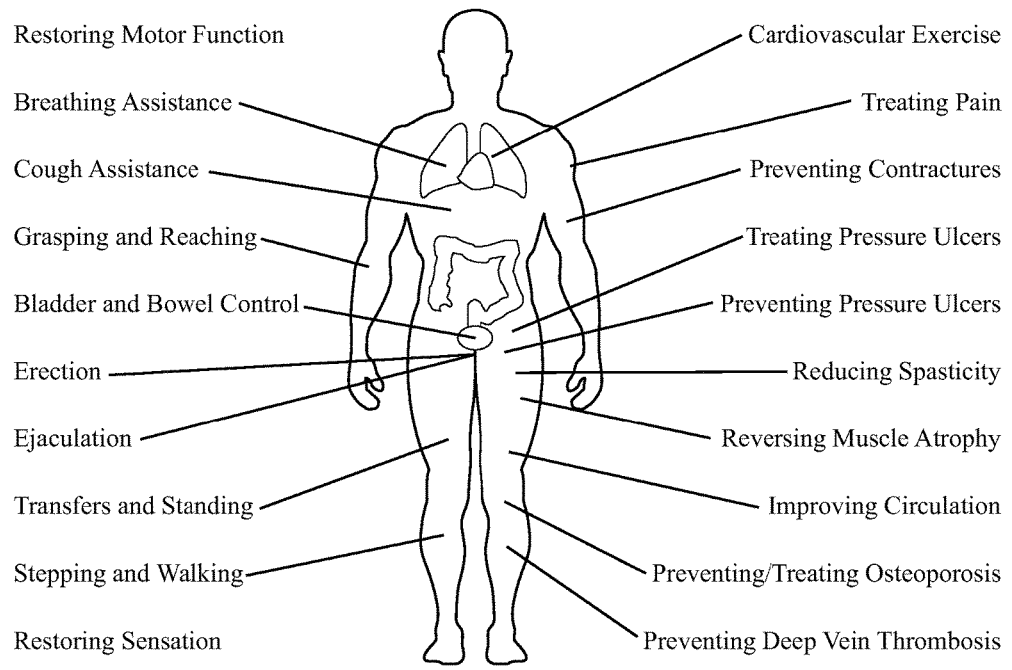

TOPICAL NEUROLOGICAL STIMULATION

CLAIM OF PRIORITY

This application claims priority to and the benefit of the filing date of PCT application PCT/US2014/040240 filed on May 30, 2014, and U.S. provisional patent application U.S. Ser. No. 61/828,981 filed on May 30, 2013, and incorporates that application in its entirety herein.

COPYRIGHT NOTICE

© 2013 and 2014 GRAHAM CREASEY, MD, & HOO-MIN TOONG, PhD. This patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d), (e).

TECHNICAL FIELD

This invention pertains to the activation of nerves by topical stimulators to control or influence muscles, tissues, organs, or sensation, including pain, in humans and mammals.

BACKGROUND

Nerve disorders may result in loss of control of muscle and other body functions, loss of sensation, or pain. Surgical procedures and medications sometimes treat these disorders but have limitations. This invention pertains to a system for offering other options for treatment and improvement of function.

BRIEF DESCRIPTION OF THE DRAWINGS

FIG. 14 are exemplary software platforms for communicating between the Control Units and the TNSS, gathering data, networking with other TNSSs, and external communications.

FIG. 15 represents TNSS applications for patients with spinal cord injury.

DETAILED DESCRIPTION

Figure 1:
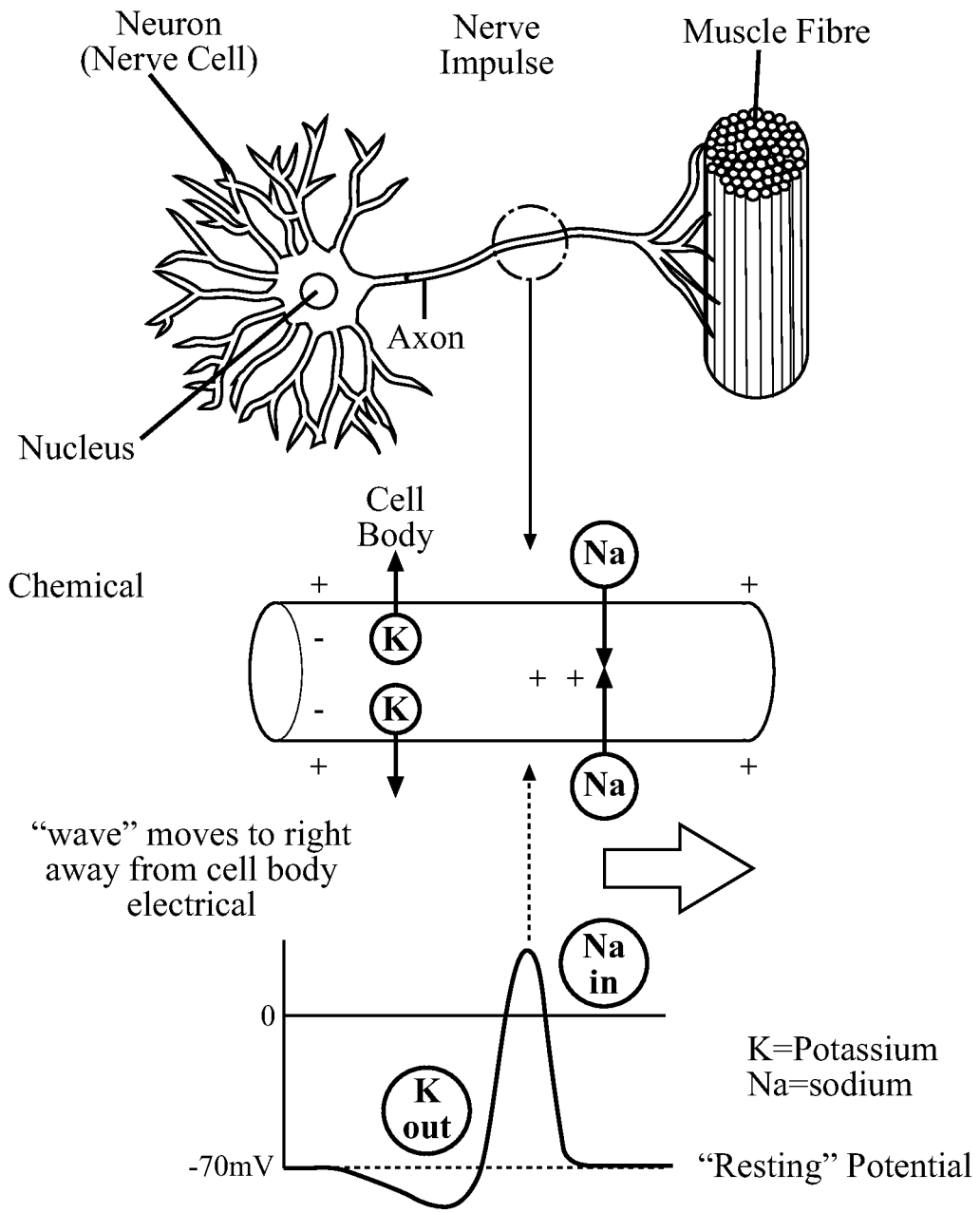
FIG. 1 is a depiction of a neuron activating a muscle by electrical impulse.

A method for electrical, mechanical, chemical and/or optical interaction with a human or mammal nervous system to stimulate and/or record body functions using small electronic devices attached to the skin and capable of being wirelessly linked to and controlled by a cellphone, activator or computer network.

The body is controlled by a chemical system and a nervous system. Nerves and muscles produce and respond to electrical voltages and currents. Electrical stimulation of these tissues can restore movement or feeling when these have been lost, or can modify the behavior of the nervous system, a process known as neuro modulation. Recording of the electrical activity of nerves and muscles is widely used for diagnosis, as in the electrocardiogram, electromyogram, electroencephalogram, etc. Electrical stimulation and recording require electrical interfaces for input and output of information. Electrical interfaces between tissues and electronic systems are usually one of three types:

a. Devices implanted surgically into the body, such as pacemakers. These are being developed for a variety of functions, such as restoring movement to paralyzed muscles or restoring hearing, and can potentially be applied to any nerve or muscle. These are typically specialized and somewhat expensive devices.

b. Devices inserted temporarily into the tissues, such as needles or catheters, connected to other equipment outside the body. Health care practitioners use these devices for diagnosis or short-term treatment.

c. Devices that record voltage from the surface of the skin for diagnosis and data collection, or apply electrical stimuli to the surface of the skin using adhesive patches connected to a stimulator. Portable battery-powered stimulators have typically been simple devices operated by a patient, for example for pain relief. Their use has been limited by;

i. The inconvenience of chronically managing wires, patches and stimulator, particularly if there are interfaces to more than one site, and ii. The difficulty for patients to control a variety of stimulus parameters such as amplitude, frequency, pulse width, duty cycle, etc.

Nerves can also be stimulated mechanically to produce sensation or provoke or alter reflexes; this is the basis of touch sensation and tactile feedback. Nerves can also be affected chemically by medications delivered locally or systemically and sometimes targeted to particular nerves on the basis of location or chemical type. Nerves can also be stimulated or inhibited optically if they have had genes inserted to make them light sensitive like some of the nerves in the eye. The actions of nerves also produce electrical, mechanical and chemical changes that can be sensed.

The topical nerve stimulator/sensor (TNSS) is a device to stimulate nerves and sense the actions of the body that can be placed on the skin of a human or mammal to act on and respond to a nerve, muscle or tissue. One implementation of the TNSS is the Smart Band Aid™ (SBA). A system, incorporating a SBA, controls neuro modulation and neuro stimulation activities. It consists of one or more controllers or Control Units, one or more TNSS modules, software that resides in Control Units and TNSS modules, wireless communication between these components, and a data managing platform. The controller hosts software that will control the functions of the TNSS. The controller takes inputs from the TNSS of data or image data for analysis by said software, The controller provides a physical user interface for display to and recording from the user, such as activating or disabling the TNSS, logging of data and usage statistics, generating reporting data. Finally, the controller provides communications with other Controllers or the Internet cloud.

The controller communicates with the neurostim module, also called TNSS module or SBA, and also communicates with the user. In at least one example, both of these communications can go in both directions, so each set of communications is a control loop. Optionally, there may also be a control loop directly between the TNSS module and the body. So the system optionally may be a hierarchical control system with at least four control loops. One loop is between the TNSS and the body; another loop is between the TNSS and the controller; another loop is between the controller and the user; and another loop is between the controller and other users via the cloud, which may be located in the TNSS, the controller or the cloud, has several functions including: (1) sending activation or disablement signals between the controller and the TNSS via a local network such as Bluetooth; (2) driving the user interface, as when the controller receives commands from the user and provides visual, auditory or tactile feedback to the user; (3) analyzing TNSS data, as well as other feedback data such as from the user, within the TNSS, and/or the controller and/or the cloud; (4) making decisions about the appropriate treatment; (5) system diagnostics for operational correctness; and (6) communications with other controllers or users via the Internet cloud for data transmission or exchange, or to interact with apps residing in the Internet cloud.

The control loop is closed. This is as a result of having both stimulating and sensing. The sensing provides information about the effects of stimulation, allowing the stimulation to be adjusted to a desired level or improved automatically.

Typically, stimulation will be applied. Sensing will be used to measure the effects of stimulation. The measurements sensed will be used to specify the next stimulation. This process can be repeated indefinitely with various durations of each part. For example: rapid cycling through the process (a-b-c-a-b-c-a-b-c); prolonged stimulation, occasional sensing (aaaa-b-c-aaaa-b-c-aaaa-b-c); or prolonged sensing, occasional stimulation (a-bbbb-c-a-bbbb-c-a-bbbb). The process may also start with sensing, and when an event in the body is detected this information is used to specify stimulation to treat or correct the event, for example, (bbbbbbbbb-c-a-bbbbbbbb-c-a-bbbbbbbbb). Other patterns are possible and contemplated within the scope of the application.

The same components can be used for stimulating and sensing alternately, by switching their connection between the stimulating circuits and the sensing circuits. The switching can be done by standard electronic components. In the case of electrical stimulating and sensing, the same electrodes can be used for both. An electronic switch is used to connect stimulating circuits to the electrodes and electric stimulation is applied to the tissues. Then the electronic switch disconnects the stimulating circuits from the electrodes and connects the sensing circuits to the electrodes and electrical signals from the tissues are recorded.

In the case of acoustic stimulating and sensing, the same ultrasonic transducers can be used for both (as in ultrasound imaging or radar). An electronic switch is used to connect circuits to the transducers to send acoustic signals (sound waves) into the tissues. Then the electronic switch disconnects these circuits from the transducers and connects other circuits to the transducers (to listen for reflected sound waves) and these acoustic signals from the tissues are recorded.

Other modalities of stimulation and sensing may be used (e.g. light, magnetic fields, etc) The closed loop control may be implemented autonomously by an individual TNSS or by multiple TNSS modules operating in a system such as that shown below in FIG. 16. Sensing might be carried out by some TNSSs and stimulation by others.

Stimulators are protocol controlled initiators of electrical stimulation, where such protocol may reside in either the TNSS and/or the controller and/or the cloud. Stimulators interact with associated sensors or activators, such as electrodes or MEMS devices.

The protocol, which may be located in the TNSS, the controller or the cloud, has several functions including:

(1) Sending activation or disablement signals between the controller and the TNSS via a local network such as Bluetooth. The protocol sends a signal by Bluetooth radio waves from the smartphone to the TNSS module on the skin, telling it to start or stop stimulating or sensing. Other wireless communication types are possible.

(2) Driving the user interface, as when the controller receives commands from the user and provides visual, auditory or tactile feedback to the user. The protocol receives a command from the user when the user touches an icon on the smartphone screen, and provides feedback to the user by displaying information on the smartphone screen, or causing the smartphone to beep or buzz.

(3) Analyzing TNSS data, as well as other feedback data such as from the user, within the TNSS, and/or the controller and/or or the cloud. The protocol analyzes data sensed by the TNSS, such as the position of a muscle, and data from the user such as the user's desires as expressed when the user touches an icon on the smartphone; this analysis can be done in the TNSS, in the smartphone, and/or in the cloud.

(4) Making decisions about the appropriate treatment. The protocol uses the data it analyzes to decide what stimulation to apply.

(5) System diagnostics for operational correctness. The protocol checks that the TNSS system is operating correctly.

(6) Communications with other controllers or users via the Internet cloud for data transmission or exchange, or to interact with apps residing in the Internet cloud. The protocol communicates with other smartphones or people via the internet wirelessly; this may include sending data over the internet, or using computer programs that are operating elsewhere on the internet.

A neurological control system, method and apparatus are configured in an ecosystem or modular platform that uses potentially disposable topical devices to provide interfaces between electronic computing systems and neural systems. These interfaces may be direct electrical connections via electrodes or may be indirect via transducers (sensors and actuators). It may have the following elements in various configurations: electrodes for sensing or activating electrical events in the body; actuators of various modalities; sensors of various modalities; wireless networking; and protocol applications, e.g. for data processing, recording, control systems. These components are integrated within the disposable topical device. This integration allows the topical device to function autonomously. It also allows the topical device along with a remote control unit (communicating wirelessly via an antenna, transmitter and receiver) to function autonomously.

Referring to FIG. 1, nerve cells are normally electrically polarized with the interior of the nerve being at an electric potential 70 mV negative relative to the exterior of the cell. Application of a suitable electric voltage to a nerve cell (raising the resting potential of the cell from −70 mV to above the firing threshold of −55 mV) can initiate a sequence of events in which this polarization is temporarily reversed in one region of the cell membrane and the change in polarization spreads along the length of the cell to influence other cells at a distance, e.g. to communicate with other nerve cells or to cause or prevent muscle contraction.

Figure 2:
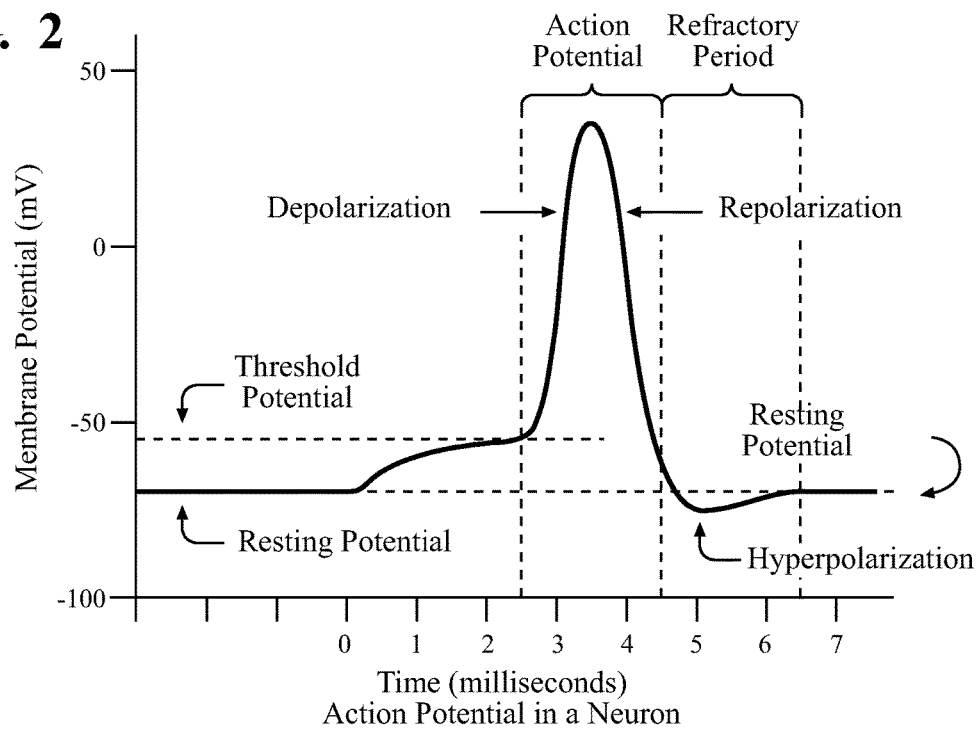
FIG. 2 is a representation of the electrical potential activation time of an electrical impulse in a nerve.

Referring to FIG. 2, graphically represents a nerve impulse from a point of stimulation resulting in a wave of depolarization followed by a repolarization that travels along the membrane of a neuron during the measured period. This spreading action potential is a nerve impulse. It is this phenomenon that allows for external electrical nerve stimulation.

Figure 3:
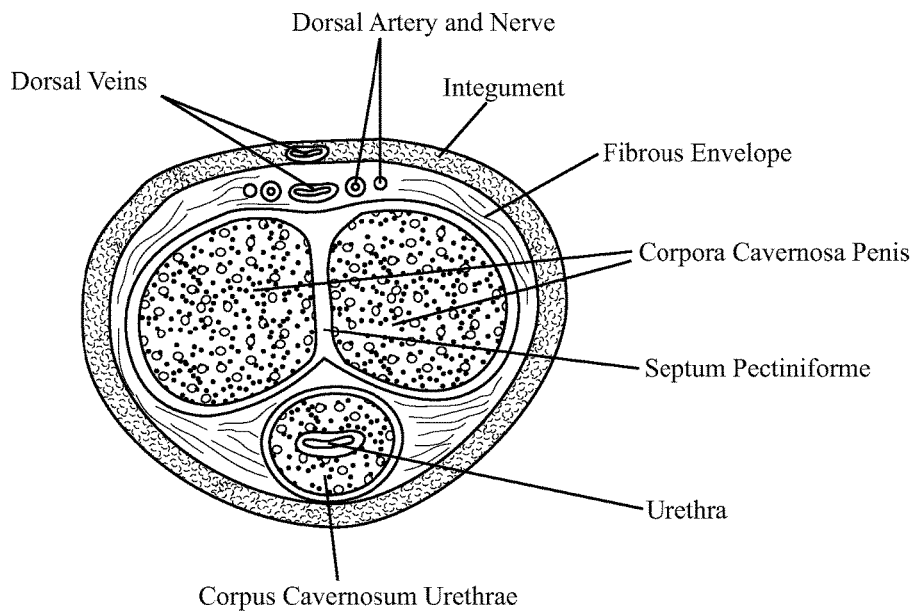
FIG. 3 is a cross section of a penis.

Referring to FIG. 3, the dorsal genital nerve on the back of the penis or clitoris just under the skin is a purely sensory nerve that is involved in normal inhibition of the activity of the bladder during sexual activity, and electrical stimulation of this nerve has been shown to reduce the symptoms of the Over Active Bladder. Stimulation of the underside of the penis may cause sexual arousal, erection, ejaculation and orgasm.

A Topical nerve stimulator/sensor (TNSS) is used to stimulate these nerves and is convenient, unobtrusive, self-powered, controlled from a smartphone or other control device. This has the advantage of being non-invasive, controlled by consumers themselves, and potentially distributed over the counter without a prescription.

Figure 4:
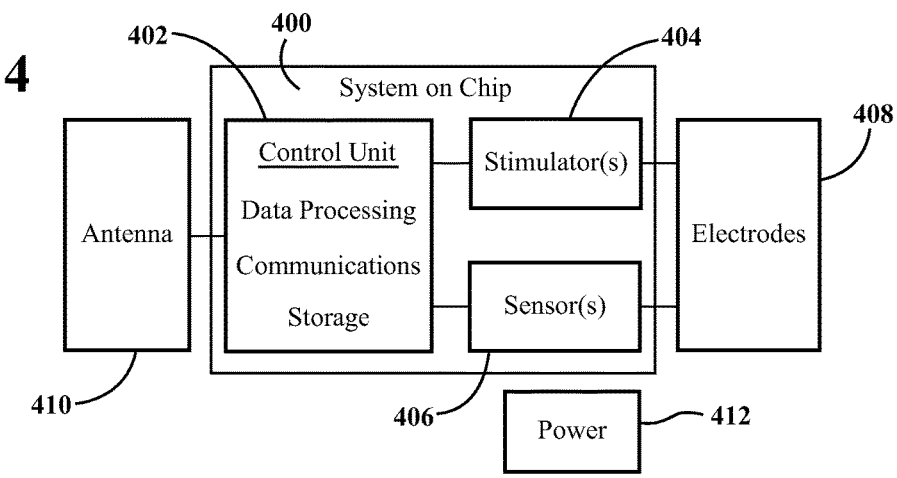
FIG. 4 is an illustration of a Topical Nerve Stimulator/Sensor (TNSS) component configuration including a system on a chip (SOC).

Referring to FIG. 4, the TNSS has one or more electronic circuits or chips that perform the functions of: communications with the controller, nerve stimulation via one or more electrodes 408 that produce a wide range of electric field(s) according to treatment regimen, one or more antennae 410 that may also serve as electrodes and communication pathways, and a wide range of sensors 406 such as, but not limited to, mechanical motion and pressure, temperature, humidity, chemical and positioning sensors. One arrangement would be to integrate a wide variety of these functions into an SOC, system on chip 400. Within this is shown a control unit 402 for data processing, communications and storage and one or more stimulators 404 and sensors 406 that are connected to electrodes 408. An antenna 410 is incorporated for external communications by the control unit. Also present is an internal power supply 412, which may be, for example, a battery. An external power supply is another variation of the chip configuration. It may be necessary to include more than one chip to accommodate a wide range of voltages for data processing and stimulation. Electronic circuits and chips will communicate with each other via conductive tracks within the device capable of transferring data and/or power.

In one or more examples, a Smart Band Aid™ incorporating a battery and electronic circuit and electrodes in the form of adhesive conductive pads may be applied to the skin, and electrical stimuli is passed from the adhesive pads into the tissues. Stimuli may typically be trains of voltage-regulated square waves at frequencies between 15 and 50 Hz with currents between 20 and 100 mA. The trains of stimuli are controlled from a smartphone operated by the user. Stimuli may be either initiated by the user when desired, or programmed according to a timed schedule, or initiated in response to an event detected by a sensor on the Smart Band Aid™ or elsewhere. Another implementation for males may be a TNSS incorporated in a ring that locates a stimulator conductively to selected nerves in a penis to be stimulated.

Figure 5:
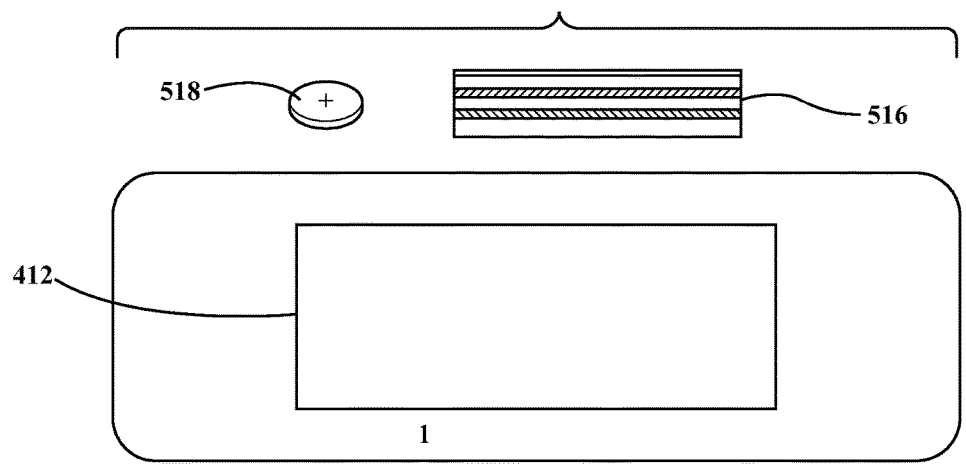
FIG. 5 is an illustration of the upper side of a Smart Band Aid™ (SBA) implementation of a TNSS showing location of battery, which may be of various types.

Referring to FIG. 5, limited lifetime battery sources will be employed as internal power supply 412, to power the TNSS deployed in this illustration as a Smart Band Aid™. These may take the form of Lithium Ion technology or traditional non-toxic MnO2 technologies. FIG. 5 illustrates different battery options such as a printable Manganese Oxide battery 516 and a button battery 518. A TNSS of different shapes may require different battery packaging.

Figure 6:
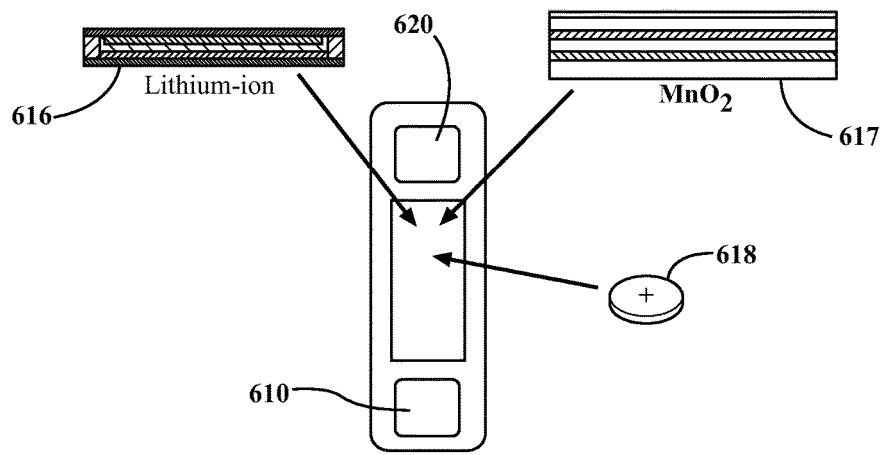
FIG. 6 is a an illustration of the lower side of the SBA of FIG. 5.

FIG. 6 shows an alternate arrangement of these components where the batteries 616-618 are positioned on the bottom side of the SBA between the electrodes 610 and 620. In this example, battery 616 is a lithium ion battery, battery 617 is a MnO2 battery and battery 618 is a button battery. Other types of batteries and other battery configurations are possible within the scope of this application in other examples.

Aside from the Controller, the Smart Band Aid™ Packaging Platform consists of an assembly of an adhesive patch capable of being applied to the skin and containing the TNSS Electronics, protocol, and power described above.

Figure 7:
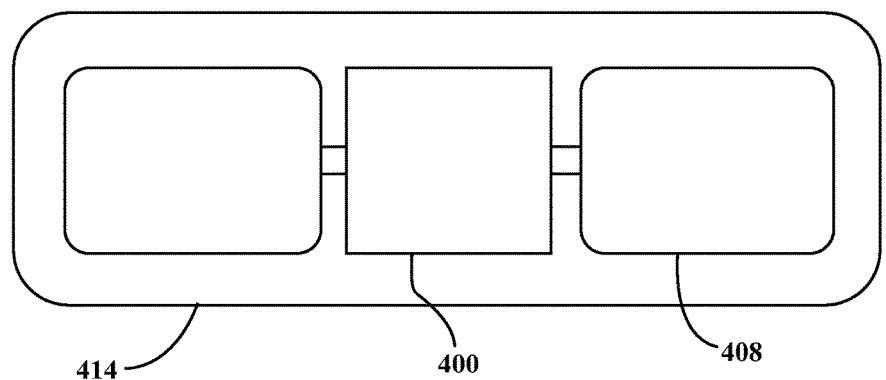
FIG. 7 is TNSS components incorporated into a SBA.

Referring to FIG. 7 is a TNSS deployed as a Smart Band Aid™ 414. The Smart Band Aid™ has a substrate with adhesive on a side for adherence to skin, the SOC 400 previously described in FIG. 4, or electronic package, and one or more electrodes 408 disposed between the dermis and the adhesive surface. The electrodes provide electrical stimuli through the dermis to nerves and other tissue and in turn may collect electrical signals from the body, such as the electrical signals produced by muscles when they contract (the electromyogram) to provide data about body functions such as muscle actions.

Figure 8:
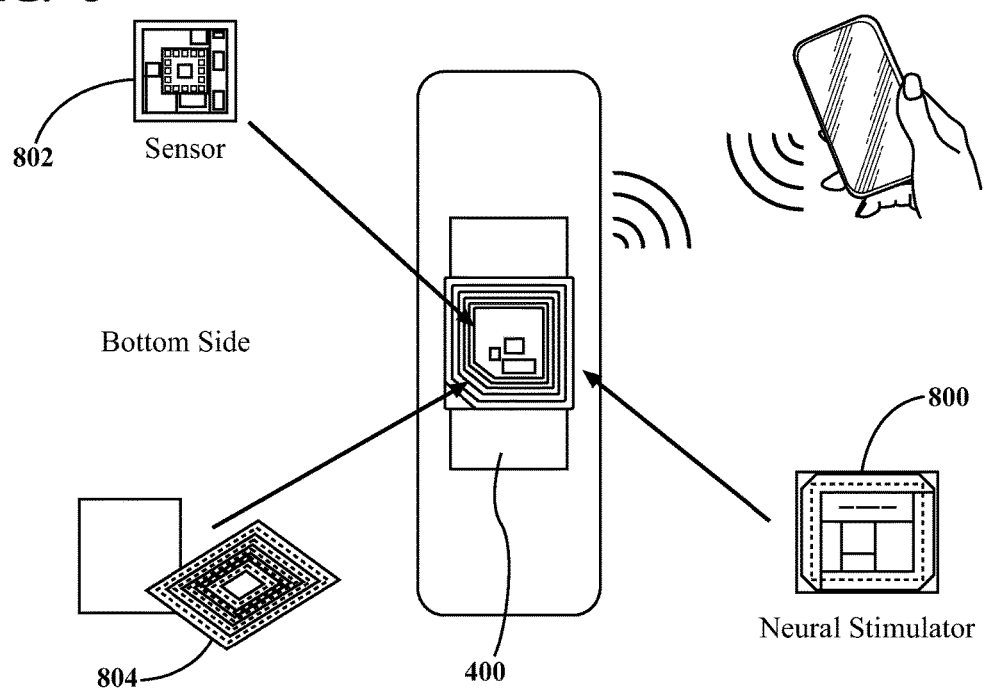
FIG. 8 is examples of optional neural stimulator and sensor chip sets incorporated into a SBA.

Referring to FIG. 8, different chips may be employed to design requirements. Shown are sample chips for packaging in a TNSS in this instance deployed as a SBA. For example, neural stimulator 800, sensor 802, processor/communications 804 are represented. The chips can be packaged separately on a substrate, including a flexible material, or as a system-on-chip (SOC) 400. The chip connections and electronics package are not shown but are known in the art.

Figure 9:
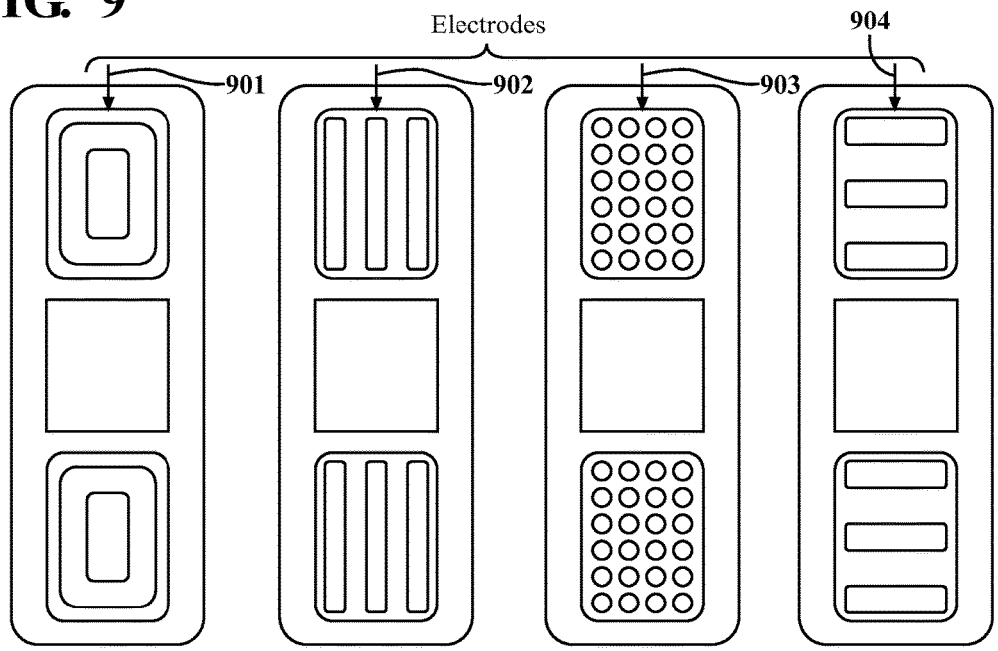
FIG. 9 is examples of optional electrode configurations for a SBA.

Referring to FIG. 9 SBAs with variations on arrangements of electrodes are shown. Each electrode may consist of a plurality of conductive contacts that give the electrode abilities to adjust the depth, directionality, and spatial distribution of the applied electric field. For all the example electrode configurations shown, 901-904, the depth of the electrical stimulation can be controlled by the voltage and power applied to the electrode contacts. Electric current can be applied to various electrode contacts at opposite end of the SBA, or within a plurality of electrode contacts on a single end of the SBA. The phase relationship of the signals applied to the electrode contacts can vary the directionality of the electric field. For all configurations of electrodes, the applied signals can vary over time and spatial dimensions. The configuration on the left, 901, shows a plurality of concentric electrode contacts at either end of the SBA. This configuration can be used to apply an electric stimulating field at various tissue depths by varying the power introduced to the electrode contacts. The next configuration, 902, shows electrodes 404 that are arranged in a plurality of parallel strips of electrical contacts. This allows the electric field to be oriented perpendicular or parallel to the SBA. The next configuration, 903, shows an example matrix of electrode contacts where the applied signal can generate a stimulating field between any two or more electrode contacts at either end of the SBA, or between two or more electrode contacts within a single matrix at one end of the SBA. Finally, the next configuration on the far right, 904, also shows electrodes that are arranged in a plurality of parallel strips of electrical contacts. As with the second configuration, this allows the electric field to be oriented perpendicular or parallel to the SBA. There may be many other arrangements of electrodes and contacts.

One or more TNSSs with one or more Controllers form a System. Systems can communicate and interact with each other and with distributed virtualized processing and storage services. This enables the gathering, exchange, and analysis of data among populations of systems for medical and non-medical applications.

Figure 10:
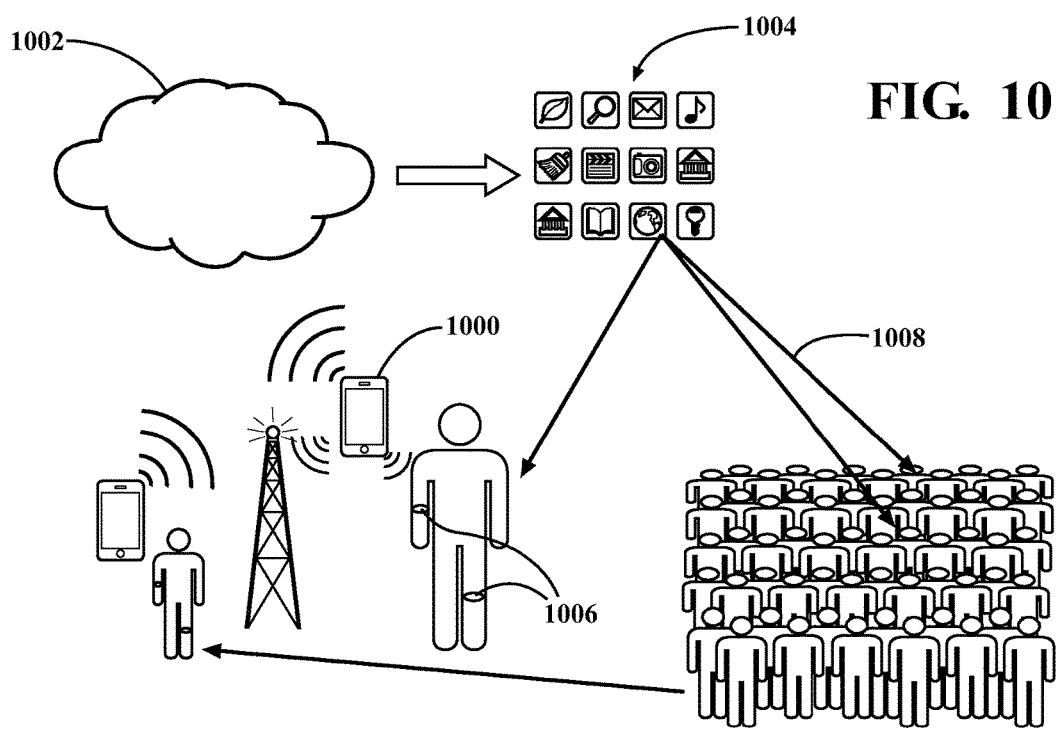
FIG. 10 is an example of the use of TNSS with a Control Unit as a System, in a population of Systems and software applications.

Referring to FIG. 10, a system is shown with two TNSS units 1006, with one on the wrist, one on the leg, communicating with its controller, a smartphone 1000 or other control device. The TNSS units can be both sensing and stimulating and can act independently and also work together in a Body Area Network (BAN). Systems communicate with each other over a communication bridge or network such as a cellular network. Systems also communicate with applications running in a distributed virtualized processing and storage environment generally via the Internet 1002. The purpose for communications with the distributed virtualized processing and storage environment is to communicate large amounts of user data for analysis and networking with other third parties such as hospitals, doctors, insurance companies, researchers, and others. There are applications that gather, exchange, and analyze data from multiple Systems 1004. Third party application developers can access TNSS systems and their data to deliver a wide range of applications. These applications can return data or control signals to the individual wearing the TNSS unit 1006. These applications can also send data or control signals to other members of the population who employ systems 1008. This may represent an individual's data, aggregated data from a population of users, data analyses, or supplementary data from other sources.

Figure 11:
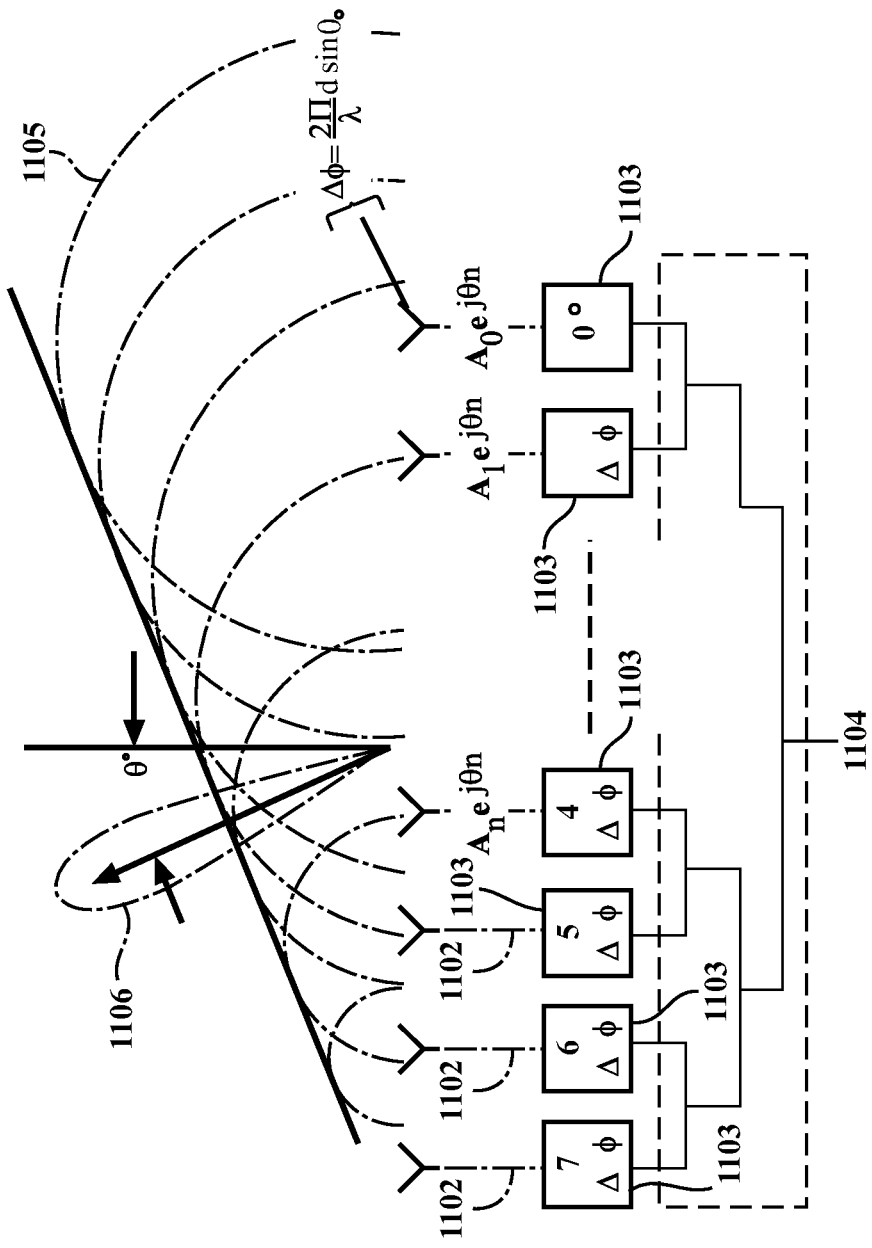
FIG. 11 shows a method for forming and steering a beam by the user of a plurality of radiators.

Referring to FIG. 11, shown is an example of an electrode array to affect beam forming and beam steering. Beam forming and steering allows a more selective application of stimulation energy by a TNSS to nerves and tissue. Beam steering also provides the opportunity for lower power for stimulation of cells including nerves by applying the stimulating mechanism directionally to a target. In the use of an electrical beam lower power demand lengthens battery life and allows for use of low power chip sets. Beam steering may be accomplished in multiple ways for instance by magnetic fields and formed gates. FIG. 11 shows a method for forming and steering a beam by the use of a plurality of radiators 1102 which are activated out of phase with each other by a plurality of phase shifters 1103 that are supplied power from a common source 1104. Because the radiated signals are out of phase they produce an interference pattern 1105 that results in the beam being formed and steered in varying controlled directions 1106. Electromagnetic radiation like light shows some properties of waves and can be focused on certain locations. This provides the opportunity to stimulate tissues such as nerves selectively. It also provides the opportunity to focus the transmission of energy and data on certain objects, including topical or implanted electronic devices, thereby not only improving the selectivity of activating or controlling those objects but also reducing the overall power required to operate them.

Figure 12:
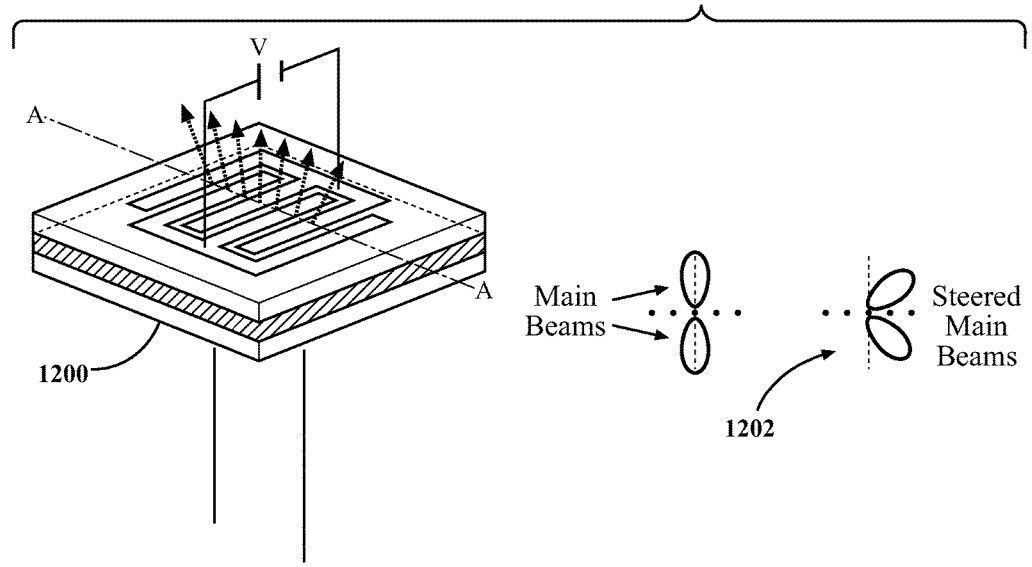
FIG. 12 is an exemplary beam forming and steering mechanism.

FIG. 12 is another example of a gating structure 1200 used for beam shaping and steering 1202. The gating structure 1200 shows an example of an interlocked pair of electrodes that can be used for simple beam forming through the application of time-varying voltages. The steering 1202 shows a generic picture of the main field lobes and how such beam steering works in this example. FIG. 12 is illustrative of a possible example that may be used.

The human and mammal body is an anisotropic medium with multiple layers of tissue of varying electrical properties. Steering of an electric field may be accomplished using multiple electrodes, or multiple SBAs, using the human or mammal body as an anisotropic volume conductor. Electric field steering will discussed below with reference to FIGS. 18 and 19.

Figure 13:
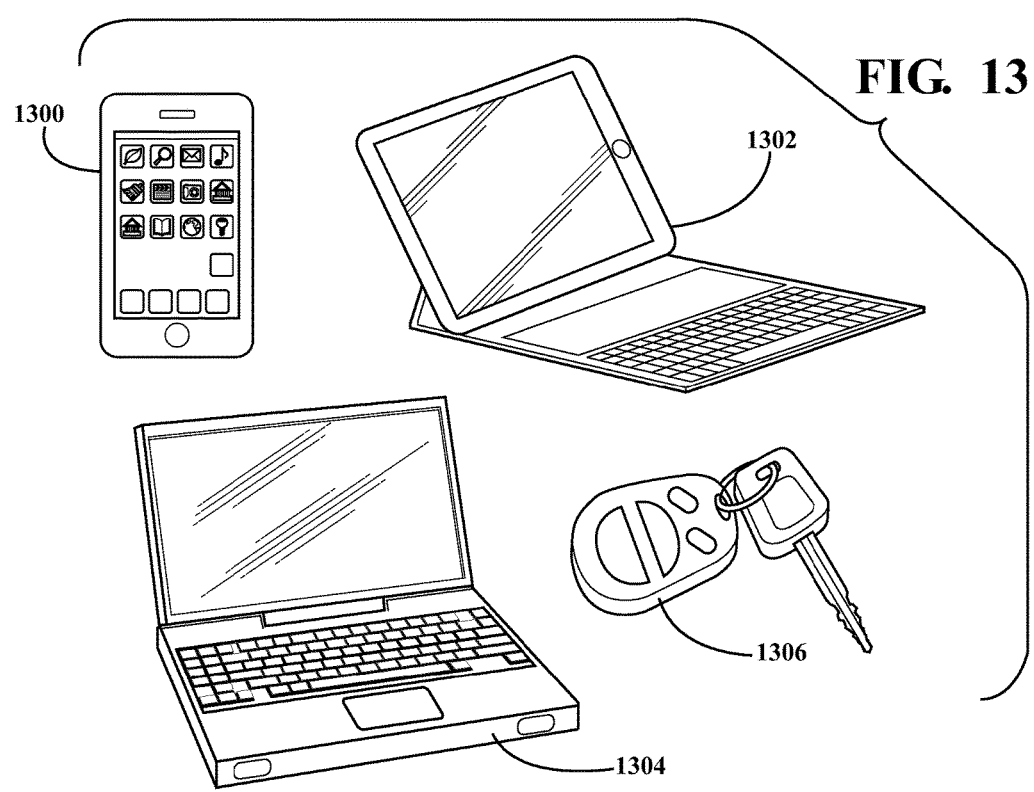
FIG. 13 illustrates exemplary Control Units for activating a nerve stimulation device.

Referring to FIG. 13, the controller is an electronics platform that is a smartphone 1300, tablet 1302, personal computer 1304, or dedicated module 1306 that hosts wireless communications capabilities, such as Near Field Communications, Bluetooth, or Wi-Fi technologies as enabled by the current set of communications chips, e.g. Broadcom BCM4334, TI WiLink 8 and others, and a wide range of protocol apps that can communicate with the TNSSs. There may be more than one controller, acting together. This may occur, for example, if the user has both a smartphone control app running, and a key fob controller in his/her pocket/purse.

TNSS protocol performs the functions of communications with the controller including transmitting and receiving of control and data signals, activation and control of the neural stimulation, data gathering from on board sensors, communications and coordination with other TNSSs, and data analysis. Typically the TNSS may receive commands from the controller, generate stimuli and apply these to the tissues, sense signals from the tissues, and transmit these to the controller. It may also analyze the signals sensed and use this information to modify the stimulation applied. In addition to communicating with the controller it may also communicate with other TNSSs using electrical or radio signals via a body area network.

Referring to FIG. 14, controller protocol executed and/or displayed on a smartphone 1400, tablet 1402 or other computing platform or mobile device, will perform the functions of communications with TNSS modules including transmitting and receiving of control and data signals, activation and control of the neuro modulation regimens, data gathering from on board sensors, communications and coordination with other controllers, and data analysis. In some cases local control of the neuro modulation regimens may be conducted by controller protocol without communications with the user.

FIG. 15 shows potential applications of electrical stimulation and sensing for the body, particularly for users who may suffer from paralysis or loss of sensation or altered reflexes such as spasticity or tremor due to neurological disorders and their complications, as well as users suffering from incontinence, pain, immobility and aging. Different example medical uses of the present system are discussed below.

Figure 16:
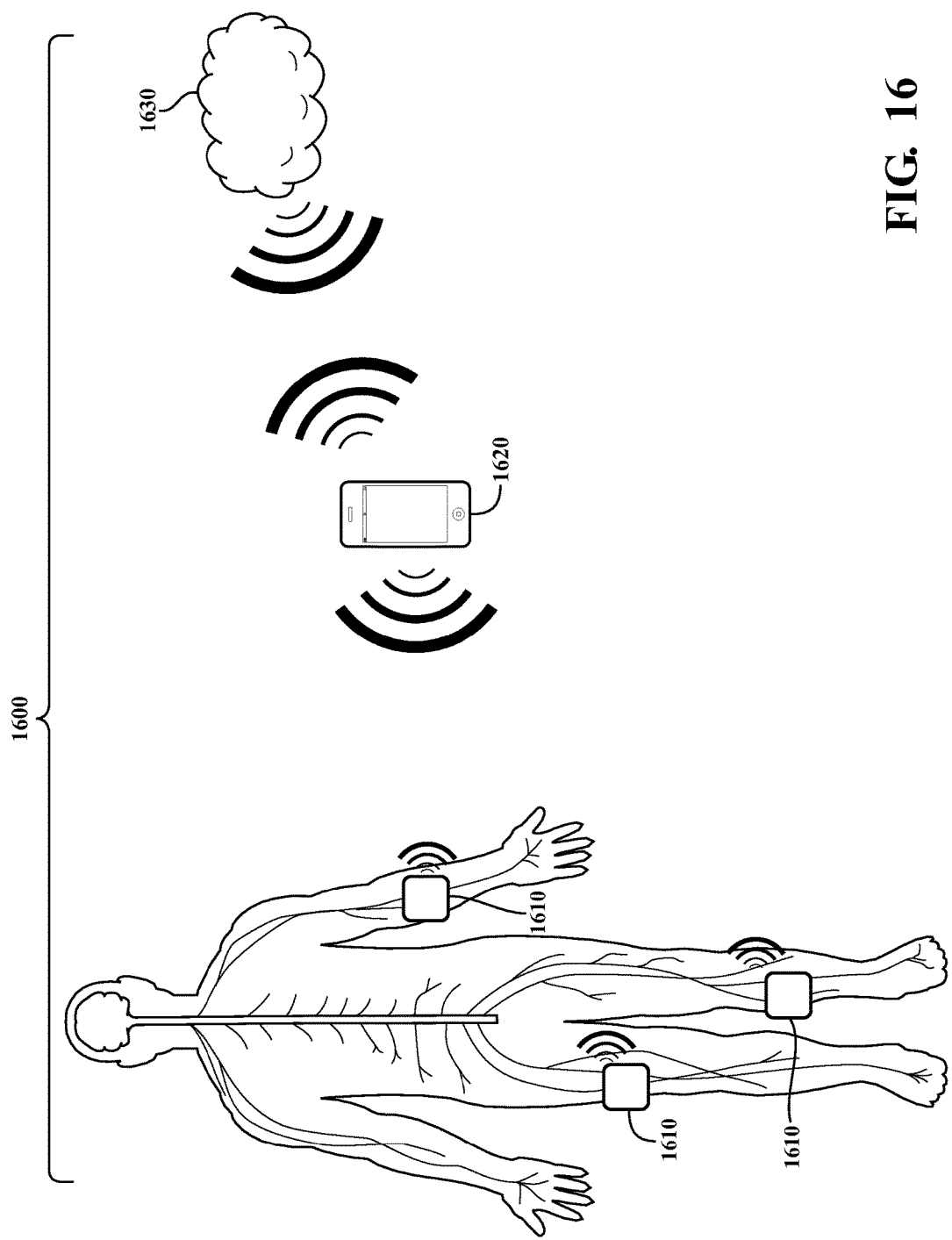
FIG. 16 shows an example TNSS system.

FIG. 16 shows the components of one example of a typical TNSS system 1600. TNSS devices 1610 are responsible for stimulation of nerves and for receiving data in the form of electrical, acoustic, imaging, chemical and other signals which then can be processed locally in the TNSS or passed to the Control Unit 1620. TNSS devices 1610 are also responsible for analysis and action. The TNSS device 1610 may contain a plurality of electrodes for stimulation and for sensing. The same electrodes may be used for both functions, but this is not required. The TNSS device 1610 may contain an imaging device, such as an ultrasonic transducer to create acoustic images of the structure beneath the electrodes or elsewhere in the body that may be affected by the neural stimulation.

In this example TNSS system, most of the data gathering and analysis is performed in the Control Unit 1620. The Control Unit 1620 may be a cellular telephone or a dedicated hardware device. The Control Unit 1620 runs an app that controls the local functions of the TNSS System 1600. The protocol app also communicates via the Internet or wireless networks 1630 with other TNSS systems and/or with 3rd party software applications.

Figure 17:
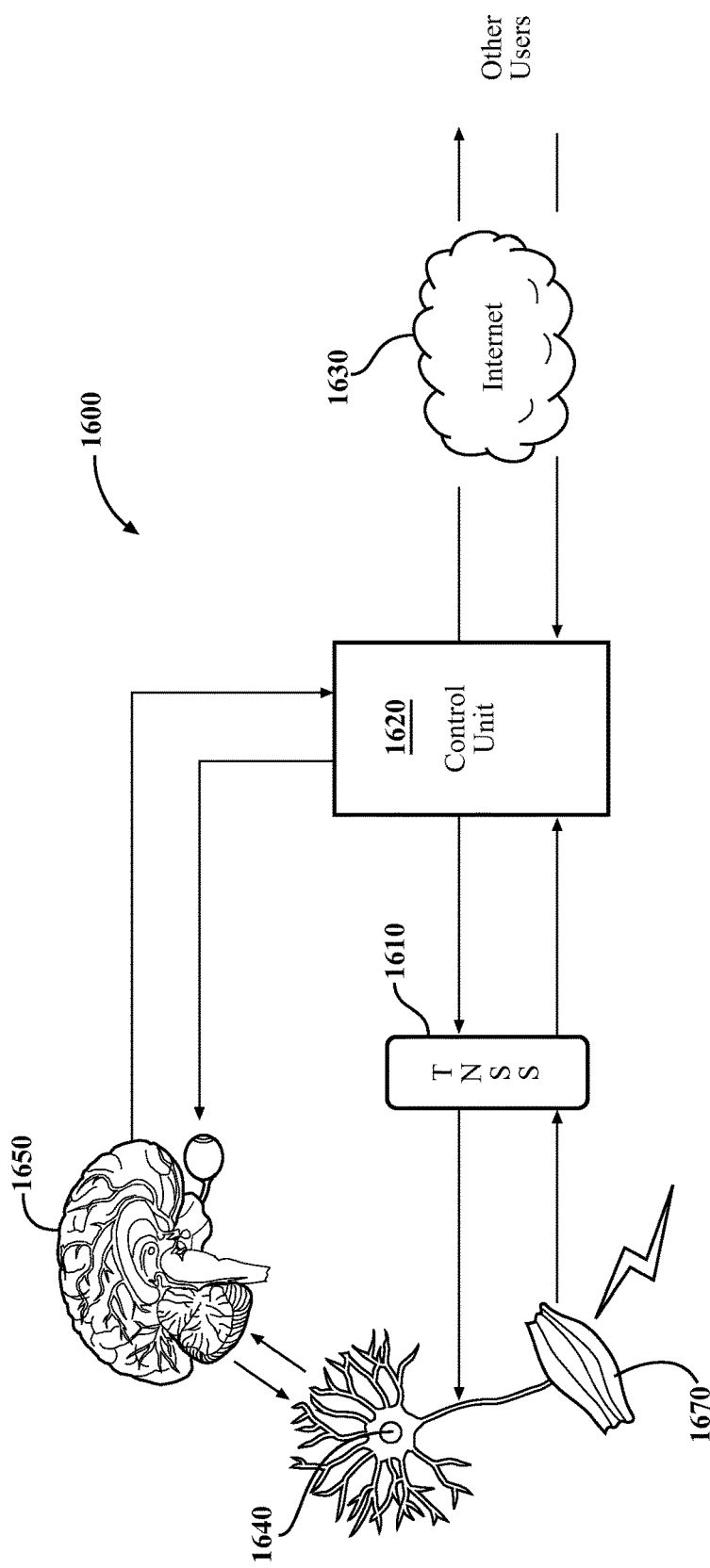
FIG. 17 shows communications among the components of the TNSS system of FIG. 16 and a user.

FIG. 17 shows the communications among the components of the TNSS system 1600 and the user. In this example, TNSS 1610 is capable of applying stimuli to nerves 1640 to produce action potentials in the nerves 1640 to produce actions in muscles 1670 or other organs such as the brain 1650. These actions may be sensed by the TNSS 1610, which may act on the information to modify the stimulation it provides. This closed loop constitutes the first level of the system 1600 in this example.

The TNSS 1610 may also be caused to operate by signals received from a Control Unit 1620 such as a cellphone, laptop, key fob, tablet, or other handheld device and may transmit information that it senses back to the Control Unit 1620. This constitutes the second level of the system 1600 in this example.

The Control Unit 1620 is caused to operate by commands from a user, who also receives information from the Control Unit 1620. The user may also receive information about actions of the body via natural senses such as vision or touch via sensory nerves and the spinal cord, and may in some cases cause actions in the body via natural pathways through the spinal cord to the muscles.

The Control Unit 1620 may also communicate information to other users, experts, or application programs via the Internet 1630, and receive information from them via the Internet 1630.

The user may choose to initiate or modify these processes, sometimes using protocol applications residing in the TNSS 1610, the Control Unit 1620, the Internet 1630, or wireless networks. This software may assist the user, for example by processing the stimulation to be delivered to the body to render it more selective or effective for the user, and/or by processing and displaying data received from the body or from the Internet 1630 or wireless networks to make it more intelligible or useful to the user.

Figure 18:
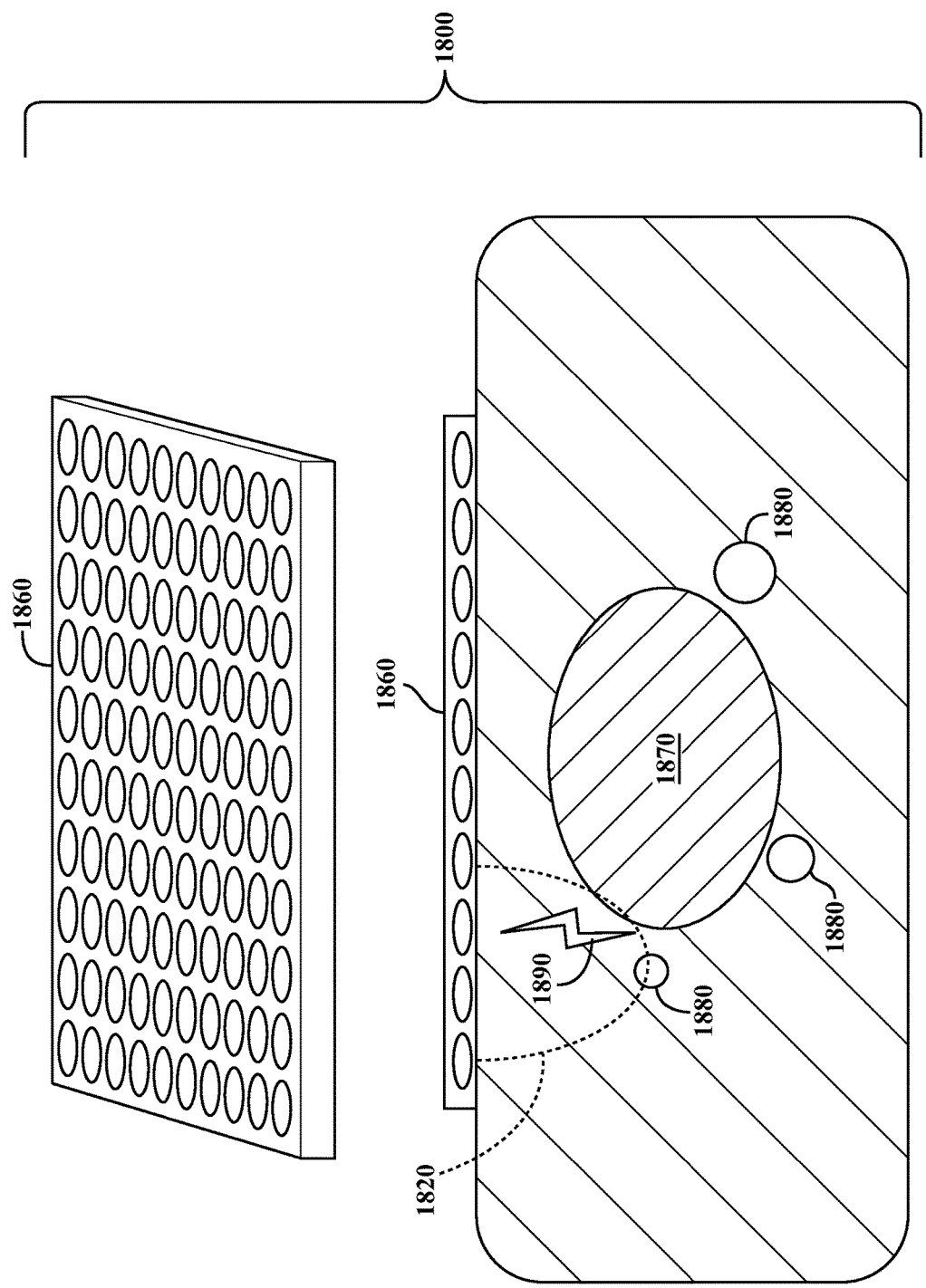
FIG. 18 shows an example electrode configuration for electric field steering and sensing.

FIG. 18 shows an example electrode configuration 1800 for Electric Field Steering. The application of an appropriate electric field to the body can cause a nerve to produce an electrical pulse known as an action potential. The shape of the electric field is influenced by the electrical properties of the different tissue through which it passes and the size, number and position of the electrodes used to apply it. The electrodes can therefore be designed to shape or steer or focus the electric field on some nerves more than on others, thereby providing more selective stimulation.

An example 10×10 matrix of electrical contacts 1860 is shown. By varying the pattern of electrical contacts 1860 employed to cause an electric field 1820 to form and by time varying the applied electrical power to this pattern of contacts 1860, it is possible to steer the field 1820 across different parts of the body, which may include muscle 1870, bone, fat, and other tissue, in three dimensions. This electric field 1820 can activate specific nerves or nerve bundles 1880 while sensing the electrical and mechanical actions produced 1890, and thereby enabling the TNSS to discover more effective or the most effective pattern of stimulation for producing the desired action.

Figure 19:
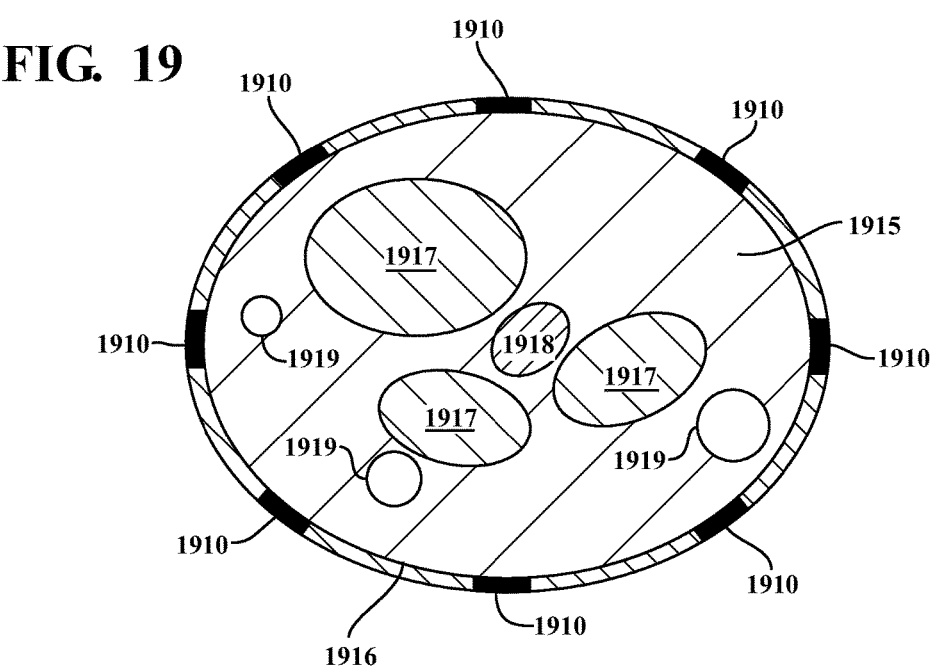
FIG. 19 shows an example of stimulating and sensing patterns of signals in a volume of tissue.

FIG. 19 shows a example of stimulating and sensing patterns of signals in a volume of tissue. Electrodes 1910 as part of a cuff arrangement are placed around limb 1915. The electrodes 1910 are external to a layer of skin 1916 on limb 1915. Internal components of the limb 1915 include muscle 1917, bone 1918, nerves 1919, and other tissues. By using electric field steering for stimulation, as described with reference to FIG. 18, the electrodes 1910 can activate nerves 1919 selectively. An array of sensors (e.g. piezoelectric sensors or micro-electro-mechanical sensors) in a TNSS can act as a phased array antenna for receiving ultrasound signals, to acquire ultrasonic images of body tissues. Electrodes 1910 may act as an array of electrodes sensing voltages at different times and locations on the surface of the body, with software processing this information to display information about the activity in body tissues, e.g. which muscles are activated by different patterns of stimulation.

The SBA's ability to stimulate and collect organic data has multiple applications including bladder control, reflex incontinence, sexual stimulations, pain control and wound healing among others. Examples of SBA's application for medical and other uses follow.

Medical Uses

Bladder Management

1) Overactive bladder: When the user feels a sensation of needing to empty the bladder urgently, he or she presses a button on the Controller to initiate stimulation via a Smart Band Aid™ applied over the dorsal nerve of the penis or clitoris. Activation of this nerve would inhibit the sensation of needing to empty the bladder urgently, and allow it to be emptied at a convenient time.

2) Incontinence: A person prone to incontinence of urine because of unwanted contraction of the bladder uses the SBA to activate the dorsal nerve of the penis or clitoris to inhibit contraction of the bladder and reduce incontinence of urine. The nerve could be activated continuously, or intermittently when the user became aware of the risk of incontinence, or in response to a sensor indicating the volume or pressure in the bladder.

Erection, ejaculation and orgasm: Stimulation of the nerves on the underside of the penis by a Smart Band Aid™ (electrical stimulation or mechanical vibration) can cause sexual arousal and might be used to produce or prolong erection and to produce orgasm and ejaculation.

Pain control: A person suffering from chronic pain from a particular region of the body applies a Smart Band Aid™ over that region and activates electrically the nerves conveying the sensation of touch, thereby reducing the sensation of pain from that region. This is based on the gate theory of pain.

Wound care: A person suffering from a chronic wound or ulcer applies a Smart Band Aid™ over the wound and applies electrical stimuli continuously to the tissues surrounding the wound to accelerate healing and reduce infection.

Essential tremor: A sensor on a Smart Band Aid™ detects the tremor and triggers neuro stimulation to the muscles and sensory nerves involved in the tremor with an appropriate frequency and phase relationship to the tremor. The stimulation frequency would typically be at the same frequency as the tremor but shifted in phase in order to cancel the tremor or reset the neural control system for hand position.

Reduction of spasticity: Electrical stimulation of peripheral nerves can reduce spasticity for several hours after stimulation. A Smart Band Aid™ operated by the patient when desired from a smartphone could provide this stimulation.

Restoration of sensation and sensory feedback: People who lack sensation, for example as a result of diabetes or stroke use a Smart Band Aid™ to sense movement or contact, for example of the foot striking the floor, and the SBA provides mechanical or electrical stimulation to another part of the body where the user has sensation, to improve safety or function. Mechanical stimulation is provided by the use of acoustic transducers in the SBA such as small vibrators. Applying a Smart Band Aid™ to the limb or other assistive device provides sensory feedback from artificial limbs. Sensory feedback can also be used to substitute one sense for another, e.g. touch in place of sight.

Recording of mechanical activity of the body: Sensors in a Smart Band Aid™ record position, location and orientation of a person or of body parts and transmit this data to a smartphone for the user and/or to other computer networks for safety monitoring, analysis of function and coordination of stimulation.

Recording of sound from the body or reflections of ultrasound waves generated by a transducer in a Smart Band Aid™ could provide information about body structure, e.g. bladder volume for persons unable to feel their bladder. Acoustic transducers may be piezoelectric devices or MEMS devices that transmit and receive the appropriate acoustic frequencies. Acoustic data may be processed to allow imaging of the interior of the body.

Recording of Electrical Activity of the Body

Electrocardiogram: Recording the electrical activity of the heart is widely used for diagnosing heart attacks and abnormal rhythms. It is sometimes necessary to record this activity for 24 hours or more to detect uncommon rhythms. A Smart Band Aid™ communicating wirelessly with a smartphone or computer network achieves this more simply than present systems.

Electromyogram: Recording the electrical activity of muscles is widely used for diagnosis in neurology and also used for movement analysis. Currently this requires the use of many needles or adhesive pads on the surface of the skin connected to recording equipment by many wires. Multiple Smart Band Aids™ record the electrical activity of many muscles and transmit this information wirelessly to a smartphone.

Recording of optical information from the body: A Smart Band Aid™ incorporating a light source (LED, laser) illuminates tissues and senses the characteristics of the reflected light to measure characteristics of value, e.g. oxygenation of the blood, and transmit this to a cellphone or other computer network.

Recording of chemical information from the body: The levels of chemicals or drugs in the body or body fluids is monitored continuously by a Smart Band Aid™ sensor and transmitted to other computer networks and appropriate feedback provided to the user or to medical staff. Levels of chemicals may be measured by optical methods (reflection of light at particular wavelengths) or by chemical sensors.

Special Populations of Disabled Users

There are many potential applications of electrical stimulation for therapy and restoration of function. However, few of these have been commercialized because of the lack of affordable convenient and easily controllable stimulation systems. Some applications are shown in the FIG. 15.

Limb Muscle stimulation: Lower limb muscles can be exercised by stimulating them electrically, even if they are paralyzed by stroke or spinal cord injury. This is often combined with the use of a stationary exercise cycle for stability. Smart Band Aid™ devices could be applied to the quadriceps muscle of the thigh to stimulate these, extending the knee for cycling, or to other muscles such as those of the calf. Sensors in the Smart Band Aid™ could trigger stimulation at the appropriate time during cycling, using an application on a smartphone, tablet, handheld hardware device such as a key fob, wearable computing device, laptop, or desktop computer, among other possible devices. Upper limb muscles can be exercised by stimulating them electrically, even if they are paralyzed by stroke of spinal cord injury. This is often combined with the use of an arm crank exercise machine for stability. Smart Band Aid™ devices are applied to multiple muscles in the upper limb and triggered by sensors in the Smart Band Aids™ at the appropriate times, using an application on a smartphone.

Prevention of osteoporosis: Exercise can prevent osteoporosis and pathological fractures of bones. This is applied using Smart Band Aids™ in conjunction with exercise machines such as rowing simulators, even for people with paralysis who are particularly prone to osteoporosis.

Prevention of deep vein thrombosis: Electric stimulation of the muscles of the calf can reduce the risk of deep vein thrombosis and potentially fatal pulmonary embolus. Electric stimulation of the calf muscles is applied by a Smart Band Aid™ with stimulation programmed from a smartphone, e.g. during a surgical operation, or on a preset schedule during a long plane flight.

Restoration of Function (Functional Electrical Stimulation)

Lower Limb

1) Foot drop: People with stroke often cannot lift their forefoot and drag their toes on the ground. A Smart Band Aid™ is be applied just below the knee over the common peroneal nerve to stimulate the muscles that lift the forefoot at the appropriate time in the gait cycle, triggered by a sensor in the Smart Band Aid™

2) Standing: People with spinal cord injury or some other paralyses can be aided to stand by electrical stimulation of the quadriceps muscles of their thigh. These muscles are stimulated by Smart Band Aids™ applied to the front of the thigh and triggered by sensors or buttons operated by the patient using an application on a smartphone. This may also assist patients to use lower limb muscles when transferring from a bed to a chair or other surface.

3) Walking: Patients with paralysis from spinal cord injury are aided to take simple steps using electrical stimulation of the lower limb muscles and nerves. Stimulation of the sensory nerves in the common peroneal nerve below the knee can cause a triple reflex withdrawal, flexing the ankle, knee and hip to lift the leg, and then stimulation of the quadriceps can extend the knee to bear weight. The process is then repeated on the other leg. Smart Band Aids™ coordinated by an application in a smartphone produce these actions.

Upper Limb

1) Hand grasp: People with paralysis from stroke or spinal cord injury have simple hand grasp restored by electrical stimulation of the muscles to open or close the hand. This is produced by Smart Band Aids™ applied to the back and front of the forearm and coordinated by sensors in the Smart Band Aids™ and an application in a smartphone.

2) Reaching: Patients with paralysis from spinal cord injury sometimes cannot extend their elbow to reach above the head. Application of a Smart Band Aid™ to the triceps muscle stimulates this muscle to extend the elbow. This is triggered by a sensor in the Smart Band Aid™ detecting arm movements and coordinating it with an application on a smartphone.

Posture: People whose trunk muscles are paralyzed may have difficulty maintaining their posture even in a wheelchair. They may fall forward unless they wear a seatbelt, and if they lean forward they may be unable to regain upright posture. Electrical stimulation of the muscles of the lower back using a Smart Band Aid™ allows them to maintain and regain upright posture. Sensors in the Smart Band Aid™ trigger this stimulation when a change in posture was detected.

Coughing: People whose abdominal muscles are paralyzed cannot produce a strong cough and are at risk for pneumonia. Stimulation of the muscles of the abdominal wall using a Smart Band Aid™ could produce a more forceful cough and prevent chest infections. The patient using a sensor in a Smart Band Aid™ triggers the stimulation.

Essential Tremor: It has been demonstrated that neuro stimulation can reduce or eliminate the signs of ET. ET may be controlled using a TNSS. A sensor on a Smart Band Aid™ detects the tremor and trigger neuro stimulation to the muscles and sensory nerves involved in the tremor with an appropriate frequency and phase relationship to the tremor. The stimulation frequency is typically be at the same frequency as the tremor but shifted in phase in order to cancel the tremor or reset the neural control system for hand position.

Non-Medical Applications
Sports Training

Sensing the position and orientation of multiple limb segments is used to provide visual feedback on a smartphone of, for example, a golf swing, and also mechanical or electrical feedback to the user at particular times during the swing to show them how to change their actions. The electromyogram of muscles could also be recorded from one or many Smart Band Aids™ and used for more detailed analysis.

Gaming

Sensing the position and orientation of arms, legs and the rest of the body produces a picture of an onscreen player that can interact with other players anywhere on the Internet. Tactile feedback would be provided to players by actuators in Smart Band Aids on various parts of the body to give the sensation of striking a ball, etc.

Motion Capture for Film and Animation

Wireless TNSS capture position, acceleration, and orientation of multiple parts of the body. This data may be used for animation of a human or mammal and has application for human factor analysis and design.

Sample Modes of Operation

A SBA system consists of at least a single Controller and a single SBA. Following application of the SBA to the user's skin, the user controls it via the Controller's app using Near Field Communications. The app appears on a smartphone screen and can be touch controlled by the user; for 'key fob' type Controllers, the SBA is controlled by pressing buttons on the key fob.

When the user feels the need to activate the SBA s/he presses the "go" button two or more times to prevent false triggering, thus delivering the neuro stimulation. The neuro stimulation may be delivered in a variety of patterns of frequency, duration, and strength and may continue until a button is pressed by the user or may be delivered for a length of time set in the application.

Sensor capabilities in the TNSS, are enabled to start collecting/analyzing data and communicating with the controller when activated.

The level of functionality in the protocol app, and the protocol embedded in the TNSS, will depend upon the neuro modulation or neuro stimulation regimen being employed.

In some cases there will be multiple TNSSs employed for the neuro modulation or neuro stimulation regimen. The basic activation will be the same for each TNSS.

However, once activated multiple TNSSs will automatically form a network of neuro modulation/stimulation points with communications enabled with the controller.

The need for multiple TNSSs arises from the fact that treatment regimens may need several points of access to be effective.

While illustrative systems and methods as described herein embodying various aspects of the present disclosure are shown, it will be understood by those skilled in the art, that the invention is not limited to these embodiments. Modifications may be made by those skilled in the art, particularly in light of the foregoing teachings. For example, each of the elements of the aforementioned embodiments may be utilized alone or in combination or subcombination with elements of the other embodiments. It will also be appreciated and understood that modifications may be made without departing from the true spirit and scope of the present disclosure. The description is thus to be regarded as illustrative instead of restrictive on the present invention.

We claim:

1. A topical nerve stimulator system comprising:
a flexible dermis conforming patch defining a surface and formed by a substrate;
electrodes positioned on the patch proximal the surface and directly coupled to the substrate;
electronic circuitry embedded in the patch comprising a system on a chip that is directly coupled to the substrate and comprising:
an electrical signal generator configured to electrically activate the electrodes;
a signal receiver in communication with the electrical signal generator;
an antenna;
a transmitter; and
a receiver;
a remote control device in wireless communication with the electronic circuitry, the remote control device configured to provide a signal to start stimulation on a user via the electrodes, the signal generated in response to the user interacting with the remote control device.

2. The topical nerve stimulator system of claim 1, the surface further comprises adhesive.

3. The topical nerve stimulator system of claim 1, further comprising a feedback sensor on the patch coupled to the substrate and configured to sense muscle and/or nerve activation and communicate data to the remote control device.

4. The topical nerve stimulator system of claim 1, the remote control device is a smartphone and the signal is generated via a smartphone app.

5. The topical nerve stimulator system of claim 1, the remote control device is a key fob controller comprising a button and the signal is generated via a pressing of the button.

6. The topical nerve stimulator system of claim 3, the stimulation based on a stimulation pattern that is revised in response to the sensed muscle and/or nerve activation.

7. The topical nerve stimulator system of claim 1, the electrodes configured to stimulate a mammalian nerve.

8. The topical nerve stimulator system of claim 1, the remote control device comprising a user interface configured to provide visual, audio and tactile feedback to a user.

9. A method for controlling a body function of a user comprising:
   applying a flexible dermis conforming patch to a dermis of the user in proximity to a selected nerve, the patch formed by a substrate and comprising electrodes directly coupled to the substrate, electronic circuitry embedded in the patch comprising a system on a chip that is directly coupled to the substrate and comprising an electrical signal generator configured to electrically activate the electrodes, a signal receiver in communication with the electric signal generator, an antenna, a transmitter and a receiver;
   applying an electrical signal generated by the flexible dermis conforming patch to the selected nerve; and
   sensing nerve stimulation response;
   the applying in response to a signal to start stimulation on the user via the electrodes from a remote control device in wireless communication with the electronic circuitry, the signal generated in response to the user interacting with the remote control device.

10. The method of claim 9 further comprising monitoring the nerve response to the electrical signal and adjusting a nerve stimulation pattern that is revised in response to the nerve response.

11. The method of claim 9 further comprising monitoring a muscle response to the nerve stimulation and adjusting a nerve stimulation pattern that is revised in response to the nerve response.

12. The method of claim 9, the remote control device is a smartphone and the signal is generated via a smartphone app.

13. The method of claim 9, the remote control device is a key fob controller comprising a button and the signal is generated via a pressing of the button.

14. The method of claim 9 further comprising applying the flexible dermis conforming patch to the dermis with adhesive.

15. The method of claim 9 further comprising applying more than one flexible dermis conforming patches to the dermis.

16. The method of claim 9 further comprising stimulating more than one nerve with one or more flexible dermis conforming patches to create a nerve stimulation pattern.

17. The method of claim 9 further comprising applying the electrical signal to a selected portion of a nerve.

18. The method of claim 9 further comprising selectively adjusting a strength of the electrical signal.

19. The method of claim 9 further comprising selectively adjusting a shape of the electrical signal.

20. The method of claim 9 further comprising receiving a signal feedback from a stimulated nerve.

21. The method of claim 9 further comprising receiving feedback from a stimulated nerve and adjusting the electrical signal based on the feedback.

22. The method of claim 9, the remote control device comprising a user interface configured to provide visual, audio and tactile feedback to a user.

23. A topical nerve stimulator patch comprising:
   a substrate;
   electrodes positioned on the patch proximal the surface and directly coupled to the substrate;
   electronic circuitry embedded in the patch comprising a system on a chip that is directly coupled to the substrate and comprising:
      an electrical signal generator configured to electrically activate the electrodes;
      a signal receiver in communication with the electrical signal generator;
      an antenna;
      a transmitter; and
      a receiver;
   the electrical circuitry configured to be in wireless communication with a remote control device, the remote control device configured to provide a signal to start stimulation on a user via the electrodes, the signal generated in response to the user interacting with the remote control device.

24. The topical nerve stimulator patch of claim 23, further comprising a feedback sensor on the patch coupled to the substrate and configured to sense muscle and/or nerve activation and communicate data to the remote control device.

25. The topical nerve stimulator patch of claim 24, the stimulation based on a stimulation pattern that is revised in response to the sensed muscle and/or nerve activation.

\* \* \* \* \*